United States Patent
Ambati

(10) Patent No.: US 9,464,289 B2
(45) Date of Patent: *Oct. 11, 2016

(54) METHODS OF INHIBITING ALU RNA AND THERAPEUTIC USES THEREOF

(71) Applicant: University of Kentucky Research Foundation, Lexington, KY (US)

(72) Inventor: Jayakrishna Ambati, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/323,457

(22) Filed: Jul. 3, 2014

(65) Prior Publication Data

US 2014/0342357 A1 Nov. 20, 2014

Related U.S. Application Data

(62) Division of application No. 13/701,450, filed as application No. PCT/US2011/038753 on Jun. 1, 2011, now Pat. No. 8,809,517.

(60) Provisional application No. 61/396,747, filed on Jun. 1, 2010, provisional application No. 61/432,110, filed on Jan. 12, 2011, provisional application No. 61/432,948, filed on Jan. 14, 2011.

(51) Int. Cl.

| | |
|---|---|
| *C12N 15/11* | (2006.01) |
| *C12N 15/113* | (2010.01) |
| *C12Q 1/68* | (2006.01) |
| *C12N 9/22* | (2006.01) |
| *G01N 33/53* | (2006.01) |

(52) U.S. Cl.

CPC .............. *C12N 15/113* (2013.01); *C12N 9/22* (2013.01); *C12Q 1/6804* (2013.01); *C12Q 1/6876* (2013.01); *C12Q 1/6883* (2013.01); *G01N 33/5308* (2013.01); *C12N 2310/113* (2013.01); *C12N 2320/30* (2013.01); *C12Q 2600/136* (2013.01); *C12Q 2600/158* (2013.01); *C12Y 301/26003* (2013.01); *G01N 2500/10* (2013.01)

(58) Field of Classification Search
None
See application file for complete search history.

(56) References Cited

FOREIGN PATENT DOCUMENTS

WO      WO 0029622 A2 *   5/2000

OTHER PUBLICATIONS

Shaikh, T. H., Roy, A. M., Kim, J., Batzer, M. A. & Deininger, P. L. cDNAs derived from primary and small cytoplasmic Alu (scAlu) transcripts. J Mol Biol 271, 222-234 (1997).
Sinnett, D., Richer, C., Deragon, J. M. & Labuda, D. Alu RNA transcripts in human embryonal carcinoma cells. Model of post-transcriptional selection of master sequences. J Mol Biol 226, 689-706 (1992).
Rattner, A., Toulabi, L., Williams, J., Yu, H. & Nathans, J. The genomic response of the retinal pigment epithelium to light damage and retinal detachment. J Neurosci 28, 9880-9889 (2008).
Huang, H. et al. Identification of mouse retinal genes differentially regulated by dim and bright cyclic light rearing. Exp Eye Res 80, 727-739 (2005).
Natoli, R., Provis, J., Valter, K. & Stone, J. Gene regulation induced in the C57BL/6J mouse retina by hyperoxia: a temporal microarray study. Mol Vis 14, 1983-1994 (2008).
Farjo, R., Peterson, W. M. & Naash, M. I. Expression profiling after retinal detachment and reattachment: a possible role for aquaporin-0. Invest Ophthalmol Vis Sci 49, 511-521 (2008).
Livesey, F. J., Furukawa, T., Steffen, M. A., Church, G. M. & Cepko, C. L. Microarray analysis of the transcriptional network controlled by the photoreceptor homeobox gene Crx. Curr Biol 10, 301-310 (2000).
Gehrig, A. et al. Genome-wide expression profiling of the retinoschisin-deficient retina in early postnatal mouse development. Invest Ophthalmol Vis Sci 48, 891-900 (2007).
Hackam, A. S. et al. Identification of gene expression changes associated with the progression of retinal degeneration in the rd1 mouse. Invest Ophthalmol Vis Sci 45, 2929-2942 (2004).
Punzo, C. & Cepko, C. Cellular responses to photoreceptor death in the rd1 mouse model of retinal degeneration. Invest Ophthalmol Vis Sci 48, 849-857 (2007).
Schaeferhoff, K. et al. Induction of STAT3-related genes in fast degenerating cone photoreceptors of cpfl1 mice. Cell Mol Life Sci 67, 3173-3186 (2010).
Gelineau-van Waes, J. et al. Altered expression of the iron transporter Nramp1 (Slc11a1) during fetal development of the retinal pigment epithelium in microphthalmia-associated transcription factor Mitf(mi) and Mitf(vitiligo) mouse mutants. Exp Eye Res 86, 419-433 (2008).
Tian, J. et al. Advanced glycation endproduct-induced aging of the retinal pigment epithelium and choroid: a comprehensive transcriptional response. Proc Natl Acad Sci U S A 102, 11846-11851 (2005).
Zacks, D. N., Han, Y., Zeng, Y. & Swaroop, A. Activation of signaling pathways and stress-response genes in an experimental model of retinal detachment. Invest Ophthalmol Vis Sci 47, 1691-1695 (2006).
Chong, M. M., Rasmussen, J. P., Rudensky, A. Y. & Littman, D. R. The RNAseIII enzyme Drosha is critical in T cells for preventing lethal inflammatory disease. J Exp Med 205, 2005-2017 (2008).
Iacovelli, J. et al. Generation of cre transgenic mice with postnatal RPE-specific ocular expression. Invest Ophthalmol Vis Sci, In press (2010).

(Continued)

*Primary Examiner* — Kate Poliakova-Georgantas
(74) *Attorney, Agent, or Firm* — Stites & Harbison PLLC; Mandy Wilson Decker

(57) ABSTRACT

The presently-disclosed subject matter includes methods of identifying an Alu RNA inhibitor, and methods and compositions for inhibiting Alu RNA. Methods and compositions can be used for the treatment of geographic atrophy and other conditions of interest.

2 Claims, 25 Drawing Sheets

(56) References Cited

OTHER PUBLICATIONS

Yi, R. et al. DGCR8-dependent microRNA biogenesis is essential for skin development. Proc Natl Acad Sci U S A 106, 498-502 (2009).

Zhong, J., Peters, A. H., Lee, K. & Braun, R. E. A double-stranded RNA binding protein required for activation of repressed messages in mammalian germ cells. Nat Genet 22, 171-174 (1999).

Ambati, J. et al. An animal model of age-related macular degeneration in senescent Ccl-2- or Ccr-2-deficient mice. Nat Med 9, 1390-1397 (2003).

Takeda, A. et al. CCR3 is a target for age-related macular degeneration diagnosis and therapy. Nature 460, 225-230 (2009).

Hahn, P. et al. Disruption of ceruloplasmin and hephaestin in mice causes retinal iron overload and retinal degeneration with features of age-related macular degeneration. Proc Natl Acad Sci U S A 101, 13850-13855 (2004).

O'Carroll, D. et al. A Slicer-independent role for Argonaute 2 in hematopoiesis and the microRNA pathway. Genes Dev 21, 1999-2004 (2007).

Schaefer, A. et al. Argonaute 2 in dopamine 2 receptor-expressing neurons regulates cocaine addiction. J Exp Med 207, 1843-1851 (2010).

Provost, P. et al. Ribonuclease activity and RNA binding of recombinant human Dicer. EMBO J 21, 5864-5874 (2002).

Bennett, E. A. et al. Active Alu retrotransposons in the human genome. Genome Res 18, 1875-1883 (2008).

Hagan, C. R., Sheffield, R. F. & Rudin, C. M. Human Alu element retrotransposition induced by genotoxic stress. Nat Genet 35, 219-220 (2003).

Misra, S., Tripathi, M. K. & Chaudhuri, G. Down-regulation of 7SL RNA expression and impairment of vesicular protein transport pathways by Leishmania infection of macrophages. J Biol Chem 280, 29364-29373 (2005).

Alexander, J. J. & Hauswirth, W. W. Adeno-associated viral vectors and the retina. Adv Exp Med Biol 613, 121-128 (2008).

Maan, S. et al. Rapid cDNA synthesis and sequencing techniques for the genetic study of bluetongue and other dsRNA viruses. J Virol Methods 143, 132-139 (2007).

Potgieter, A. C. et al. Improved strategies for sequence-independent amplification and sequencing of viral double-stranded RNA genomes. J Gen Virol 90, 1423-1432 (2009).

Kohany, O., Gentles, A. J., Hankus, L. & Jurka, J. Annotation, submission and screening of repetitive elements in Repbase: RepbaseSubmitter and Censor. BMC Bioinformatics 7, 474 (2006).

Altschul, S. F., Gish, W., Miller, W., Myers, E. W. & Lipman, D. J. Basic local alignment search tool. J Mol Biol 215, 403-410 (1990).

Allen, T. A., Von Kaenel, S., Goodrich, J. A. & Kugel, J. F. The SINE-encoded mouse B2 RNA represses mRNA transcription in response to heat shock. Nat Struct Mol Biol 11, 816-821 (2004).

Tripathi, M. K. & Chaudhuri, G. Down-regulation of UCRP and UBE2L6 in BRCA2 knocked-down human breast cells. Biochem Biophys Res Commun 328, 43-48 (2005).

Kanellopoulou, C. et al. Dicer-deficient mouse embryonic stem cells are defective in differentiation and centromeric silencing. Genes Dev 19, 489-501 (2005).

Yang, P., Tyrrell, J., Han, I. & Jaffe, G. J. Expression and modulation of RPE cell membrane complement regulatory proteins. Invest Ophthalmol Vis Sci 50, 3473-3481 (2009).

Yang, Z. et al. Toll-like receptor 3 and geographic atrophy in age-related macular degeneration. N Engl J Med 359, 1456-1463 (2008).

Gu, et al., "Alu-directed transcriptional regulation of some novel miRNAs" BMC Genomics, Nov. 30, 2009, vol. 10, No. 563, Abstract and Figure 3.

NCBI GenBank Accession No. HSU67825, Aug. 1, 1997.

Moolhuijzen, et al., "The transcript repeat element: the human Alu sequence as a component of gene networks influencing cancer" Funct. Integr. Genomics, Apr. 15, 2010, vol. 10, pp. 307-319.

Hulme, et al., "Selective inhibition of Alu retrotransposition by APOBEC3G." Gene, Sep. 27, 2006, vol. 390, pp. 199-205.

Bogerd, et al., "Cellular inhibitors of long interspersed element 1 and Alu retrotransposition." Proc. Natl. Acad. Sci US, Jun. 6, 2006, vol. 103, No. 23, pp. 8780-8785.

Haneko, et al., "DICER1 deficit induces Alu RNA toxicity in age-related macular degeneration." Nature, Mar. 17, 2011, vol. 471, No. 7338, pp. 325-330.

* cited by examiner

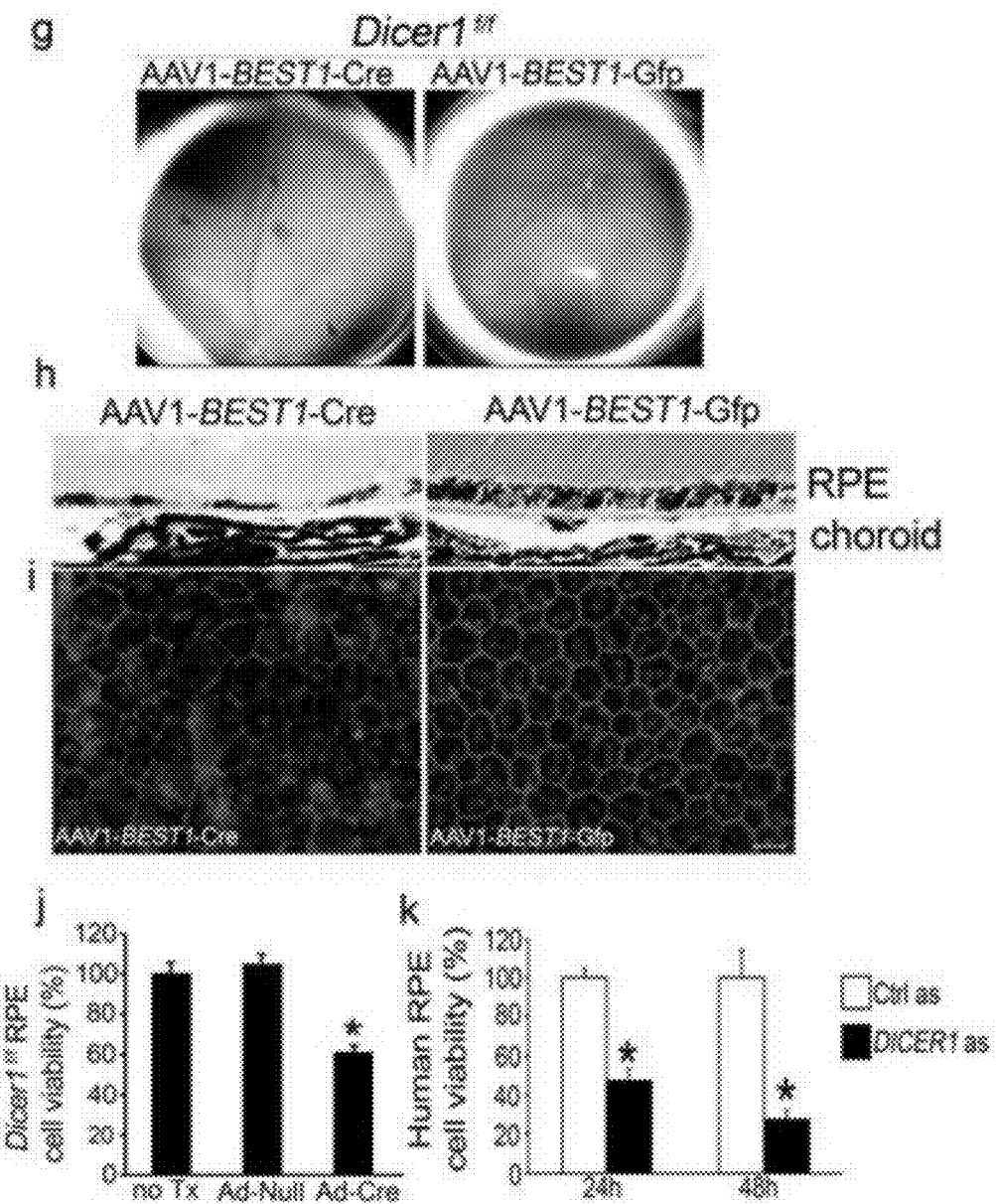
FIG. 1, Continued

METHODS OF INHIBITING ALU RNA AND THERAPEUTIC USES THEREOF

RELATED APPLICATIONS

This application is a divisional of U.S. patent application Ser. No. 13/701,450, now allowed, which is a 371 application of International Patent Application No. PCT/US2011/038753, filed Jun. 1, 2011, which claims priority from U.S. Provisional Application Ser. No. 61/396,747, filed on Jun. 1, 2010; U.S. Provisional Application Ser. No. 61/432,110, filed Jan. 12, 2011; and U.S. Provisional Application Ser. No. 61/432,948, filed Jan. 14, 2011. The entire disclosures of these applications are incorporated herein by this reference.

TECHNICAL FIELD

The presently-disclosed subject matter relates to uses of DICER overexpression and the inhibition of Alu RNA.

INTRODUCTION

Geographic atrophy, an advanced form of age-related macular degeneration that causes blindness in millions of people worldwide and for which there is no approved treatment, results from death of retinal pigmented epithelium (RPE) cells. As described herein the present inventors show that expression of DICER, an enzyme involved in microRNA (miRNA) biogenesis, is reduced in the RPE of human eyes with geographic atrophy, and that conditional ablation of Dicer1 induces RPE degeneration in mice. Surprisingly, ablation of seven other enzymes responsible for miRNA biogenesis or function does not induce such pathology. Instead, knockdown of DICER1 leads to accumulation of Alu repeat RNA in human RPE cells and of B1 and B2 (Alu-like elements) repeat RNAs in the RPE of mice.

Alu RNA is dramatically increased in the RPE of human eyes with geographic atrophy, and introduction of this pathological RNA induces death of human RPE cells and RPE degeneration in mice.

Antisense oligonucleotides targeting Alu/B1/B2 RNAs inhibit DICER1 depletion-induced RPE degeneration despite persistence of global miRNA downregulation. DICER1 degrades Alu RNA, and Alu RNA loses the ability to induce RPE degeneration in mice when digested by DICER1. These findings reveal a novel miRNA-independent cell survival function for DICER1 via degradation of retrotransposon transcripts, introduce the concept that Alu RNA can directly cause human pathology, and identify new molecular targets for treating a major cause of blindness.

Age-related macular degeneration (AMD), which is as prevalent as cancer in industrialized countries, is a leading cause of blindness worldwide. In contrast to the neovascular form of AMD, for which many approved treatments exist[1], the far more common atrophic form of AMD remains poorly understood and without effective clinical intervention[2]. Extensive atrophy of the retinal pigment epithelium (RPE) leads to severe vision loss and is termed geographic atrophy, the pathogenesis of which is unclear. As described herein, the present inventors identify dysregulation of the RNase DICER1[3] and the resulting accumulation of transcripts of Alu elements, the most common small interspersed repetitive elements in the human genome[4], as a cause of geographic atrophy, and describe treatment strategies to inhibit this pathology in vivo.

SUMMARY

The presently-disclosed subject matter meets some or all of the needs identified herein, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In some embodiments, the presently-disclosed subject matter includes a method of identifying an Alu RNA inhibitor. The method can include providing a cell in culture wherein Alu RNA is upregulated; contacting the cell with a candidate compound; and determining whether the candidate compound results in a change in the Alu RNA. In some embodiments, the cell is an RPE cell. In some embodiments, the Alu RNA can be upregulated by decreasing native levels of DICER polypeptides in the cell. In some embodiments, the Alu RNA can be upregulated using heat shock stress. In some embodiments, the change in the Alu RNA is a measurable decrease in Alu RNA, said change being an indication that the candidate compound is an Alu RNA inhibitor.

In some embodiments, the presently-disclosed subject matter includes a method of treating geographic atrophy, including inhibiting Alu RNA associated with an RPE cell. In some embodiments, the presently-disclosed subject matter includes a method of protecting an RPE cell, including inhibiting Alu RNA associated with the RPE cell. In some embodiments, the RPE cell is of a subject having age-related macular degeneration.

In some embodiments, the presently-disclosed subject matter includes a method of treating a condition of interest, including inhibiting Alu RNA associated with a cell of a subject. In some embodiments, the condition of interest is selected from: geographic atrophy, dry age-related macular degeneration, thallasemia, familial hypercholesterolemia, Dent's disease, acute intermittent porphyria, anterior pituitary aplasia, Apert syndrome, Hemophilia A, Hemophilia B, glycerol kinase deficiency, autoimmune lymphoproliferative syndrome, X-linked agammaglobulinemia, X-linked severe combined immunodeficiency, adrenoleukodystrophy, Menkes disease, hyper-immunoglobulin M syndrome, retinal blinding, Type 1 anti-thrombin deficiency, Muckle-Wells syndrome, hypocalciuric hypercalcemia and hyperparathyroidism, cholinesterase deficiency, hereditary desmoid disease, chronic hemolytic anemia, cystic fibrosis, branchio-oto-renal syndrome, lipoprotein lipase deficiency, CHARGE syndrome, Walker Warburg syndrome, Complement deficiency, Mucolipidosis type II, Breast cancer, ovarian cancer, prostate cancer, von Hippel Lindau disease, Hereditary non-polyposis colorectal cancer, multiple endocrine neoplasia type 1, hereditary diffuse gastric cancer, hepatoma, neurofibromatosis type 1, acute myeloid leukemia, T-acute lymphoblastic leukemia, and Ewing sarcoma.

In some embodiments of the methods of the presently disclosed subject matter including inhibiting Alu RNA associated with a cell, the inhibiting Alu RNA comprises increasing levels of a DICER polypeptide in the cell. In some embodiments, increasing levels of a DICER polypeptide comprises overexpressing the DICER polypeptide in the cells. In some embodiments, increasing levels of a DICER polypeptide comprises using a vector comprising a nucleotide encoding the DICER polypeptide. In some embodiments, the vector is a viral vector. In some embodiments, the virus is selected from an adeno-associated virus, a lentivirus, and an adenovirus. In some embodiments, the vector is a plasmid vector. In some embodiments, the nucleotide encoding the DICER polypeptide is selected from SEQ ID NO: 7 and SEQ ID NO: 8. In some embodiments, the DICER polypeptide is selected from SEQ ID NO: 9, 10, 11, 12, 13, 14, 15, 16, 18, and 20. In some embodiments, the DICER polypeptide comprises a functional fragment of the sequence of SEQ ID NO: 9, 18, or 20. In some embodiments, the DICER polypeptide comprises the following amino acid residues of the polypeptide of SEQ ID NO: 9: 605-1922, 605-1912, 1666-1922, 1666-1912, 605-1786 and 1800-1922, 605-1786 and 1800-1912, 1666-1786 and 1800-1922, 1666-1786 and 1800-1912, 1276-1922, 1276-1912, 1276-1786 and 1800-1922, 1276-1786, 800-1912, 1275-1824, or 1276-1824.

In some embodiments of the methods of the presently disclosed subject matter including inhibiting Alu RNA associated with a cell, the inhibiting Alu RNA comprises increasing levels of a DICER polypeptide comprises using DICER mRNA or a functional fragment thereof. In some embodiments, the DICER mRNA has the sequence of SEQ ID NO: 17, 19, or 21. In some embodiments, the DICER mRNA encodes a DICER polypeptide, for example, the DICER polypeptide of SEQ ID NO: 9, 18, or 20, or a functional fragment thereof.

In some embodiments of the methods of the presently disclosed subject matter including inhibiting Alu RNA associated with a cell, the inhibiting Alu RNA comprises administering an oligonucleotide targeting Alu RNA. In some embodiments, the oligonucleotide has a sequence including a sequence selected from SEQ ID NO: 22, 23, 24, 25, and 26. In some embodiments, at least two oligonucleotides are administered. The presently-disclosed subject matter further includes an isolated oligonucleotide that inhibits the expression of Alu RNA, including a sequence selected from SEQ ID NO: 22, 23, 24, 25, and 26 and including about 29 to 100 nucleotides.

In some embodiments of the methods of the presently disclosed subject matter including inhibiting Alu RNA associated with a cell, the inhibiting Alu RNA comprises administering an siRNA targeting Alu RNA. In some embodiments, the siRNA includes a first strand having a sequence selected from SEQ ID NO: 1, 2, 3, 4, 5, and 6. The presently-disclosed subject matter further includes an isolated double-stranded RNA molecule that inhibits expression of Alu RNA, wherein a first strand of the double-stranded RNA comprises a sequence selected from SEQ ID NO: 1, 2, 3, 4, 5, and 6 and including about 19 to 25 nucleotides.

BRIEF DESCRIPTION OF THE DRAWINGS

FIG. 21 7SL RNA is not regulated in geographic atrophy or by inhibition of DICER1 or Alu. a, 7SL RNA abundance was not different in the RPE of human eyes with geographic atrophy (GA) compared to the RPE of normal human eyes without GA (n=8). b, 7SL RNA abundance was not different in human RPE cells transfected with antisense oligonucleotide (as) targeting DICER1 from those transfected with control (Ctrl) as. n=3. c, 7SL RNA abundance was not different in human RPE cells transfected with antisense oligonucleotide (as) targeting Alu from those transfected with control (Ctrl) as. n=3. 7SL RNA abundance, relative to 18S rRNA, was monitored by real-time RT-PCR. NS, not significant by Student t test.

BRIEF DESCRIPTION OF THE SEQUENCE LISTING

Figure 1:
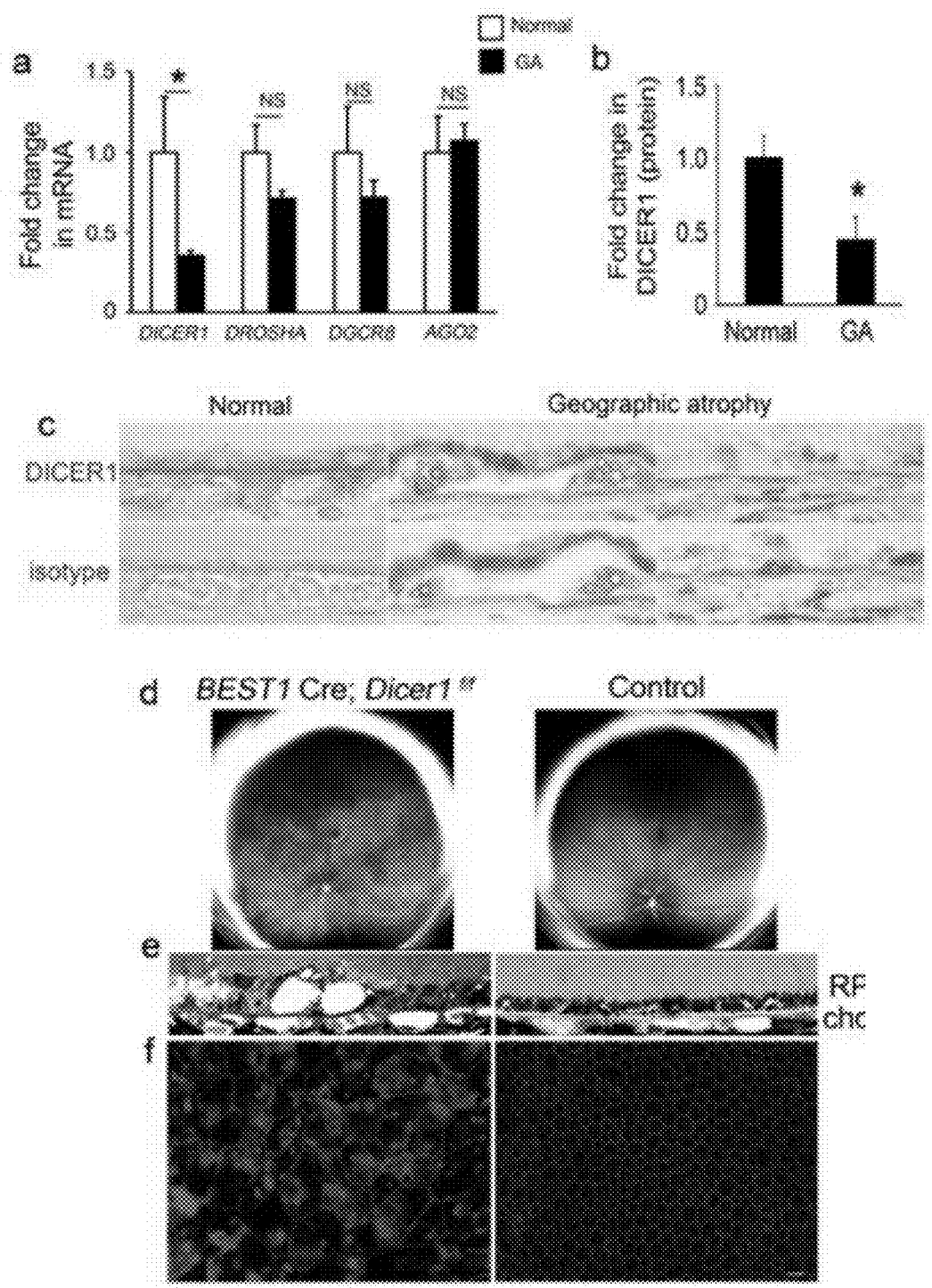
FIG. 1 DICER1 deficit in geographic atrophy induces RPE degeneration. a, DICER1 mRNA abundance, relative to 18S rRNA, monitored by real-time RT-PCR, was lower in the retinal pigmented epithelium (RPE) of human eyes with geographic atrophy (GA; n=10) compared to the RPE of normal human eyes without GA (n=11). P=0.004 by Mann Whitney U test. The abundance of DROSHA, DGCR8, and EIF2C2 (encoding AGO2) mRNA transcripts in the RPE was not significantly different (P>0.11 by Mann Whitney U test) in human eyes with geographic atrophy and control eyes. Transcript abundance quantified by real-time RT-PCR and normalized to 18S rRNA and to control eye levels. n=10-11. b, Relative quantification of DICER1 protein abundance, relative to Vinculin, assessed by Western blotting (Supplementary FIG. 1), was lower in the RPE of human eyes with geographic atrophy (GA; n=4) compared to the RPE of normal human eyes without GA (n=4). P=0.003 by Student t test. c, Immunohistochemistry for DICER1 (blue) showed reduced protein abundance in the RPE of human eyes with GA compared to normal eyes without GA. d, Fundus photographs show extensive RPE degeneration in BEST1 Cre; Dicer1$^{f/f}$ mice but not in littermate control mice. e, Toluidine blue-stained sections show marked RPE degeneration in BEST1 Cre; Dicer1$^{f/f}$ mice compared to normal RPE architecture in control mice. Arrowheads point to basal surface of RPE. f, Flat mounts of the RPE and choroid stained with antibodies against zonula occludens-1 (ZO-1; red) show marked disruption of the RPE monolayer architecture in BEST1 Cre; Dicer$^{f/f}$ mice compared to the uniformly tesselated RPE layer in littermate control mice. g, Fundus photographs show RPE degeneration in Dicer1$^{f/f}$ mice following subretinal injection of AAV1-BEST1-Cre but not AAV1-BEST1-GFP. h, Toluidine blue-stained sections show marked degeneration of RPE and photoreceptor outer segments in Dicer1$^{f/f}$ mice following subretinal injection of AAV1-BEST1-Cre but not AAV1-BEST1-GFP. i, Flat mounts show marked increase in RPE cell size and distortion of RPE cell shape in Dicer1$^{f/f}$ mice following subretinal injection of AAV1-BEST1-Cre but not AAV1-BEST1-GFP. RPE cell borders outlined by ZO-1 staining (red). Nuclei stained blue with Hoechst 33342. Representative images shown. n=16-32 (d-f); 10-12 (g-i). Scale bars, (c,e,h), 10 μm; (f,i) 20 μm. j, Transfection of adenoviral vector coding for Cre recombinase (Ad-Cre) in RPE cells isolated from Dicer1$^{f/f}$ mice resulted in loss of cell viability, as monitored by MTS assay at 7 days, compared to transfection with Ad-Null or untreated (no Tx) cells. k, Transfection of antisense oligonucleotide (as) targeting DICER1 into human RPE cells resulted in increasing loss of cell viability over time compared to scrambled sequence antisense (Ctrl as)-treated cells. n=6-8.

SEQ ID NO: 1 is an embodiment of a first strand of an siRNA provided in accordance with the presently-disclosed subject matter.

SEQ ID NO: 2 is an embodiment of a first strand of an siRNA provided in accordance with the presently-disclosed subject matter.

SEQ ID NO: 3 is an embodiment of a first strand of an siRNA provided in accordance with the presently-disclosed subject matter.

SEQ ID NO: 4 is an embodiment of a first strand of an siRNA provided in accordance with the presently-disclosed subject matter.

SEQ ID NO: 5 is an embodiment of a first strand of an siRNA provided in accordance with the presently-disclosed subject matter.

SEQ ID NO: 6 is an embodiment of a first strand of an siRNA provided in accordance with the presently-disclosed subject matter.

SEQ ID NO: 7 is nucleotide sequence encoding a human DICER polypeptide, including all untranslated regions (GenBank Accession Number NM_177438).

SEQ ID NO: 8 is a cDNA sequence encoding a human DICER polypeptide.

SEQ ID NO: 9 is a polypeptide sequence for a human DICER polypeptide.

SEQ ID NO: 10 is a polypeptide sequence for a human DICER polypeptide, including residues 1276-1922 of SEQ ID NO: 9.

SEQ ID NO: 11 is a polypeptide sequence for a human DICER polypeptide, including residues 605-1922 of SEQ ID NO: 9.

SEQ ID NO: 12 is a polypeptide sequence for a human DICER polypeptide, including residues 1666-1922 of SEQ ID NO: 9.

SEQ ID NO: 13 is a polypeptide sequence for a human DICER polypeptide, including residues 1666-1912 of SEQ ID NO: 9.

SEQ ID NO: 14 is a polypeptide sequence for a human DICER polypeptide, including residues 1666-1786 and 1800-1912 of SEQ ID NO: 9.

SEQ ID NO: 15 is a polypeptide sequence for a human DICER polypeptide, including residues 1275-1824 of SEQ ID NO: 9.

SEQ ID NO: 16 is a polypeptide sequence for a human DICER polypeptide, including residues 1276-1824 of SEQ ID NO: 9.

SEQ ID NO: 17 is an mRNA sequence encoding a human DICER polypeptide.

SEQ ID NO: 18 is a polypeptide sequence for a *Schizosaccharomyces pombe* DICER polypeptide.

SEQ ID NO: 19 is an mRNA sequence encoding a *Schizosaccharomyces pombe* DICER polypeptide.

SEQ ID NO: 20 is a polypeptide sequence for a *Giardia lamblia* DICER polypeptide.

SEQ ID NO: 21 is an mRNA sequence encoding a *Giardia lamblia* DICER polypeptide.

SEQ ID NO: 22 is an embodiment of an antisense oligonucleotide sequence provided in accordance with the presently-disclosed subject matter.

SEQ ID NO: 23 is an embodiment of an antisense oligonucleotide sequence provided in accordance with the presently-disclosed subject matter.

SEQ ID NO: 24 is an embodiment of an antisense oligonucleotide sequence provided in accordance with the presently-disclosed subject matter.

SEQ ID NO: 25 is an embodiment of an antisense oligonucleotide sequence provided in accordance with the presently-disclosed subject matter.

SEQ ID NO: 26 is an embodiment of an antisense oligonucleotide sequence provided in accordance with the presently-disclosed subject matter.

DESCRIPTION OF EXEMPLARY EMBODIMENTS

The presently-disclosed subject matter includes methods for identifying Alu RNA inhibitors, and methods and compositions for inhibiting Alu RNA and therapeutic uses thereof.

As disclosed herein, Alu RNA (including Alu repeat RNA in human cells and B1 and B2, Alu-like element repeat RNAs) increases are associated with cells that are associated with certain conditions of interest. For example, Alu RNA increase is associated with the retinal pigment epithelium (RPE) cells of eyes with geographic atrophy. This increase of Alu RNA induces the death of RPE cells. Methods and compositions disclosed herein can protect a cell from Alu RNA-triggered cell death, thereby treating conditions associated with such cell death.

The presently-disclosed subject matter further includes methods useful for identifying an Alu RNA inhibitor and uses of such inhibitors, including therapeutic and protective uses. In some embodiments, the method makes use of a cultured cell wherein Alu RNA is upregulated. Candidate compounds can be screened using the cultured cell to determine efficacy as antagonists of Alu RNA. Candidate compounds include, for example, small molecules, biologics, and combinations thereof, such as compositions including multiple compounds. The term small molecules is inclusive of traditional pharmaceutical compounds. The term biologics is inclusive of polypeptides and nucleotides.

In some embodiments, the screening method includes providing a cell in culture wherein Alu RNA is upregulated; and contacting a candidate compound with the cell. The method can further include identifying a change in Alu RNA. For example, a measurable change in Alu RNA levels can be indicative of efficacy associated with the candidate compound. In some embodiments, wherein the change in the Alu RNA is a measurable decrease in Alu RNA, the change is an indication that the candidate compound is an Alu RNA inhibitor. Such Alu RNA inhibitors can have utility for therapeutic applications as disclosed herein.

In some embodiments, the Alu RNA can be upregulated by decreasing native levels of DICER polypeptides in the cell using methods known to those skilled in the art. In some embodiments, the Alu RNA associated with cultured cell can be upregulated by using heat shock stress using methods known to those skilled in the art. In some embodiments, the cultured cell is an RPE cell.

Methods and compositions of the presently-disclosed subject matter for treating a condition of interest include inhibiting Alu RNA associated with a cell, such as a cell of a subject in need of treatment. Examples of conditions of interest include, but are not limited to: geographic atrophy, dry age-related macular degeneration, thallasemia, familial hypercholesterolemia, Dent's disease, acute intermittent porphyria, anterior pituitary aplasia, Apert syndrome, Hemophilia A, Hemophilia B, glycerol kinase deficiency, autoimmune lymphoproliferative syndrome, X-linked agammaglobulinemia, X-linked severe combined immunodeficiency, adrenoleukodystrophy, Menkes disease, hyperimmunoglobulin M syndrome, retinal blinding, Type 1 antithrombin deficiency, Muckle-Wells syndrome, hypocalciuric hypercalcemia and hyperparathyroidism, cholinesterase deficiency, hereditary desmoid disease, chronic hemolytic anemia, cystic fibrosis, branchio-oto-renal syndrome, lipoprotein lipase deficiency, CHARGE syndrome, Walker Warburg syndrome, Complement deficiency, Mucolipidosis type II, Breast cancer, ovarian cancer, prostate cancer, von Hippel Lindau disease, Hereditary non-polyposis colorectal cancer, multiple endocrine neoplasia type 1, hereditary diffuse gastric cancer, hepatoma, neurofibromatosis type 1, acute myeloid leukemia, T-acute lymphoblastic leukemia, and Ewing sarcoma.

As used herein, the terms treatment or treating relate to any treatment of a condition of interest, including but not limited to prophylactic treatment and therapeutic treatment. As such, the terms treatment or treating include, but are not limited to: preventing a condition of interest or the development of a condition of interest; inhibiting the progression of a condition of interest; arresting or preventing the development of a condition of interest; reducing the severity of a condition of interest; ameliorating or relieving symptoms associated with a condition of interest; and causing a regression of the condition of interest or one or more of the symptoms associated with the condition of interest.

As used herein, the term "subject" refers to a target of treatment. The subject of the herein disclosed methods can be a vertebrate, such as a mammal, a fish, a bird, a reptile, or an amphibian. Thus, the subject of the herein disclosed methods can be a human or non human. Thus, veterinary therapeutic uses are provided in accordance with the presently disclosed subject matter.

In some embodiments, the condition of interest is geographic atrophy and the cell is an RPE cell. In this regard, a subject having age-related macular degeneration can be treated using methods and compositions as disclosed herein.

As will be understood by those skilled in the art upon studying this application, inhibition of Alu RNA associated a cell can be achieved in a number of manners. For example, in some embodiments, inhibiting Alu RNA associated with a cell comprises increasing levels of a DICER polypeptide in the cell, for example, by overexpressing the DICER polypeptide in the cell. For another example, a DICER mRNA could be used. For another example, in some embodiments, inhibiting Alu RNA associated with a cell comprises administering an oligonucleotide or a small RNA molecule targeting the Alu RNA. As used herein, inhibiting Alu RNA associated with a cell refers to a reduction in the levels of Alu RNA inside and/or outside the cell in the extracellular space.

The term DICER Polypeptide refers to polypeptides known to those of ordinary skill in the art as DICER, including, but not limited to polypeptides comprising the sequences of SEQ ID NO: 9, 18, and 20, and functional fragments or functional variants thereof.

It is noted that one of ordinary skill in the art will be able to readily obtain publicly-available information related to DICER, including relevant nucleotide and polypeptide sequences included in publicly-accessible databases, such as GENBANK®. Some of the sequences disclosed herein are cross-referenced to GENBANK® accession numbers, e.g., GenBank Accession Number NM_177438. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein. Unless otherwise indicated or apparent, the references to the GENBANK® database are references to the most recent version of the database as of the filing date of this application.

The terms "polypeptide", "protein", and "peptide", which are used interchangeably herein, refer to a polymer of the 20 protein amino acids, or amino acid analogs, regardless of its size. The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus (e.g., removing residues 1-604, 1-1274, 1-1275, or 1-1665 of SEQ ID NO: 9) or carboxy-terminus of the reference polypeptide (e.g., removing residues 1825-1922, or 1913-1922 of SEQ ID NO: 9), from interal portions of the reference polypeptide (e.g., removing residues 1787-1799 of SEQ ID NO: 9), or a combination thereof.

A fragment can also be a "functional fragment," in which case the fragment retains some or all of the activity of the reference polypeptide as described herein. For example, in some embodiments, a functional fragment of the polypeptide of SEQ ID NO: 9 can retain some or all of the ability of the polypeptide of SEQ ID NO: 9 to degrade Alu RNA. Examples of functional fragments of the polypeptide of SEQ ID NO: 9 include the polypeptides of SEQ ID NOS: 10-16. Additional examples include, but are not limited to, the polypeptide of SEQ ID NO: 9, including the following residues: 605-1922, 605-1912, 1666-1922, 1666-1912, 605-1786 and 1800-1922, 605-1786 and 1800-1912, 1666-1786 and 1800-1922, 1666-1786 and 1800-1912, 1276-1922, 1276-1912, 1276-1786 and 1800-1922, 1276-1786 and 1800-1912, 1275-1824, or 1276-1824.

The terms "modified amino acid", "modified polypeptide", and "variant" refer to an amino acid sequence that is different from the reference polypeptide by one or more amino acids, e.g., one or more amino acid substitutions. A variant of a reference polypeptide also refers to a variant of a fragment of the reference polypeptide, for example, a fragment wherein one or more amino acid substitutions have been made relative to the reference polypeptide. A variant can also be a "functional variant," in which the variant retains some or all of the activity of the reference protein as described herein. The term functional variant includes a functional variant of a functional fragment of a reference polypeptide.

In some embodiments, the DICER Polypeptide can be overexpressed in the cell using a vector comprising a nucleotide encoding the DICER polypeptide, for example, the nucleotide of SEQ ID NOS: 7 or 8, or appropriate fragment thereof, or a nucleotide encoding a DICER Polypeptide, for example, a nucleotide encoding SEQ ID NOS: 9, 10, 11, 12, 13, 14, 15, 16, 18, or 20. As will be recognized by those skilled in the art, the vector can be a plasmid vector or a viral vector (e.g., adeno-associated virus, lentivirus, adenovirus.

As noted above, in some embodiments, inhibiting Alu RNA comprises use of a DICER mRNA. In some embodiments, a functional fragment of a DICER mRNA could be used. In some embodiments, a DICER mRNA having the sequence of SEQ ID NOS: 17, 19, or 21, or a functional fragment thereof could be used. In some embodiments an mRNA encoding a DICER Polypeptide could be used, for example, an mRNA encoding SEQ ID NOS: 9, 10, 11, 12, 13, 14, 15, 16, 18, or 20.

As noted above, in some embodiments, inhibiting Alu RNA comprises administering an oligonucleotide or a small RNA molecule targeting the Alu RNA. Such nucleotides can target and degrade Alu RNA.

As such, in some embodiments, a method is provided including administering an oligonucleotide targeting Alu RNA. Examples of oligonucleotides targeting Alu RNA include those set forth in SEQ ID NOS: 22-26. In some embodiments, more than one oligonucleotide is administered.

In some embodiments, a method is provided including administering an siRNA targeting Alu RNA. Examples of siRNAs for targeting Alu RNA include those set forth in SEQ ID NOS: 1-6.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples.

The following examples may include compilations of data that are representative of data gathered at various times during the course of development and experimentation related to the present invention.

EXAMPLES

DICER1 Reduction in Geographic Atrophy

Figure 6:
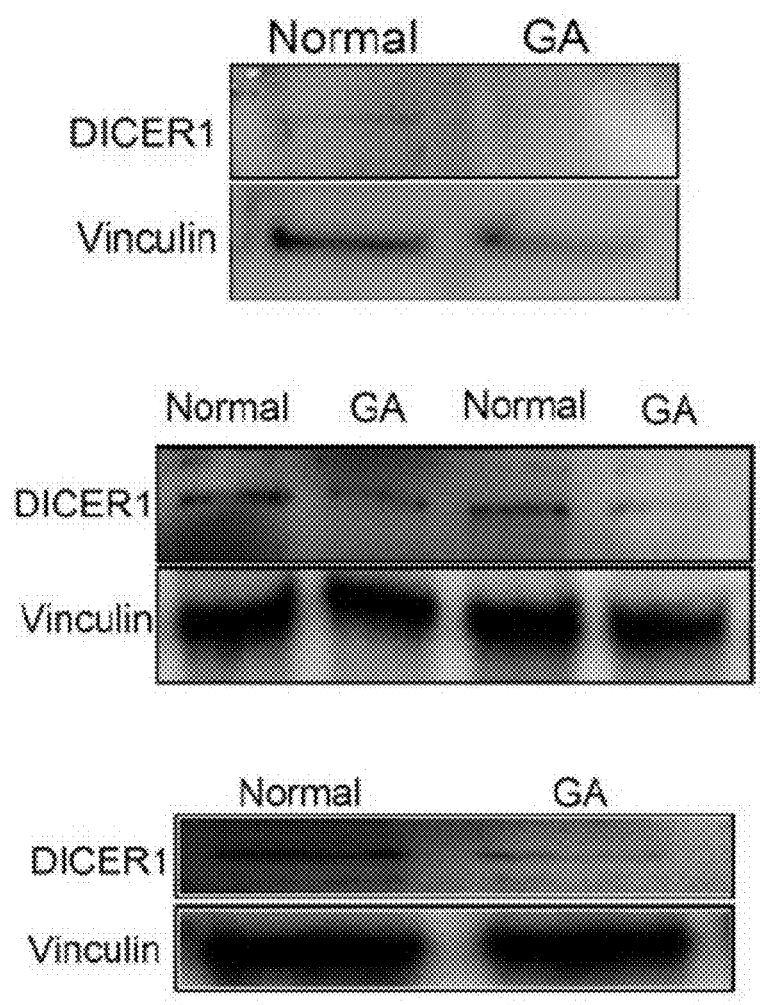
FIG. 6 DICER1 levels in RPE are reduced in geographic atrophy. Western blots of macular RPE lysates from individual human donor eyes show that DICER1 protein abundance, normalized to the levels of the housekeeping protein Vinculin, are reduced in geographic atrophy (GA) compared to age-similar control human eyes without age-related macular degeneration.
Figure 7:
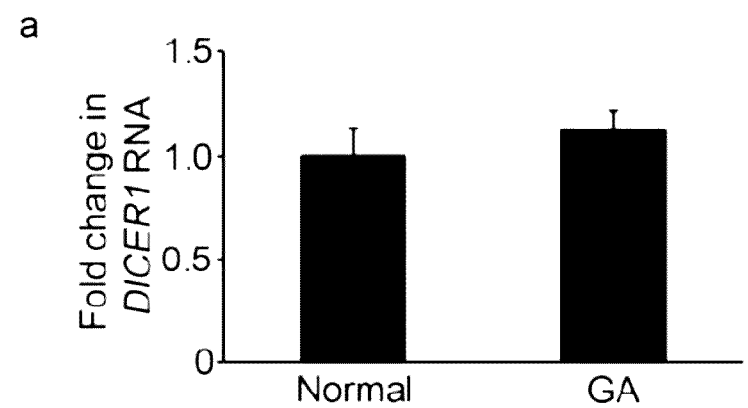
FIG. 7 DICER1 levels in neural retina are unchanged in geographic atrophy. a, DICER1 mRNA abundance in the neural retina, as monitored by real-time RT-PCR, was not significantly different (P>0.05 by Mann Whitney U test) between normal human retinas and those with geographic atrophy. Levels normalized to 18S rRNA abundance and to normal retinas. n=7. b-e, DICER1 protein immunolocalization in the neural retina was not different between human eyes with geographic atrophy (b) and normal (d) eyes. Specificity of DICER1 staining was confirmed by absence of reaction production with isotype control antibody (c,e). Representative images shown. n=8. Scale bars (20 μm, b-e).

In human donor eyes with geographic atrophy (n=10), the present inventors found using real-time RT-PCR that DICER1 mRNA abundance was reduced in the macular RPE by 65±3% (mean±SEM; P=0.0036; Mann-Whitney U test) compared to age-similar human eyes without geographic atrophy (n=11) (FIG. 1a). Because the best understood function of DICER1 is miRNA generation[3], the present inventors measured the expression of other enzymes involved in miRNA biogenesis. The abundance of the genes encoding DROSHA or the double stranded RNA (dsRNA) binding protein DGCR8, which form a complex that processes pri-miRNAs into pre-miRNAs[5], was not reduced in the RPE of human eyes with geographic atrophy. There was also no reduction in the expression of the gene encoding Argonaute 2 (AGO2, encoded by EIF2C2), the core component of the miRNA effector complex[6,7], in the RPE of human eyes with geographic atrophy. Corroborating the mRNA data, the present inventors observed a marked reduction of DICER1 protein expression in the RPE layer of human eyes with geographic atrophy compared to controls in Western blot (FIG. 1b and FIG. 6) and immunohistochemistry analyses (FIG. 1c). Interestingly, DICER1 mRNA and protein abundance in the adjacent neural retina was similar between the two groups (FIG. 7).

Figure 8:
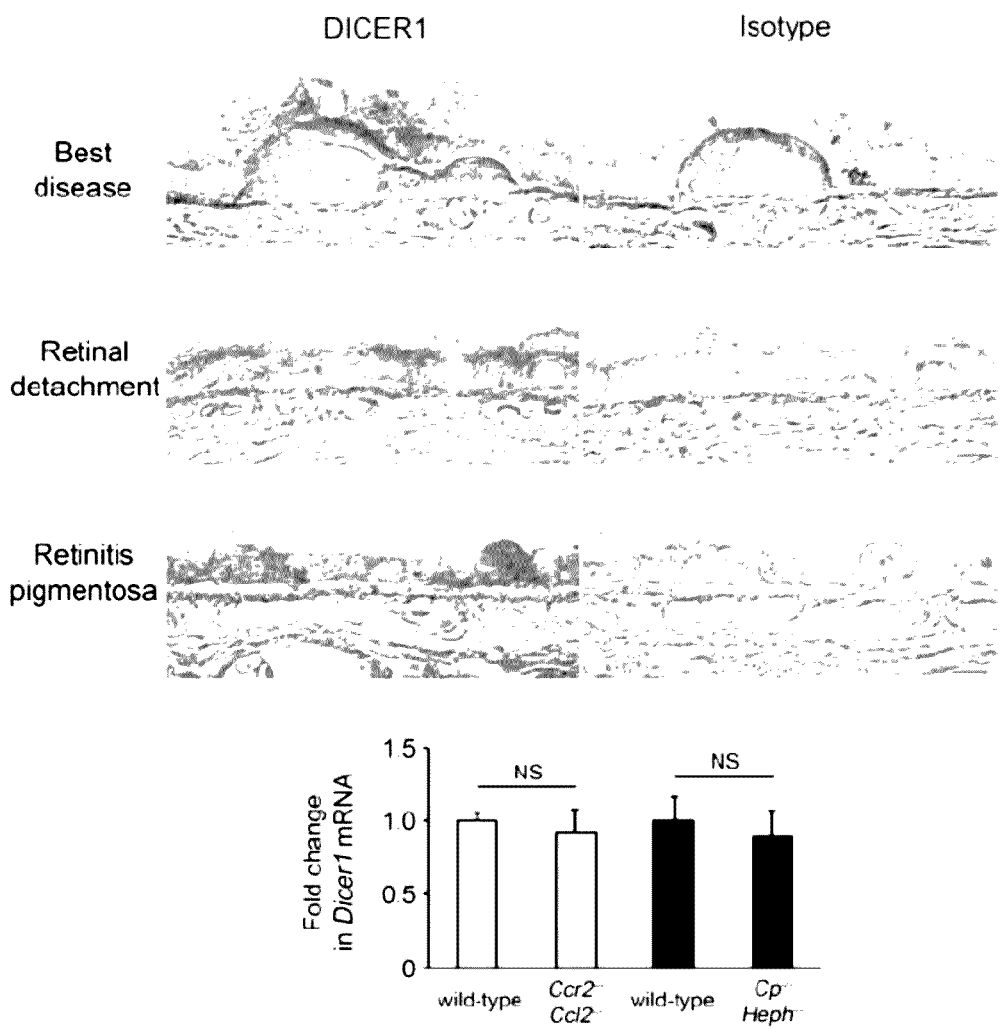
FIG. 8 DICER1 is not generically downregulated in retinal diseases. Immunolocalization studies revealed abundant DICER1 protein expression (blue, left column) in the RPE in the eye of an 85-year-old man with Best disease (vitelliform macular dystrophy), a 68-year-old man with retinal detachment secondary to choroidal melanoma, and a 72-year-old woman with retinitis pigmentosa. Specificity of DICER1 staining was confirmed by absence of reaction production with isotype control antibody (right column). Representative images shown. n=13. Scale bars (10 μm). Dicer1 mRNA expression in the RPE was not significantly (NS) different in Ccl2$^{-/-}$ Ccr2$^{-/-}$ mice or Cp$^{-/-}$ Heph$^{-/-}$ mice compared to their background strains. Transcript abundance quantified by real-time RT-PCR and normalized to 18S rRNA and to control eye levels. n=6. NS, not significant.

Because DICER1 downregulation is observed in some cell types in culture conditions in response to various chemical stresses[8], the present inventors wondered whether DICER1 reduction in geographic atrophy might be a common downstream pathway in dying retina. DICER1 protein levels were not reduced in the RPE of human eyes with several other retinal disorders such as vitelliform macular dystrophy, retinitis pigmentosa, or retinal detachment (FIG. 8). Also, Dicer1 mRNA abundance in the RPE in two animal models of retinal degeneration—Ccl2$^{-/-}$ Ccr2$^{-/-}$ (refs. 9,10) and Cp$^{-/-}$ Heph$^{-/-}$ mice[11]—was unchanged compared to their background strains (FIG. 8). Gene expression studies in numerous other mouse models of retinal degeneration also have not reported modulation of Dicer1 (Supplemental Notes). These data argue that DICER1 depletion in the RPE of eyes with geographic atrophy is not a generic response of damaged or dying retinal cells in vivo.

DICER1 Depletion Induces RPE Degeneration

Figure 9:
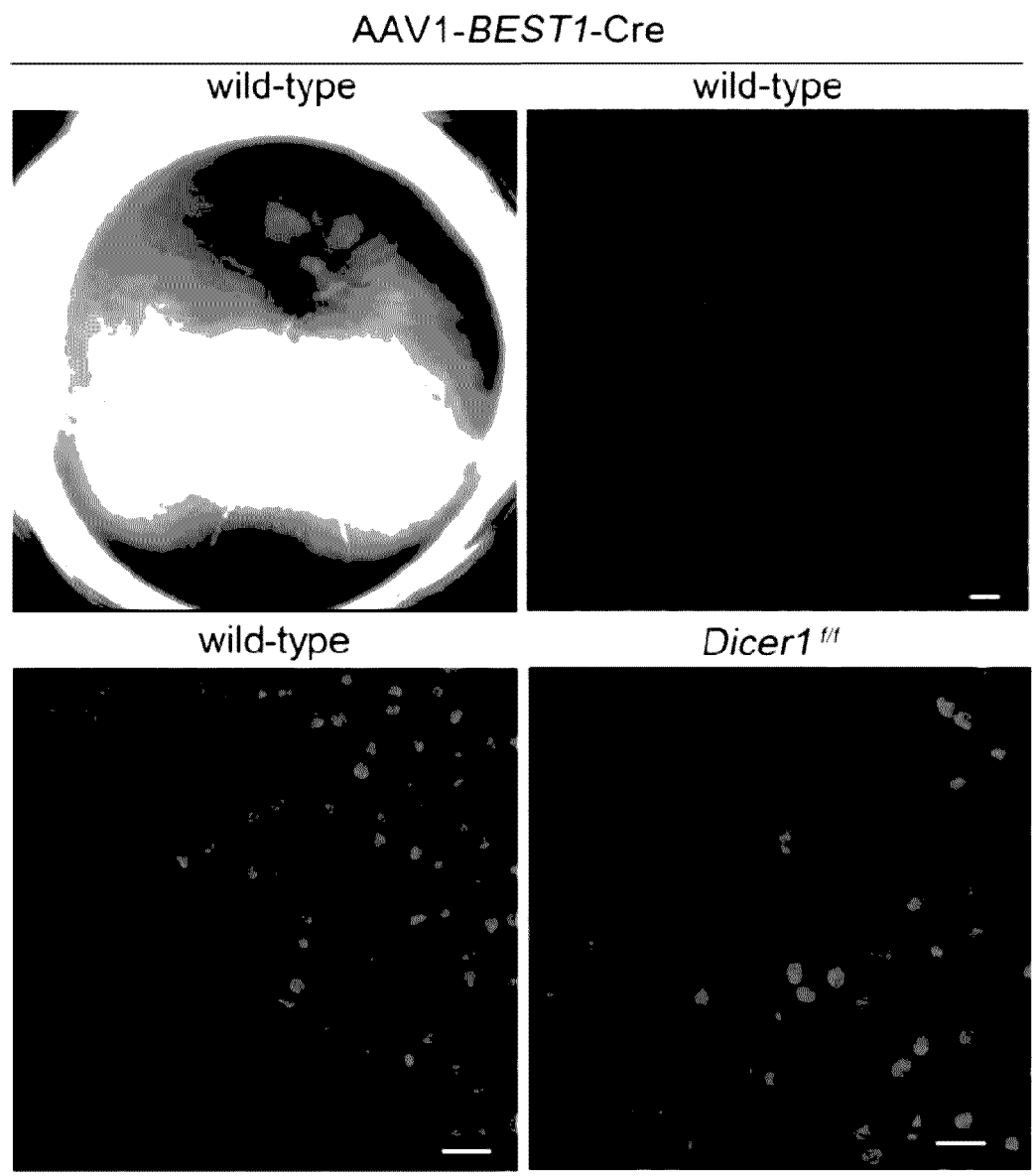
FIG. 9 Cre recombinase expression does not induce retinal pigmented epithelium (RPE) degeneration. Subretinal administration of adeno-associated viral vector coding for Cre recombinase directed by the BEST1 promoter (AAV1-BEST1-Cre) in wild-type mice did not induce retinal toxicity that was evident on fundus photography (top left) and did not disrupt the tiling pattern of the RPE monolayer (top right). Circular flash artifact is seen in the centre of the fundus photograph. RPE cell borders delineated by staining with anti-ZO-1 antibody (red) and nuclei stained by Hoechst 33342 (blue). RPE flat mounts show successful Cre recombinase expression (red) following subretinal injection of AAV1-BEST1-Cre in wild-type (bottom left) and Dicer1$^{f/f}$ (bottom right) mouse eyes. Representative images shown. n=8-10. Scale bar (20 μm).
Figure 10:
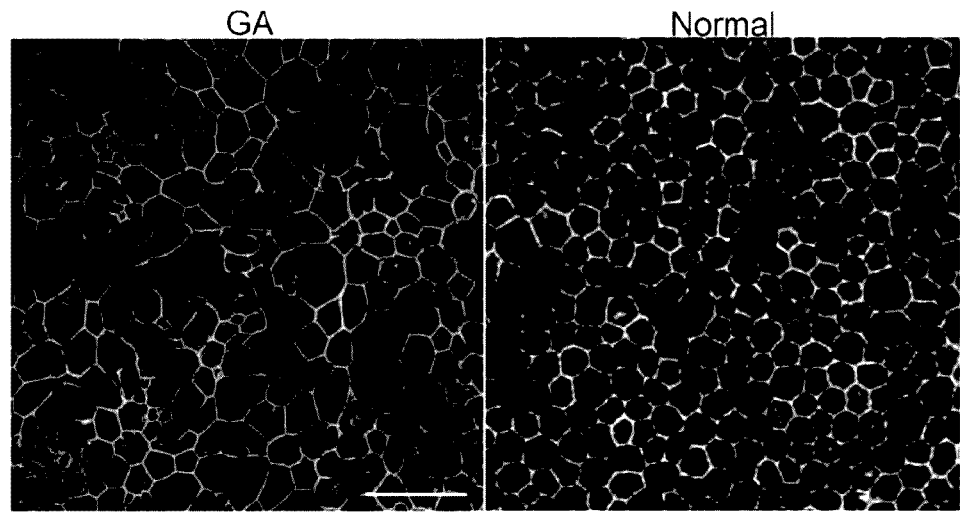
FIG. 10 Retinal pigmented epithelium (RPE) cell dysmorphology in human age-related macular degeneration eye with atrophy. In contrast to the well tessellated RPE cell monolayer observed in a normal human eye (right), marked changes in RPE cell size and shape are observed in the human eye with geographic atrophy (left). These changes resemble those observed in eyes of mice wherein Dicer1 has been depleted in the RPE. RPE cell borders delineated by staining with anti-ZO-1 antibody (green) and nuclei stained by propidium iodide (red). Representative image shown. n=8. Scale bar, 50 μm.

To determine the functional consequence of reduced DICER1 levels, the present inventors conditionally ablated Dicer1 in mouse RPE cells by interbreeding "foxed" Dicer1 mice[12] (Dicer1$^{f/f}$) with BEST1 Cre mice[13], which express Cre recombinase under the control of the RPE cell-specific BEST1 promoter. BEST1 Cre; Dicer1$^{f/f}$ mice uniformly exhibited dramatic RPE cell degeneration (FIG. 1d-f) that was evident by the time of weaning. None of the littermate controls exhibited similar pathology. The present inventors also deleted Dicer1 in adult mouse RPE by subretinal injection of an adeno-associated viral vector coding for Cre recombinase under the control of the BEST1 promoter[14] (AAV1-BEST1-Cre) in Dicer1$^{f/f}$ mice (FIG. 9). These eyes uniformly displayed RPE cell degeneration at 28 days after injection similar to that observed in mice depleted of Dicer1 expression during development (FIG. 1g-i; FIG. 9). In contrast, neither the contralateral eyes of Dicer1$^{f/f}$ mice that underwent subretinal injection of AAV1-BEST1-GFP nor the eyes of wild-type mice injected with subretinal AAV1-BEST1-Cre developed RPE cell degeneration (FIG. 1g-i and FIG. 9). The RPE cell dysmorphology in mice depleted of Dicer1 expression resembled that observed in the eyes of humans with RPE atrophy due to AMD (FIG. 10). When cultured RPE cells isolated from Dicer1$^{f/f}$ mice were infected with an adenoviral vector coding for Cre recombinase (Ad-Cre), the present inventors observed a reduction of cell viability compared to infection with Ad-Null (FIG. 1j). Similarly, antisense oligonucleotide mediated knockdown of DICER1 in human RPE cells resulted in increasing cell death over time (FIG. 1k). Collectively, these data support the hypothesis that DICER1 dysregulation is involved in the pathogenesis of geographic atrophy.

DICER1 Depletion Phenotype not Due to miRNA Dysregulation

Figure 11:
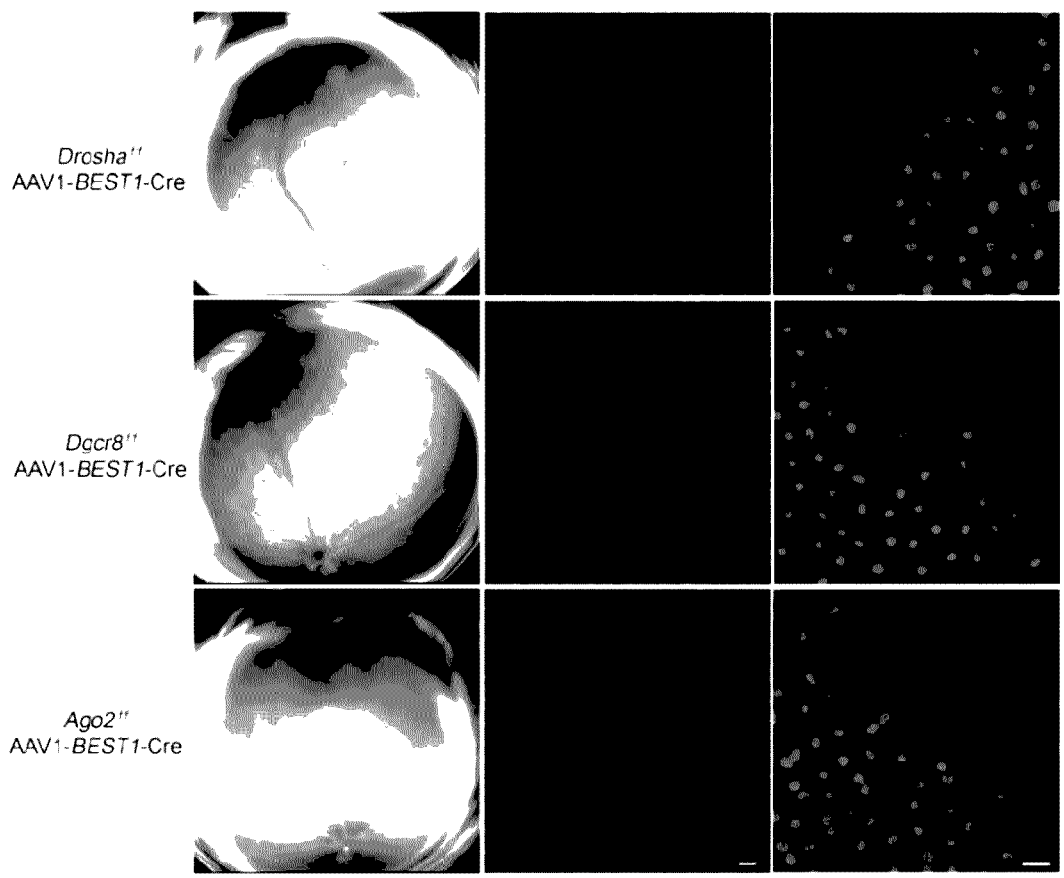
FIG. 11 Conditional ablation of Drosha, Dgcr8, or Ago2 in the retinal pigmented epithelium (RPE) does not induce degeneration as seen in Dicer1-ablated mice. Fundus photographs (left column) show no significant degeneration following subretinal injection of AAV-BEST1-Cre in mice "foxed" for Drosha, DGCR8, or Ago2. Circular flash artifacts are seen near the centre of the fundus photographs. Injection site wound appears white in the fundus photograph of the Ago2$^{f/f}$ eye. RPE flat mounts (middle column) stained with anti-ZO-1 antibody (red) and Hoechst 33342 (blue) show normal tiling pattern of RPE with no gross disturbance of cell size or shape. RPE flat mounts (right column) stained with anti-Cre recombinase antibody (red) and Hoechst 33342 (blue) shows successful Cre expression in these mice eyes. Representative images shown. n=8-12. Scale bar (20 μm).
Figure 12:
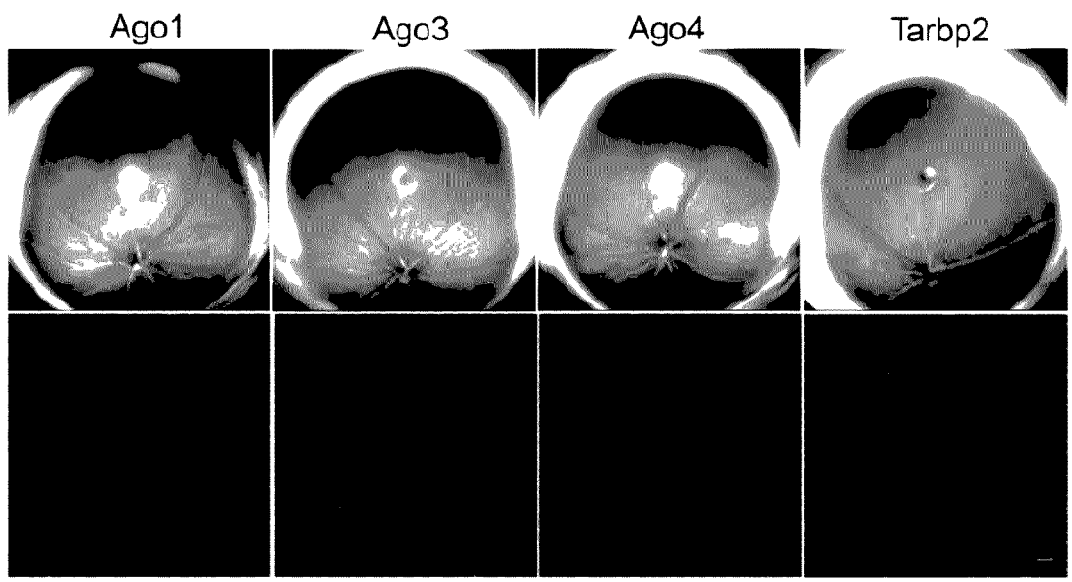
FIG. 12 Deficiency of Ago1, Ago3, Ago4, or Tarbp2 does not induce RPE degeneration. Mice deficient in Ago1 Ago3 Ago4, or Tarbp2 have normal retinal appearance on fundus photography (top row) and normal RPE monolayer architecture on ZO-1 stained (red) flat mounts (bottom row). Circular flash artifact is seen in the centre of the fundus photographs. Scale bar, 20 μm.

The present inventors tested whether depletion of other enzymes involved in miRNA biogenesis also would induce RPE degeneration. Subretinal injection of AAV1-BEST1-Cre in Drosha$^{f/f}$ (ref. 13), Dgcr8$^{f/f}$ (refs. 15,16), or $^{10}$Ago2$^{f/f}$ mice[17] did not result in the dramatic RPE cell damage that was evident in similarly treated Dicer$^{f/f}$ mice (FIG. 11). These data suggest that miRNA imbalances are not responsible for RPE degeneration induced by DICER1 depletion. However, the present inventors and others have reported[18,19] that a small subset (approximately 7%) of mammalian miRNAs is generated by Dicer1 independent of Drosha and Dgcr8. There is also debate as to whether Ago2 is essential for miRNA function: Ago2 deficiency leads to global reduction of miRNA expression uncompensated by other three Ago proteins in mice[17,20] and in mouse embryonic fibroblasts and oocytes[21,22], yet functional redundancy among Argonaute proteins has been reported in mouse embryonic stem cells[23]. The present inventors found no RPE degeneration in mice deficient in Ago1, Ago3, or Ago4 (FIG. 12). TRBP (the human immunodeficiency virus transactivating response RNA-binding protein encoded by Tarbp2) recruits DICER1 to the four Argonaute proteins to enable miRNA processing and RNA silencing (ref 24 and R. Shiekhattar, personal communication); Tarbp2$^{-/-}$ mice too had no RPE degeneration (FIG. 12). These data suggest that RPE degeneration induced by Dicer1 ablation involves a mechanism specific to Dicer1 and not to miRNA machinery in general.

Figure 13:
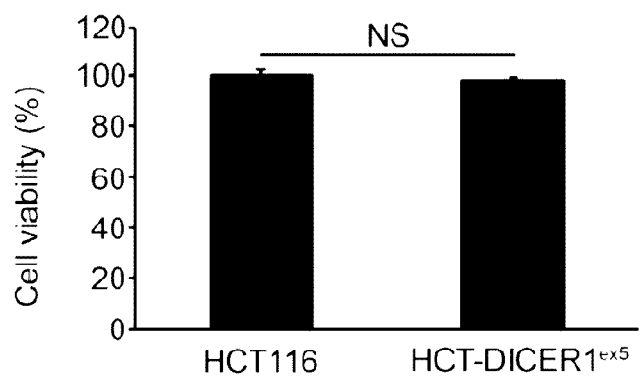
FIG. 13 DICER1 mutant cells impaired in miRNA biogenesis do not have compromised cell viability. There was no difference in baseline cell viability between HCT-DICER1$^{ex5}$ cells, which are impaired in miRNA biogenesis[1], and parent HCT116 cells over 3 days of analysis of cell proliferation. n=3. NS, not significant.

To further investigate whether miRNA imbalances might contribute to the phenotype observed in the setting of DICER1 depletion, the present inventors studied human HCT116 colon cancer cells in which the helicase domain in exon 5 of DICER1 was disrupted. Despite the impairment of miRNA biogenesis in these HCT-DICER1$^{ex5}$ cells[25], there was no difference between HCT-DICER1$^{ex5}$ and parent HCT116 cells in baseline cell viability (FIG. 13). Collectively, these findings suggest that the principal biological effect of DICER1 deficit contributing to the development of geographic atrophy is not miRNA dysregulation. The findings do not, however, exclude the possibility that miRNA dysregulation could promote geographic atrophy through other pathways.

Alu RNA Accumulation in Geographic Atrophy

Figure 2:
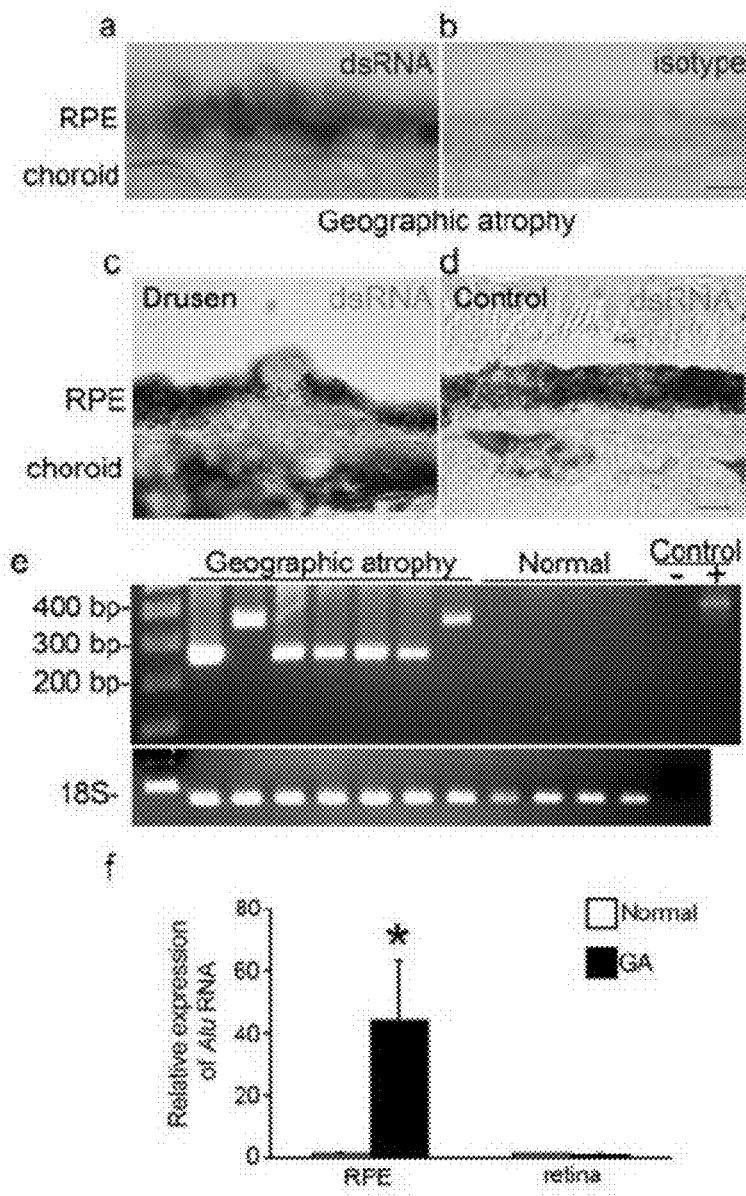
FIG. 2 Alu RNA accumulation in geographic atrophy triggered by DICER reduction. a, Immunohistochemistry with anti-double stranded RNA (dsRNA) antibody (J2) shows abundant accumulation of dsRNA (blue staining) in the retinal pigmented epithelium (RPE) of a human eye with geographic atrophy. b, Lack of immunolabeling with an isotype antibody in the same eye with geographic atrophy confirms specificity of dsRNA staining c,d, dsRNA is immunolocalized (blue staining) in the RPE and sub-RPE deposits (drusen) of a human eye with geographic atrophy (c) but not in the RPE of a normal (control) eye (d). Scale bars, (a-d), 10 μm. n=10 (a-d) e, PCR amplification of dsRNA immunoprecipitated by J2 antibody from RPE isolates from human eyes with geographic atrophy and normal eyes yielded amplicons with sequence homology to Alu sequences (Supplementary FIG. S7) in eyes with geographic atrophy but not in normal eyes. Water negative control (−) showed no amplification and positive control (+) recombinant dsRNA showed predicted amplicon. f, Alu RNA abundance, relative to 18S rRNA, monitored by real-time RT-PCR, was higher in the RPE of human eyes with geographic atrophy compared to the RPE of normal human eyes without GA (n=7). P<0.05 by Student t test. There was no significant difference in Alu RNA abundance in the neural retina of these two patient groups. Values normalized to relative abundance in normal eyes.

Because miRNA perturbations could not be implicated, the present inventors speculated that impaired processing of other dsRNAs might be involved. Using an antibody[26,27] that recognizes long dsRNA (J2), the present inventors detected abundant dsRNA immunoreactivity in the macular RPE of human eyes with geographic atrophy (n=10; FIG. 2a-c). In contrast, no J2 immunoreactivity was observed in eyes without geographic atrophy (n=10; FIG. 2d). To identify this dsRNA species, the present inventors immunoprecipitated RPE lysates with J2 antibody and then sequenced the dsRNA using a T4 RNA ligase-aided, adaptor-based PCR amplification strategy. Interestingly, approximately 300-nt long dsRNA species were found in the macular RPE of human eyes with geographic atrophy (12/12) but not in eyes without geographic atrophy (0/18) (P=1.2×10$^{-8}$ by Fisher's exact test) (FIG. 2e).

Figure 14:
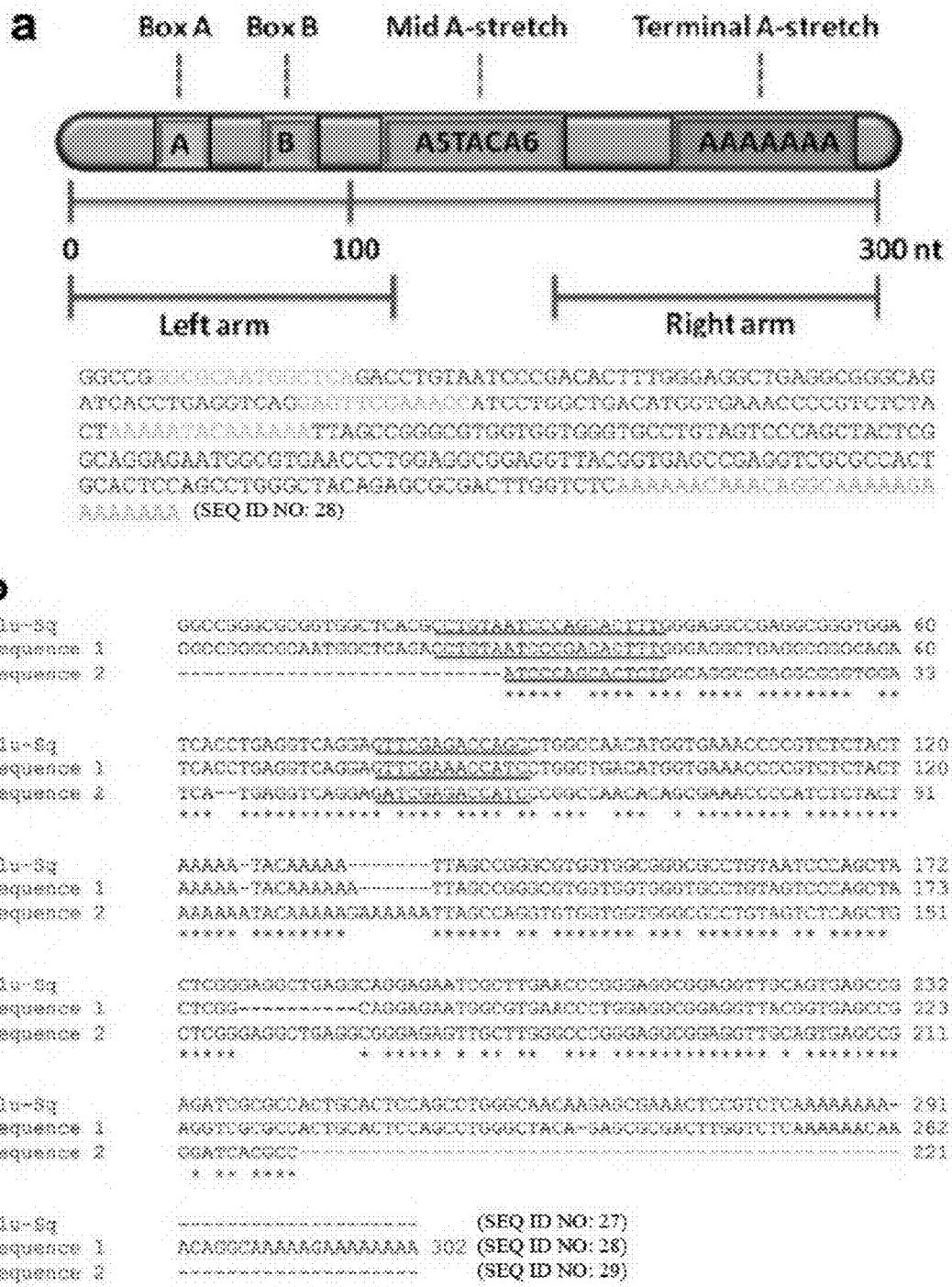
FIG. 14 Human geographic atrophy eye retinal pigmented epithelia contain Alu RNA sequences. a, Top: Typical Alu element with conserved structural regions (adapted from ref. 2). The left arm consists of RNA polymerase III binding sites (Box A and Box B). The right arm occasionally contains a terminal poly A tail that may be interspersed with non-A bases. The 5' and 3' regions of the Alu element are linked by a mid-stretch A-rich sequence. Bottom: Representative Alu cDNA (Sequence 1). The conserved regions mentioned above are highlighted and correspond to the coloured boxes in the top figure. b, Alignment of Alu cDNA Sequences 1 and 2 isolated from human eyes with geographic atrophy to Alu Sq consensus sequence. These sequences contain the highly conserved 5' Alu consensus elements (5' characteristic Alu region—blue; RNA polymerase III promoter B box—red), with extensive heterogeneity located 3' to the mid-sequence poly-A stretch that have been reported to exist in Alu sequences[3,4].
Figure 15:
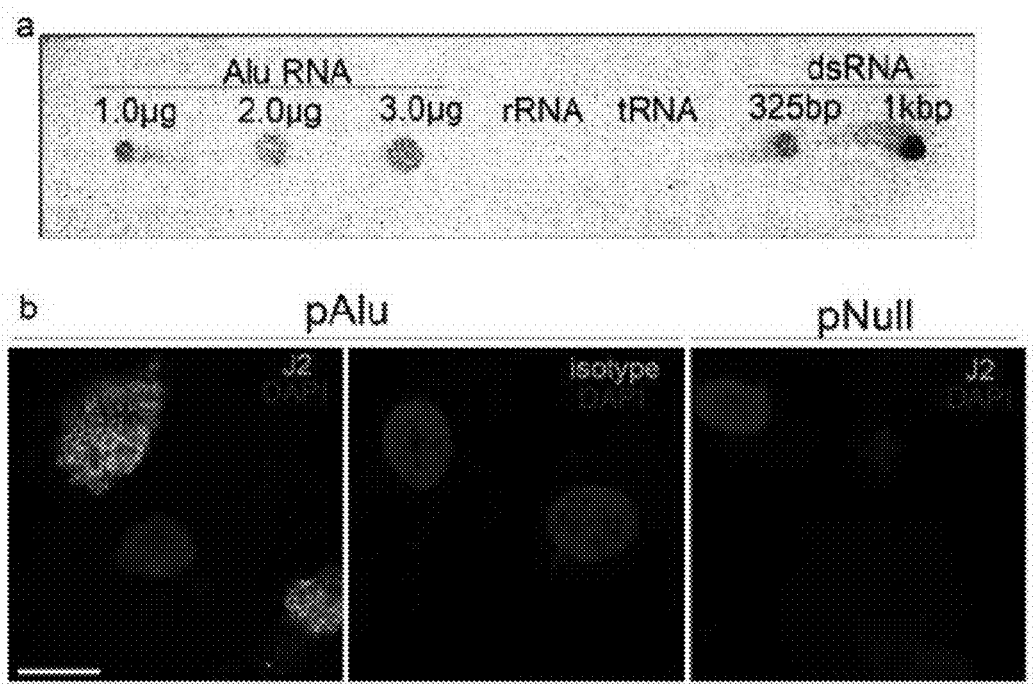
FIG. 15 J2 anti-dsRNA antibody recognizes Alu RNA. a, Alu RNA duplex isolated and cloned from the retinal pigmented epithelium (RPE) of a human eye with geographic atrophy was recognized by J2 anti-dsRNA antibody in an immuno-dot blot format. J2 antibody did not recognize rRNA or tRNA (negative controls), but did recognize RNA duplexes of 325-bp or 1-kbp in length (positive controls). b, Immunofluorescent imaging of human RPE cells transfected with pAlu shows that J2 recognizes Alu expressed in these cells (left panel). Specificity of staining confirmed by absence of staining with isotype control antibody (middle panel) and by the absence of immunodetection following transfection with pNull (right panel). Representative images shown. n=3. Scale bar (20 μm).
Figure 16:
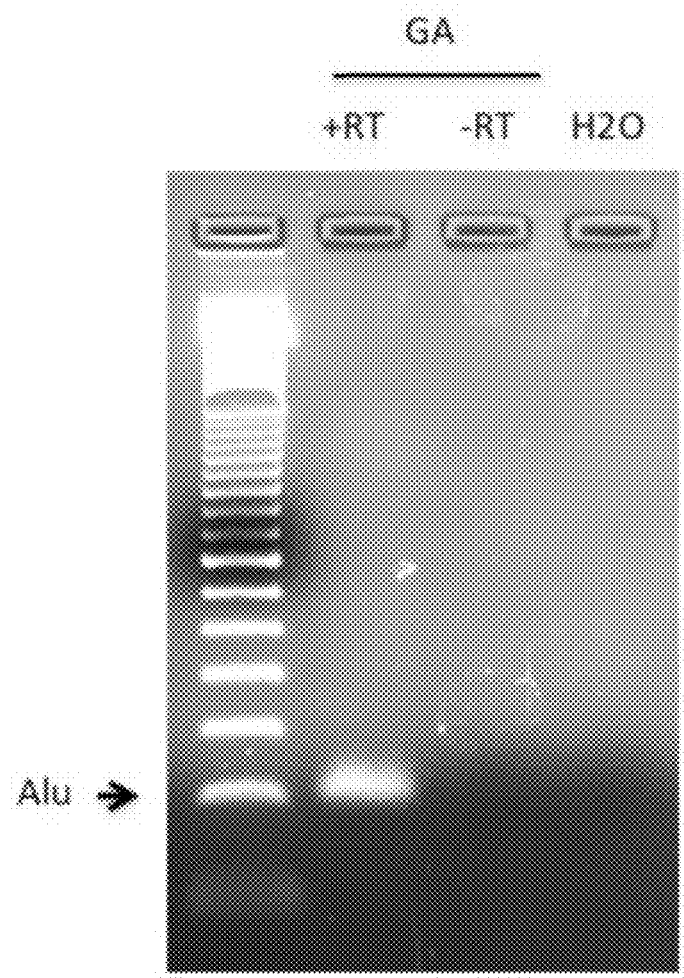
FIG. 16 Confirmation of lack of DNA contamination in Alu RNA PCR. The relative abundance of Alu RNA in the RPE of human eyes with human geographic eyes was presented in FIG. 2f. Shown above is the detection of the PCR product band for a sample of human geographic atrophy RPE that underwent reverse transcription (RT+). No amplification was detected in the negative controls where reverse transcriptase (RT−) was omitted or where water alone was analyzed. These data demonstrate the absence of DNA contamination in the sample.

The present inventors recovered clones from 8 of the 12 geographic atrophy eyes and identified two distinct sequences with high homology (E=3.3×10$^{-103}$; 1.1×10$^{-76}$) to Alu repeat RNAs (FIG. 14). These sequences showed homology to the Alu Sq subfamily consensus sequence. Apart from mitochondrial RNAs that were occasionally found in the RPE of both geographic atrophy and normal eyes, Alu RNAs were the only dsRNA transcripts identified specifically in the geographic atrophy samples. The present inventors confirmed that the J2 monoclonal antibody recognized Alu RNA both in immunoblotting and in immunofluorescence assays (FIG. 15). The present inventors also detected a greater than 40-fold increase in the abundance of Alu RNAs in the RPE of human eyes with geographic atrophy compared to control eyes (n=7), but no significant difference in Alu RNA abundance was detected in the adjacent neural retina between the two groups (FIG. 2f, FIG. 16). The present inventors did not identify exact matches to these Alu sequences in the reference human genome. This could be attributed to genetic variations or regions not represented in the reference genome or to chimeric Alu formation. Further studies are needed to elucidate the genomic origin of and regulatory factors involved in transcription of these Alu RNAs.

DICER1 Depletion Induces Alu RNA Accumulation

Figure 3:
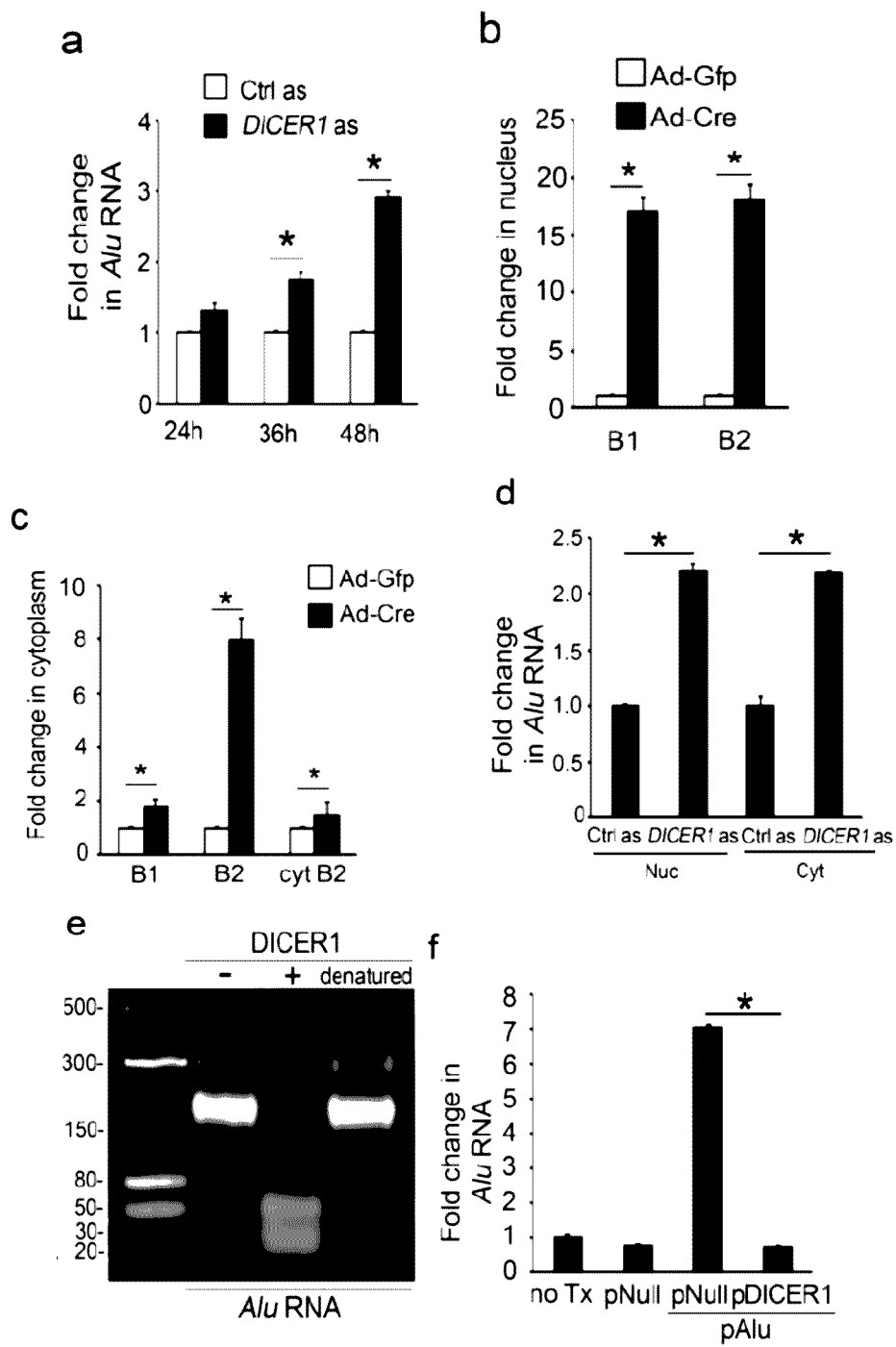
FIG. 3 DICER1 degrades Alu RNA. a, Transfection of antisense oligonucleotide (as) targeting DICER1 into human RPE cells induced a time-dependent increase in the abundance of Alu RNA transcripts. b, c, Transfection of adenoviral vector coding for Cre recombinase (Ad-Cre) into mouse RPE cells isolated from Dicer1$^{f/f}$ mice increased, in the nucleus (b) and the cytoplasm (c), the abundance of B1 and B2 RNAs, the Alu-like repetitive elements in the mouse, compared to cells transfected with adenoviral vector coding for green fluorescent protein (Ad-GFP). d, DICER1 as treatment of human RPE cells upregulated Alu RNA levels in both the nucleus (Nuc) and cytoplasm (Cyt). e, Alu RNA isolated and cloned from the RPE of human eye with geographic atrophy was degraded by recombinant DICER1 digestion (+) as visualized by agarose gel electrophoresis. Digestion with heat denatured DICER1 did not degrade Alu RNA. Image representative of 6 experiments. f, The increased abundance of Alu RNA in human RPE cells transfected with plasmid coding for Alu (pAlu) compared to pNull or no treatment (no Tx) at 24 h was reduced by co-transfection with pDICER1. *P<0.05. n=4-8 (a-d, f). RNA abundance was quantified by real-time RT-PCR, normalized to 18S rRNA levels, and normalized to levels in control as-treated (for Alu) or Ad-GFP-infected cells (for B elements).
Figure 17:
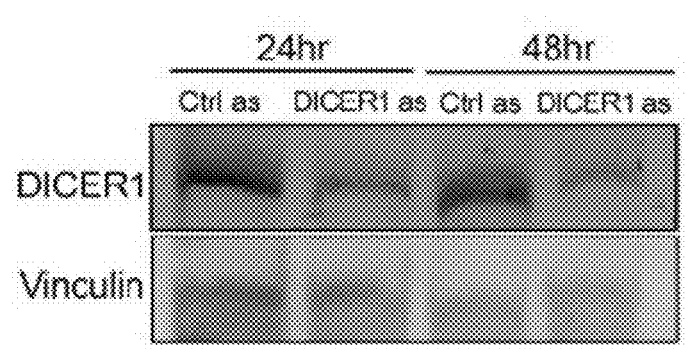
FIG. 17 Validation of DICER1 knockdown. Transfection of DICER1 antisense oligonucleotides (as) into human RPE cells knocks down DICER1 protein abundance, as monitored by Western blot analysis, over 2 days. Efficiency of protein loading is monitored by blotting for the housekeeping Vinculin protein. Representative of 3 experiments.
Figure 18:
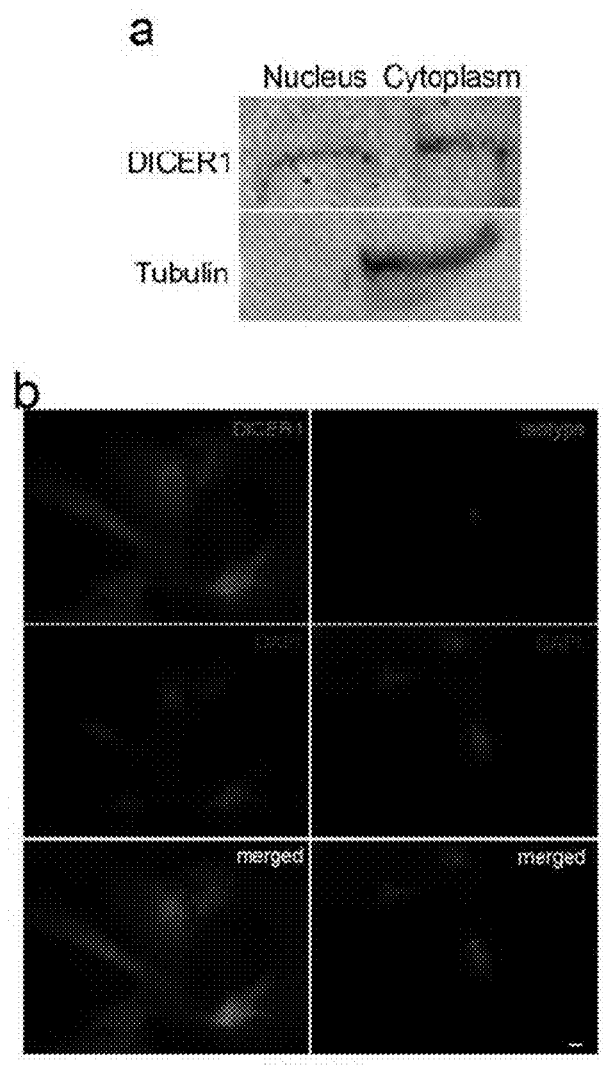
FIG. 18 DICER1 is expressed in nucleus and cytoplasm. a, Western blot shows expression of DICER1 in both the nuclear and cytoplasmic fractions of human RPE cells. Blotting of the same protein sample reveals the presence of Tubulin in the cytoplasmic fraction and not in the nuclear fraction. b, Merged images (bottom row) of DICER1 immunofluorescence (red, top row) and nuclear DAPI fluorescence (middle row) confirm expression of DICER1 in both the nucleus and the cytoplasm of human RPE cells. Representative images shown. Scale bar, 10 μm.
Figure 19:
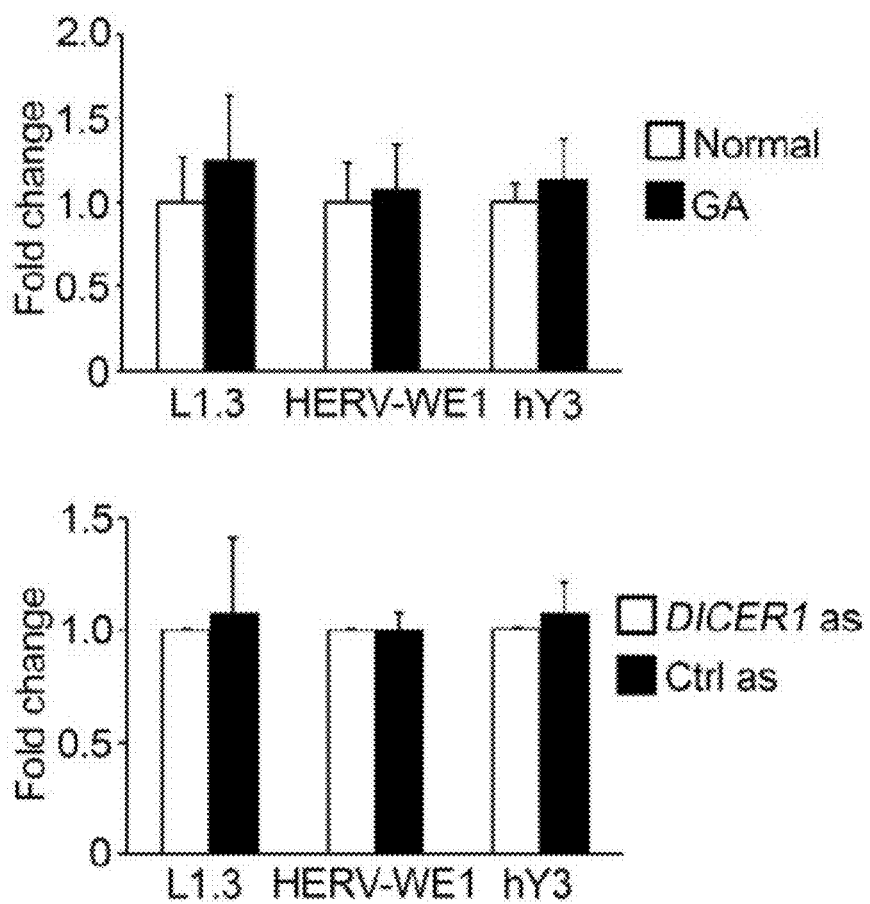
FIG. 19 Retrotransposons and repetitive RNAs are not generically activated in geographic atrophy or by DICER1 depletion. In the RPE of human eyes with geographic atrophy (GA, n=7), there was no significant increase in the abundance of RNAs coded by LINE L1.3, a long interspersed repetitive element, human endogenous retrovirus-W envelope (HERV-WE1), a long terminal repeat retrotransposon, or hY3, a repetitive small cytoplasmic Ro RNA compared to normal human eyes (top, n=8). These RNAs also were not upregulated by DICER1 antisense (as) knockdown, compared to control (Ctrl) as treatment, in human RPE cells (bottom). n=3. Transcript abundance monitored by real-time RT-PCR and normalized to 18S rRNA levels.

The present inventors tested whether Alu RNA accumulation in the RPE of geographic atrophy was the result of deficient DICER1 processing activity. DICER1 knockdown in human RPE cells using antisense oligonucleotides resulted in increasing Alu RNA accumulation over time (FIG. 3a, FIG. 17). Similarly, Ad-Cre infection of RPE cells isolated from Dicer1$^{f/f}$ mice resulted in accumulation of B1 and B2 repeat RNAs (FIG. 3b, c), which are Alu-like short interspersed repetitive elements in the mouse. Interestingly, DICER1 was expressed in both the nucleus and cytoplasm of RPE cells and its depletion led to accumulation of Alu/B1/B2 RNA in both cellular compartments (FIG. 3b-d, FIG. 18). In addition, recombinant DICER1 degraded Alu RNA, and the biological specificity of this cleavage was confirmed by the inability of heat-denatured DICER1 to degrade Alu RNA (FIG. 3e). Enforced expression of DICER1 in human RPE cells reduced Alu RNA abundance following enforced expression of Alu RNA (FIG. 3f), consistent with degradation of these repetitive transcripts by DICER1 in vivo. Collectively these data confirm that DICER1 dysregulation can trigger Alu/B1/B2 RNA accumulation.

Because cell stresses such as heat shock or viral infection can induce generalized retrotransposon activation, the present inventors wondered whether Alu RNA accumulation in geographic atrophy might be a generic response in dying retina. However, in the RPE of human eyes with geographic atrophy and in DICER1-depleted human RPE cells, there was no increase in the abundance of RNAs coded by L1.3 (a long interspersed repetitive element), human endogenous retrovirus-W envelope (a long terminal repeat retrotransposon), or hY3 (a repetitive small cytoplasmic Ro RNA) (FIG.

19). These data demonstrate that Alu RNA accumulation is a biologically specific response to DICER1 depletion.

Figure 20:
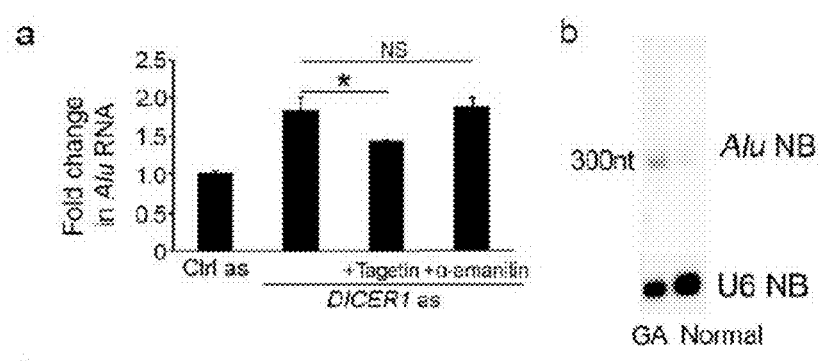
FIG. 20 Alu RNA induced by DICER1 depletion is RNA Pol III derived. a, The upregulation of Alu RNA in RPE cells treated with antisense (as) oligonucleotides targeting DICER1, compared to control (Ctrl), is inhibited by treatment with the Pol III inhibitor tagetitoxin (tagetin), but not by the Pol II inhibitor α-amanitin. *, P<0.05, NS, not significant, compared to treatment with DICER1 as treatment alone. b, Northern blot (NB) shows that the abundance of Alu RNA species in the RPE of a human eye with geographic atrophy (GA) is greater than in normal human eye RPE, and is principally approximately 300 nucleotides long, consistent with the length of a non-embedded Pol III derived transcript. Reprobing these samples with a probe corresponding to the "S region" of the 7SL RNA gene that is not present in Alu elements shows that 7SL RNA abundance is not different between the RPE of normal and GA human eyes. Abundance of U6 RNA in GA and normal eyes shows loading efficiency. c, Northern blot shows that Alu probe detects in vitro transcribed Alu RNA but not 7SL RNA in mouse liver (which lacks primate-specific Alu), and reprobing these samples confirms specificity of the 7SL probe. d, DICER1 knockdown by antisense (as) oligonucleotides in human RPE cells does not, compared to control (Ctrl) as treatment, induce upregulation of several Pol II-transcribed genes (ADAR2, NICN, NLRP, SLFN 11) that contain embedded Alu sequences in their exons. n=3.
Figure 20:
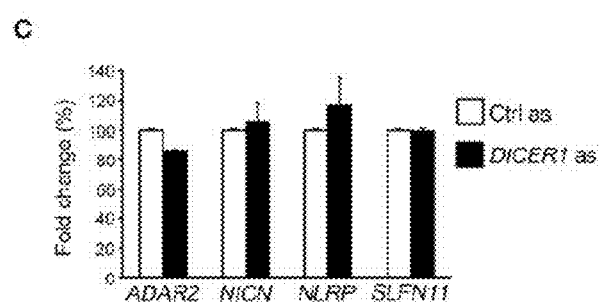
Figure 21:
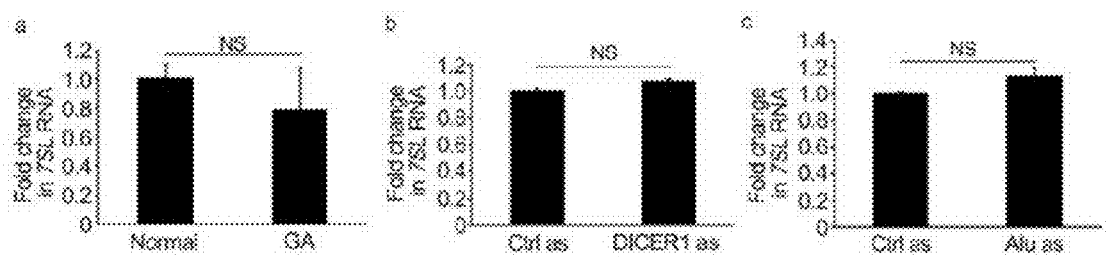

To determine whether Alu RNA accumulation was derived from RNA polymerase II (Pol II) or Pol III transcription, the present inventors performed experiments using α-amanitin (a Pol II inhibitor) and tagetitoxin (a Pol III inhibitor). Alu RNA upregulation induced by DICER1 knockdown was inhibited by tagetitoxin but not α-amanitin (FIG. 20). The present inventors also found using Northern blotting that Alu RNA from the RPE of human eyes with geographic atrophy was approximately 300 nucleotides in length, consistent with the length of non-embedded Pol III Alu transcripts. Because homology between Alu RNA and 7SL RNA, the evolutionary precursor of Alu, can complicate interpretation of northern blot analysis, the present inventors reprobed these samples using a probe that specifically detects the non-Alu "S domain" of 7SL RNA. In contrast to the increased amounts of RNA species detected by the Alu-targeting probe in geographic atrophy RPE, there was no difference in 7SL RNA abundance. The present inventors also confirmed that the Alu probe did not detect endogenous 7SL RNA under the stringent conditions the present inventors employed. Corroborating these data, real-time RT-PCR analysis showed that 7SL RNA was not dysregulated in the RPE of human eyes with geographic atrophy or in DICER1-depleted human RPE cells (FIG. 21).

DICER1 knockdown also did not induce upregulation of several Pol II-transcribed genes (ADAR2, NICN, NLRP, SLFN 11) that contain embedded Alu sequences in their exons. Collectively, these data suggest that Alu RNA detected in the RPE of human eyes with geographic atrophy are primary Alu transcripts and not passenger or bystander sequences embedded in other RNAs. Conclusive assignment of these Alu sequences as Pol III transcripts must await precise determination of their transcription start site.

Alu RNA Induces RPE Degeneration

Figure 4:
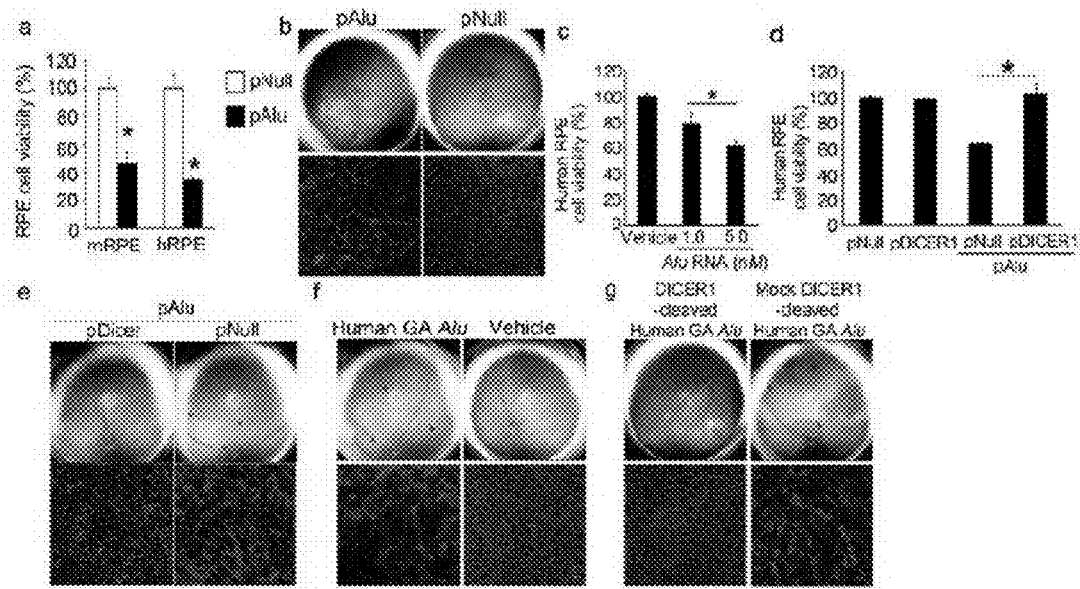
FIG. 4 DICER1 protects RPE cells from Alu RNA cytotoxicity. a, Transfection of mouse or human retinal pigmented epithelium cells (mRPE or hRPE) with plasmid coding for Alu RNA (pAlu) compromised cell viability. b, Subretinal administration of pAlu induced RPE degeneration in wild-type mice whereas pNull did not do so. Fundus photograph (top row) shows area of degeneration in pAlu injected eye compared to the normal appearance in pNull. Flat mount preparations stained with anti-zonula occludens-1 antibody (ZO-1, red, bottom row) show marked distortion of RPE cell shape and size compared to pNull-injected eye. c, Alu RNA induced dose-dependent increase in cell death of human RPE cells. d, Cell death of human RPE cells induced by transfection of pAlu was inhibited by co-transfection with pDICER1 but not pNull. (a,c,d) Cell viability monitored by MTS assay at 2 days. Values normalized to null plasmid (pNull) transfected or vehicle treated cells. *P<0.05 by Student t test. n=4-6. e, Subretinal co-administration of pDICER1, but not of pNull, inhibited pAlu induced RPE degeneration in wild-type mice. f, Subretinal administration of Alu RNA isolated and cloned from the RPE of a human eye with geographic atrophy (GA) induced RPE degeneration in wild-type mice whereas subretinal injection of vehicle did not. g, Subretinal injection of this Alu RNA, when subjected to cleavage by DICER1, did not induce RPE degeneration in wild-type mice whereas Alu RNA subjected to mock cleavage by DICER1 did do so, as evident on fundus photography (top row) or flat mount preparation (bottom row). Area of degeneration outlined by blue arrowheads in fundus photographs (b, e-g). Scale bars (20 μm). n=10-15 (b, e-g).
Figure 22:
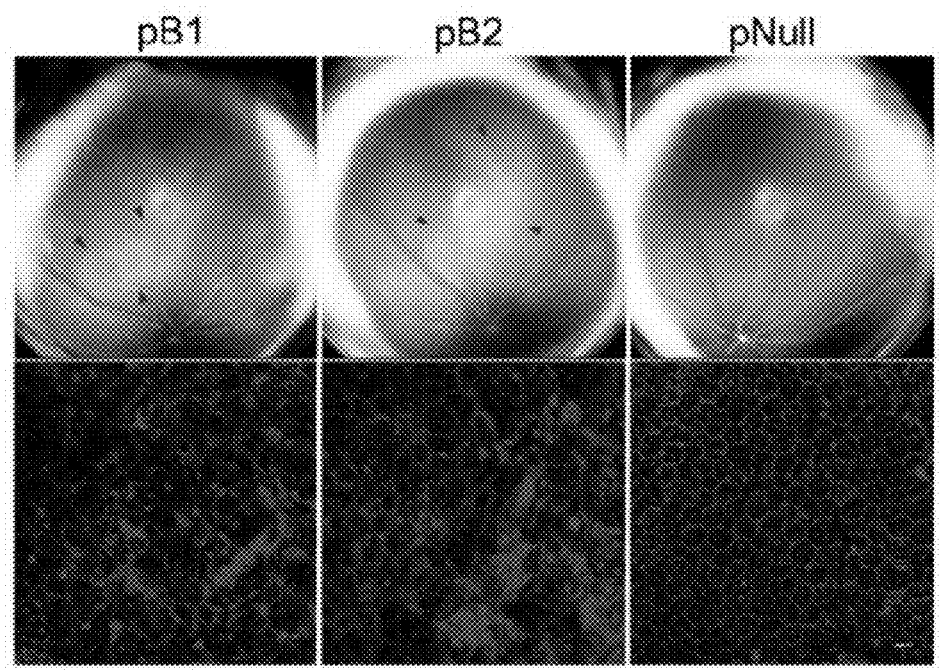
FIG. 22 Overexpression of B1 or B2 RNA induces RPE degeneration. Subretinal transfection of pB1 or pB2 RNAs, but not of pNull, induces RPE degeneration in wild-type mice. Top row shows fundus photographs demonstrating areas of degeneration outlined by blue arrowheads. Bottom row shows ZO-1 stained (red) RPE flat mounts demonstrated marked degeneration and disarray of the RPE cells in mice overexpressing B1 or B2 RNAs. Circular flash artifact is seen in the centre of the fundus photographs. n=4. Representative images shown. Scale bar, 20 µm.

Next the present inventors tested whether accumulation of Alu RNA might promote the development of geographic atrophy. Transfecting human or wild-type mouse RPE cells with a plasmid coding for Alu (pAlu) reduced cell viability (FIG. 4a). Subretinal transfection of plasmids coding for two different Alu RNAs or for B1 or B2 RNAs induced RPE degeneration in wild-type mice (FIG. 4b, FIG. 22, and data not shown). Treatment of human RPE cells with a recombinant 281 nucleotide (nt)-long Alu RNA that is identical to a Pol III derived Alu RNA isolated from a human embryonal carcinoma cell line, i.e., a single RNA strand that folds into a defined secondary structure, resulted in a dose-dependent increase in cell death (FIG. 4c). These findings suggest that endogenous DICER1 can degrade small amounts of Alu RNA but are overwhelmed by high levels. Consistent with this concept, overexpression of DICER1 blocked pAlu-induced cell death in human RPE cells (FIG. 4d) and RPE degeneration in wild-type mice (FIG. 4e).

Figure 23:
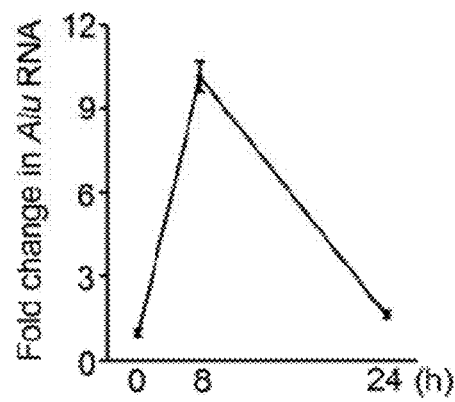
FIG. 23 Alu RNA enters retinal pigmented epithelium (RPE) cells in vivo. Subretinal administration of Alu RNA in wild-type mice achieved RPE cell delivery at 8 h after injection as monitored by real-time RT-PCR in isolated cell lysates (n=3).
Figure 24:
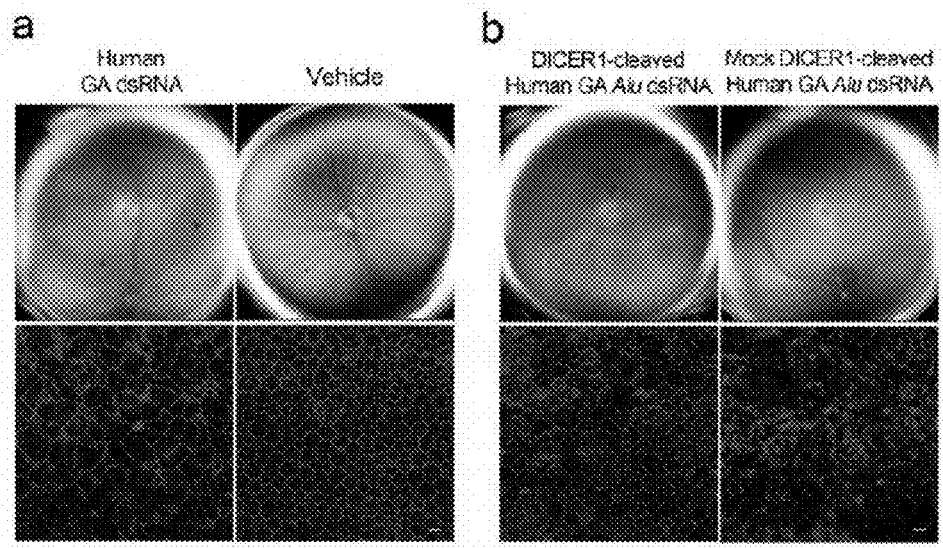
FIG. 24 Human GA Alu dsRNA does not induce RPE degeneration when cleaved by DICER1. a, Subretinal administration of a fully complementary synthetic Alu RNA (dsRNA) corresponding to the sequence of an Alu RNA isolated from a human eye with geographic atrophy (GA) induces RPE degeneration in wild-type mice. Vehicle administration does not damage the retina. Top panels show fundus photographs with the area of RPE degeneration outlined by blue arrowheads. Circular flash artifact is seen in the centre of the fundus photographs. Bottom panels show ZO-1 stained (red) RPE flat mounts that are well arrayed in vehicle (bottom) but disorganized in Alu dsRNA (top). b, This Alu dsRNA did not induce RPE degeneration when it was first subjected to cleavage by recombinant DICER1. However, when subjected to mock cleavage by DICER1, this Alu dsRNA did induce RPE degeneration. n=4. Representative images shown. Scale bar, 20 µm.

The present inventors verified that subretinal injection of Alu RNA resulted in its delivery to RPE cells in wild-type mice (FIG. 23), consistent with the ability of long RNAs with duplex motifs to enter cells[28]. The present inventors then cloned a 302-nt long Alu RNA isolated from the RPE of a human eye with geographic atrophy and transcribed it in vitro to generate partially and completely annealed structures that mimic Alu RNAs transcribed by Pol III and Pol II, respectively. Subretinal injection of either of these Alu RNAs resulted in RPE degeneration in wild-type mice (FIG. 4f, FIG. 24), supporting the assignment of disease causality in accord with the molecular Koch's postulates. In contrast, subretinal injection of these Alu RNAs digested with DICER1 did not induce RPE degeneration in wild-type mice (FIG. 4g, FIG. 24). When these Alu RNAs were subjected to mock DICER1 digestion, they retained their ability to induce RPE degeneration, suggesting a role for DICER1 in protecting against Alu RNA-induced degeneration.

Figure 25:
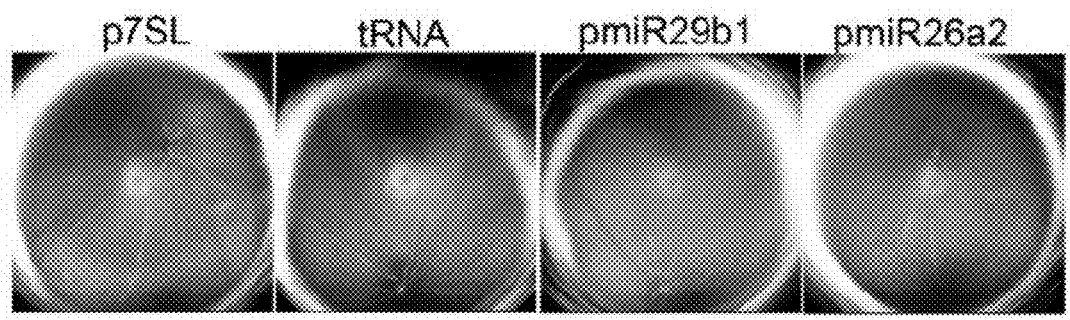
FIG. 25 RPE degeneration does not occur in response to a variety of structured RNAs. Subretinal transfection of transfer RNA (tRNA) or of plasmids coding for 7SL RNA, pri-miRNA-29b1 or pri-miRNA26a2 in wild-type mice did not induce retinal toxicity that was evident on fundus photography. Circular flash artifact is seen in the centre of the fundus photographs. N=4. Representative images shown.
Figure 26:
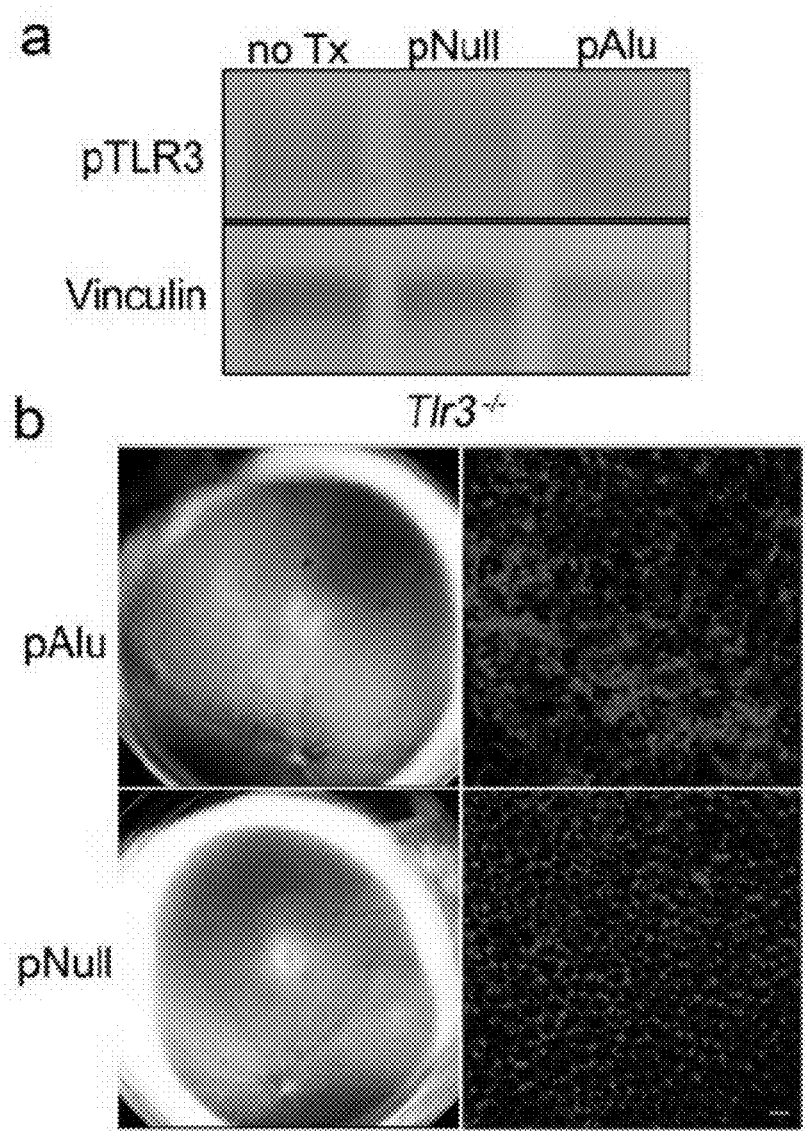
FIG. 26 Alu RNA does not cause RPE degeneration via TLR3. a, Western blot shows that transfection of pAlu or pNull does not induce TLR3 phosphorylation, relative to the levels of the housekeeping protein Vinculin, in human RPE cells. b, Subretinal transfection of pAlu induced RPE degeneration in Tlr3−/− mice where pNull transfection did not do so. Representative images shown. n=4. Scale bar, 20 µm.

The present inventors tested whether other structured RNAs of similar length as Alu would damage the retina. Subretinal transfection of transfer RNA or plasmids coding for 7SL RNA or two different primary miRNAs did not induce RPE degeneration in wild-type mice (FIG. 25). The present inventors reported that chemically synthesized dsRNAs that mimic viral dsRNA can induce RPE degeneration by activating toll like receptor-3 (TLR3)[29], a pattern receptor that generically recognizes dsRNA. However, transfection of a plasmid coding for Alu RNA did not induce TLR3 phosphorylation in human RPE cells and did induce RPE degeneration in Tlr3−/− mice (FIG. 26). These results indicate that the ability of Alu RNA to induce RPE degeneration cannot be attributed solely to its repetitive or double stranded nature, as it exerted effects distinct from other structured dsRNAs of similar length.

Figure 27:
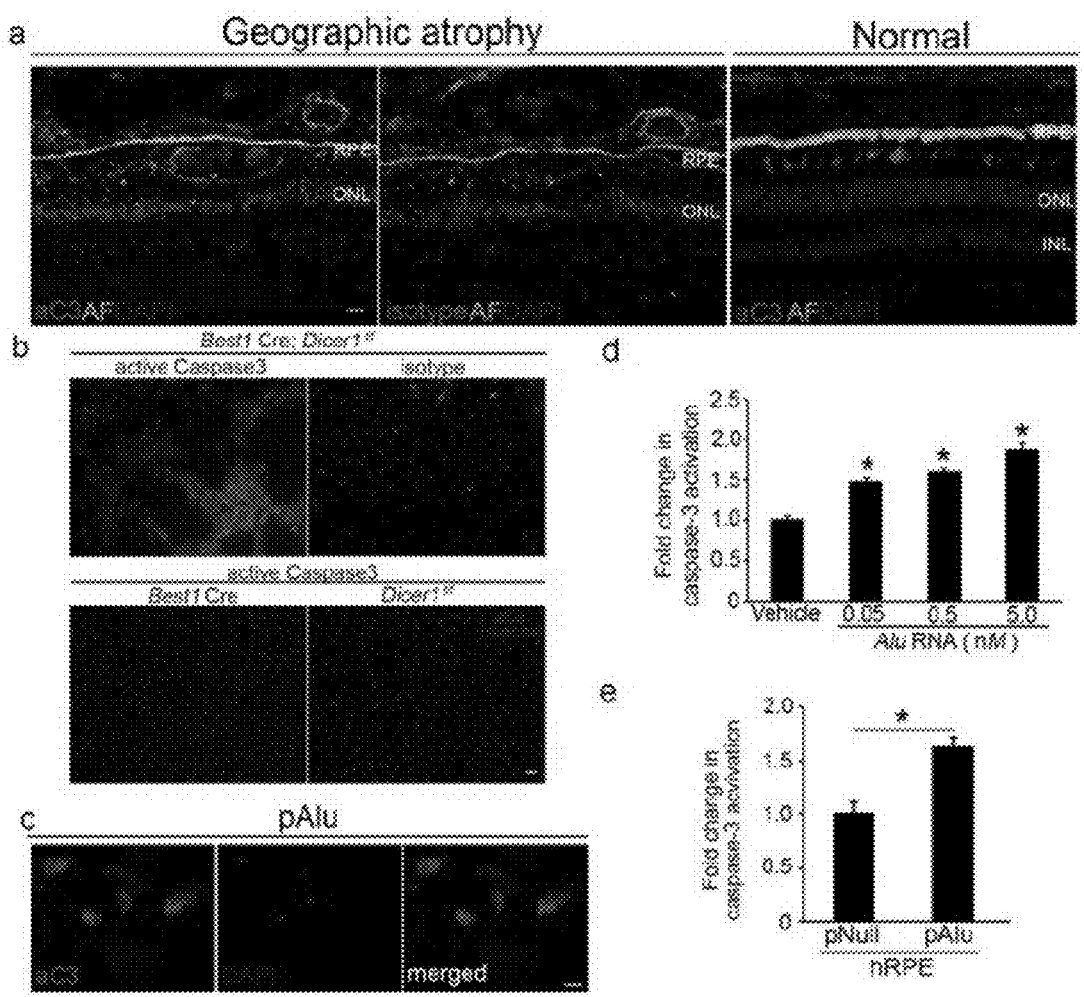
FIG. 27 DICER1 reduction or Alu RNA augmentation induces caspase-3 activation. a, Immunolocalization of activated caspase-3 (red) in the RPE of human eyes with geographic atrophy (left panel). Specificity of immunolabeling revealed by absence of staining with isotype control antibody (middle panel) and in control eyes stained with antibody against cleaved caspase-3 (right panel). Autofluorescence of RPE and choroid seen in green channel. Nuclei stained by DAPI (blue). b, Flat mounts of BEST1 Cre; Dicer1$^{f/f}$ mice show evidence of caspase-3 activation (red staining, top left panel). Specificity of immunolabeling revealed by absence of staining with isotype control antibody (top right panel). No caspase-3 activation was detectable in the RPE of littermate control BEST1 Cre or Dicer1$^{f/f}$ mice (bottom panels). c, Human RPE cells transfected with pAlu showed evidence of caspase-3 activation (red staining, top left panel). DAPI (blue staining) and merged images are also shown. Scale bars (20 µm, a,b; 10 µm, c). Representative images shown. n=4-6. d, Exposure of human RPE cells to Alu RNA induced dose-dependent increase in caspase-3 activation, as monitored by fluorometric plate assay. n=3, *$P<0.05$ compared to vehicle by Student t test. e, Transfection of human RPE cells with pAlu induced increase in caspase-3 activation. n=3, *$P=0.47$ by Student t test.

The mechanism of RPE cell death in geographic atrophy has not been previously defined. DNA fragmentation has been identified in RPE cells in human eyes with geographic atrophy[30], and Dicer1 knockdown has been associated with induction of apoptosis in diverse tissues[12,31]. The present inventors now provide evidence of caspase-3 cleavage in regions of RPE degeneration in human eyes with geographic atrophy (FIG. 27). Caspase-3 cleavage was also observed in the RPE cells of BEST1Cre; Dicer1$^{f/f}$ mice and in Alu RNA-stimulated or -overexpressing human RPE cells. These data suggest a role for Alu RNA-induced RPE cell apoptosis triggered by DICER1 dysregulation in geographic atrophy.

Figure 28:
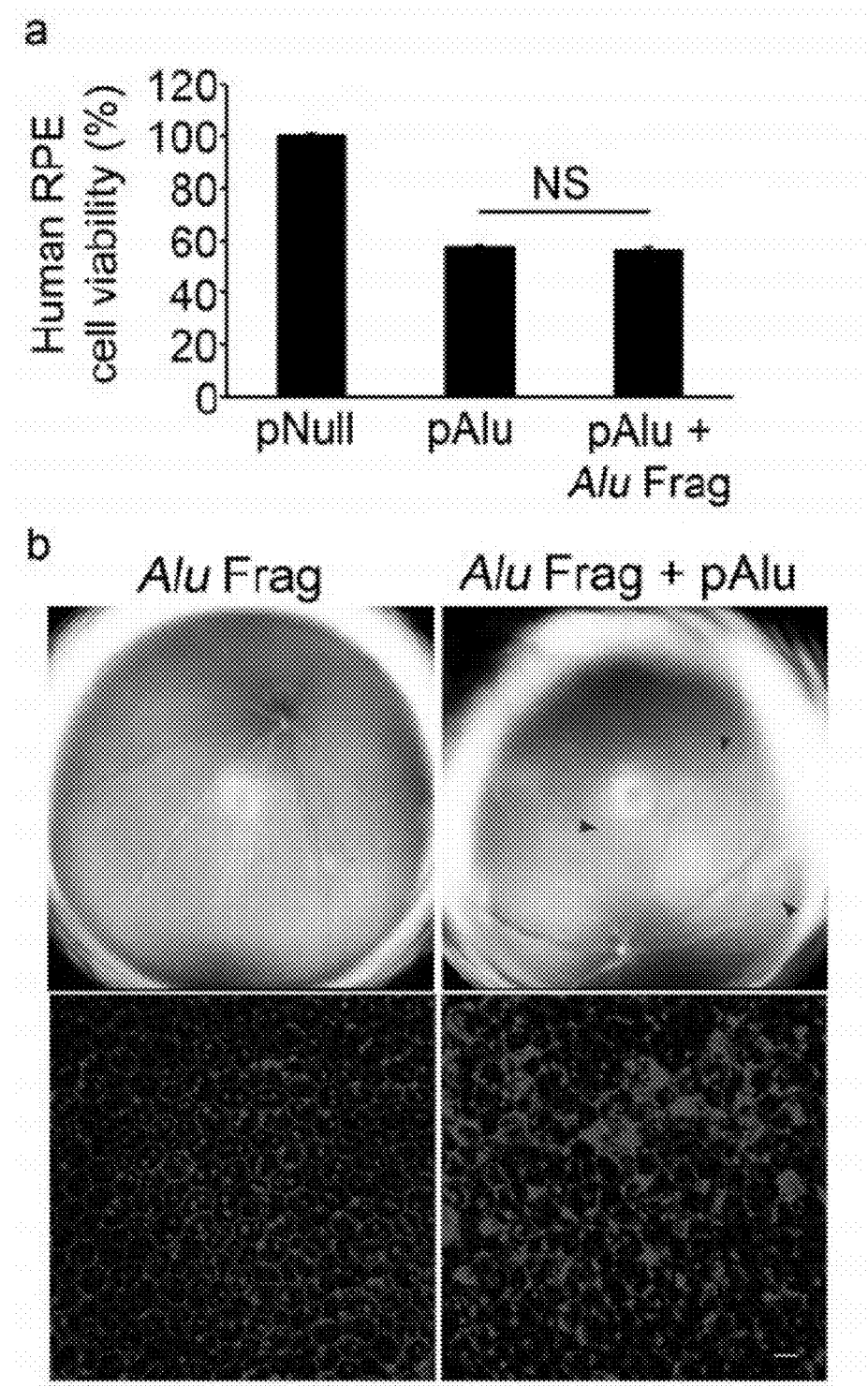
FIG. 28 Alu RNA cleavage fragments do not modulate RPE degeneration. a, Transfection of pAlu induced cell death in human RPE cells. Cotransfection of DICER1-cleaved Alu RNA fragments did not change the degree of cell death. n=3. b, Subretinal transfection of DICER1-cleaved Alu RNA fragments (Frag) in wild-type mice did not cause RPE degeneration as seen by fundus photography (top left) or ZO-1-stained (red) RPE flat mounts (bottom left). Cotransfections of these fragments did not prevent the RPE degeneration induced by pAlu in wild-type mice (right panels). n=4. Representative images shown. Scale bar, 20 µm.

Although the present inventors show that Alu RNA induces RPE degeneration, the presented observations could be consistent with the idea that an imbalance in small RNA species produced from long Alu RNAs could contribute to the RPE degeneration phenotype. To study this question, the present inventors exposed human RPE cells or wild-type mice to DICER1 cleavage fragments of Alu RNA. Subretinal transfection of these fragments alone in wild-type mice had no detectable effect on RPE cell morphology, and co-administering these fragments did not prevent RPE cell degeneration induced by subretinal transfection of a plasmid coding for Alu RNA (FIG. 28). Similarly, these fragments did not prevent human RPE cell death induced by overexpression of Alu RNA. These data suggest that upregulation of long Alu RNA rather than imbalance in Alu RNA-derived small RNA fragments is responsible for RPE degeneration induced by DICER1 reduction.

As these experiments were performed with in vitro cleavage fragments the present inventors cannot be certain whether in vivo cleavage fragments would function similarly. However, Alu RNAs with varying sequences induced RPE degeneration in vivo. Because the cleavage fragments of these different Alu RNAs would not be identical it is unlikely that they all execute identical biological functions, particularly if they functioned as miRNAs. Another line of evidence that Alu RNA, and not its cleavage fragments, is responsible for RPE degeneration comes from functional rescue experiments (see below) wherein antisense-mediated inhibition of Alu RNA blocks human RPE cell death induced by DICER1 knockdown and inhibition of B1/B2 RNA blocks RPE degeneration in Dicer1-depleted mice and mouse RPE cells. Because these antisense treatments would not be expected to alter the reduced levels of DICER1- cleaved Alu/B1/B2 RNA fragments, the imbalance in these fragments is unlikely to have induced RPE degeneration. Nevertheless, subtle functions of these small RNAs in modulating Alu RNA induced pathology cannot be excluded.

Figure 29:
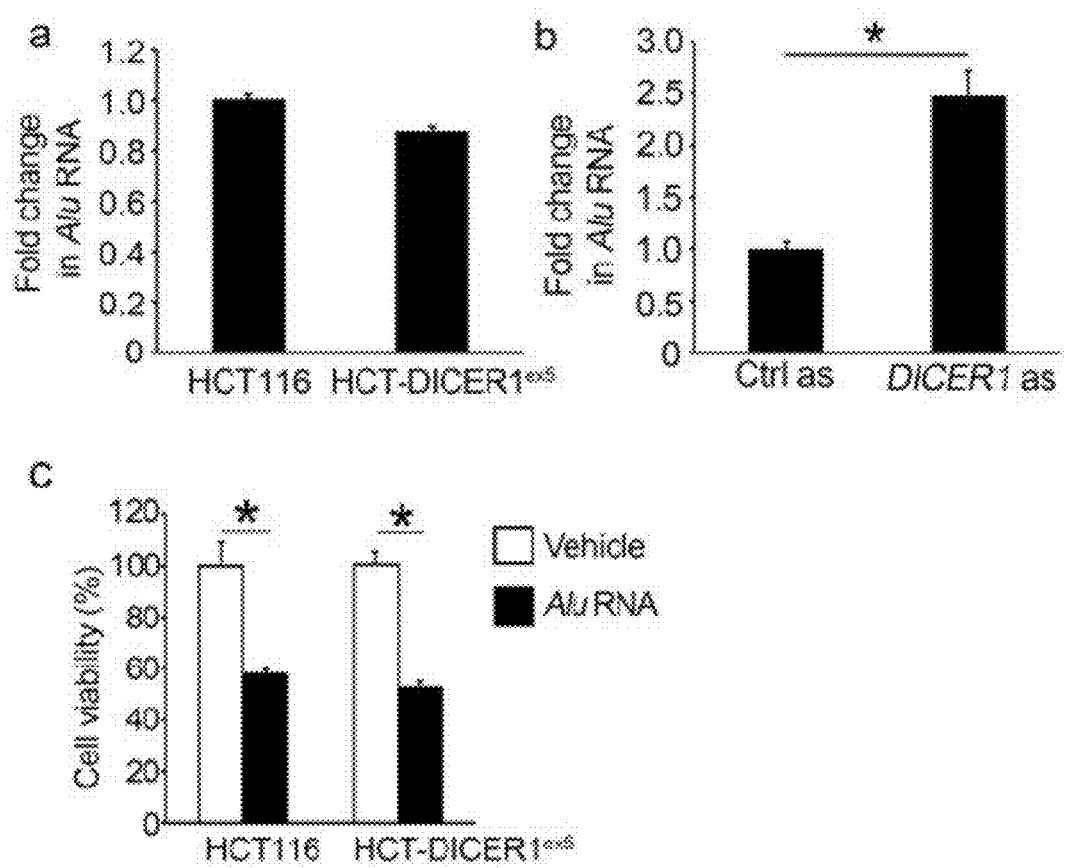
FIG. 29 Impaired DICER1 processing of microRNAs does not increase Alu RNA abundance or modulate Alu RNA cytotoxicity. a, There was no significant difference ($P>0.05$) in Alu RNA transcript abundance between HCT116 parent cells and HCT mutant cells carrying a mutation in exon 5 (ex5) of DICER1 which renders it incapable of processing microRNAs. b, Transfection of anti-sense oligonucleotide (as) targeting DICER1 into HCT116 cells increased the abundance of Alu RNA transcripts compared to control anti-sense oligonucleotide (Ctrl as) at 48 h. Transcript abundance monitored by real-time RT-PCR and normalized to 18S rRNA levels. c, Alu RNA induced similar levels of cell death in HCT116 parent and HCT-DICER1$^{ex5}$ cells. *$P<0.05$ by Student t test. n=4-6.

To dissect the contribution of Alu RNA accumulation versus that of miRNA dysregulation to RPE degeneration in the context of reduced DICER1 expression, the present inventors re-examined HCT-DICER1$^{ex5}$ cells in which miRNA biogenesis is impaired but long dsRNA cleavage is preserved due to the intact RNase III domains. The present inventors found no significant difference in Alu RNA levels between HCT-DICER1$^{ex5}$ and parent HCT116 cells (FIG. 29). In contrast, when DICER1 was knocked down by antisense oligonucleotides in HCT116 cells, increased Alu RNA accumulation was observed. Also, Alu RNA induces similar levels of cytotoxicity in HCT-DICER1$^{ex5}$ and parent HCT116 cells, suggesting that coexisting miRNA expression deficits do not augment Alu RNA induced RPE degeneration. In conjunction with the discordance in the RPE degeneration phenotype between ablation of Dicer1 and that of various other small RNA biogenesis pathway genes in mice, the findings suggest that Alu RNA accumulation is critical to cytotoxicity induced by DICER1 reduction.

RPE Degeneration Blocked by Alu RNA Inhibition

Figure 5:
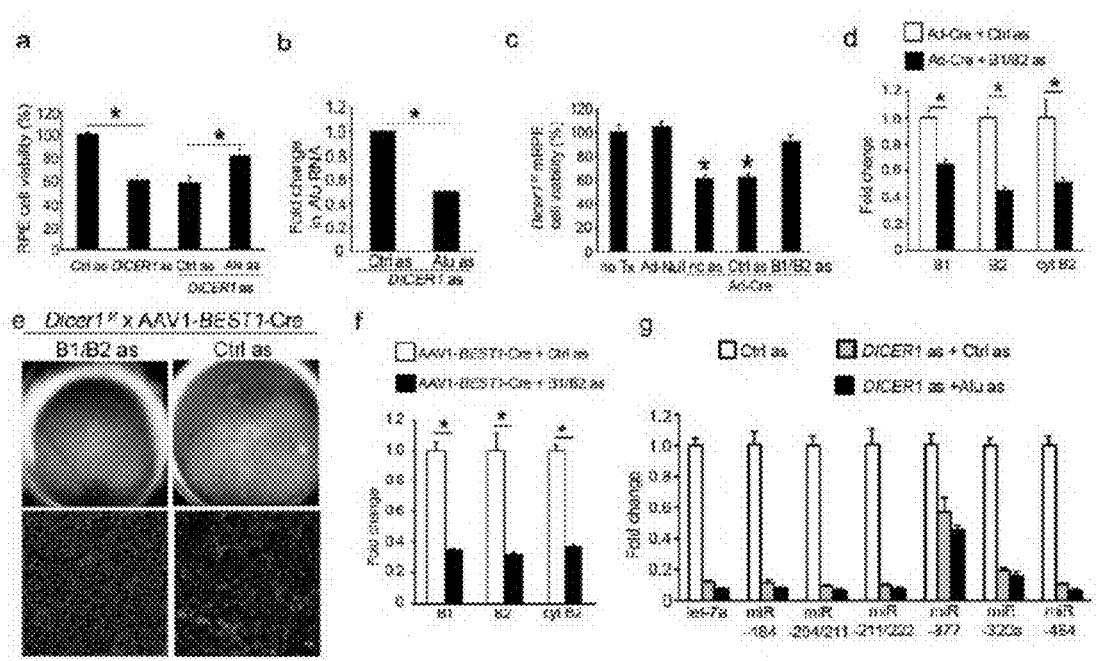
FIG. 5 DICER1 dyregulation induces RPE cell death via Alu RNA accumulation. a, Loss of human RPE cell viability, as monitored by MTS assay, induced by transfection of antisense oligonucleotide (as) targeting DICER1 was rescued by co-transfection of Alu RNA as. Levels normalized or compared to transfection with control (Ctrl) antisense oligonucleotide. b, Alu RNA as inhibited accumulation of Alu RNA induced by DICER1 as. c, Ad-Cre but not Ad-Null induced loss of cell viability of Dicer1$^{f/f}$ mouse RPE cells. This was rescued by transfection of antisense oligonucleotide targeting B1 and B2 RNAs but not by control (Ctrl) antisense oligonucleotide. Levels normalized to untreated cells (no Tx). d, B1/B2 RNA as inhibited accumulation of B1 and B2 RNAs induced by Ad-Cre-induced Dicer1 depletion. *P<0.05 by Student t test. n=4-6 (a-d). d, Subretinal AAV-BEST1-Cre administration induced RPE degeneration (blue arrowheads in fundus photograph on top row and marked increase in RPE cell size and distortion of RPE cell shape in ZO-1 stained (red) RPE flat mounts (bottom row) in Dicer1$^{f/f}$ mice 20 days after injection. Subretinal administration of cholesterol-conjugated B1/B2 as, but not Ctrl as, 10 days after AAV-BEST1-Cre injection inhibited RPE degeneration (e) and abundance of B1/B2 RNAs in the RPE of these mice, as monitored by real-time RT-PCR at 10 days after as injection, normalized to 18S rRNA levels, and normalized to levels in eyes treated with cholesterol-conjugated Ctrl as (f). n=8 (e,f). Scale bar, 20 μm. (e). g, DICER1 as treatment of human RPE cells led to global reduction of miRNA expression at 2 days compared to Ctrl as. There was no significant difference in miRNA abundance between Alu as and Ctrl as-treated DICER1 depleted cells. n=3.

The present inventors then tested whether the cytotoxic effects of DICER1 reduction could be attributed to Alu RNA accumulation. DICER1 knockdown in human RPE cells by antisense oligonucleotides reduced cell viability (FIG. 5a). This cytotoxic effect of DICER1 reduction was inhibited by antisense oligonucleotides targeting Alu RNA sequences but not by a scrambled antisense control (FIG. 5a, b and FIG. 21). Ad-Cre infection of RPE cells isolated from Dicer1$^{f/f}$ mice resulted in reduced cell viability, and this was blocked by antisense oligonucleotides targeting both B1 and B2 repeat RNAs but not by a scrambled antisense control (FIG. 5c, d). Subretinal administration of antisense oligonucleotides that reduced accumulation of B1 and B2 RNAs also inhibited RPE degeneration in Dicer1$^{f/f}$ mice treated with AAV1-BEST1-Cre (FIG. 5e, f), providing evidence of in vivo functional rescue.

The present inventors tested whether Alu inhibition also rescued miRNA expression deficits as a potential explanation for the functional rescue of RPE degeneration induced by DICER1 depletion. As expected, DICER1 knockdown in human RPE cells reduced the abundance of numerous miRNAs including let-7a, which is ubiquitously expressed, miR-184, miR-204/211, and miR-221/222, which are enriched in the RPE, and miR-320a, and miR-484 and miR-877, which are DROSHA/DGCR8-independent and DICER1-dependent (FIG. 5g). However, inhibition of Alu RNA did not lead to recovery of miRNA expression in these DICER1-depleted cells. Thus the rescue of RPE cell viability by Alu RNA inhibition despite the persistence of global miRNA expression deficits argues that RPE degeneration induced by DICER1 deficit is due to Alu RNA accumulation and not miRNA dysregulation.

These data, taken together, support a model in which primary Alu transcripts are responsible for the observed RPE degeneration. Whether similar pathology can also result from upregulation of as yet undefined Pol II transcripts with embedded Alu sequences is an intriguing possibility that may be addressed in future studies. Importantly, the present inventors show here that primary Alu transcripts are elevated in human disease, that Alu transcripts recapitulate disease in relevant experimental models, and that targeted suppression of Alu transcripts successfully inhibits this pathology. These observations have direct relevance for clinical strategies to prevent and treat geographic atrophy.

Discussion

The findings elucidate a critical cell survival function for DICER1 by functional silencing of toxic Alu transcripts. This unexpected function suggests that RNAi-independent mechanisms should be considered in interpreting the phenotypes of systems in which Dicer1 is dysregulated. For example, it would be interesting to test the speculation that Dicer1 ablation induced cell death in mouse neural retina[32] and heart[33] might also involve B1/B2 RNA accumulation. More broadly, recognition of DICER1 's hitherto unidentified function as an important controller of transcripts derived from the most abundant repetitive elements in the human and mouse genomes can illuminate new functions for RNases in cytoprotective surveillance. DICER1 expression is reduced in geographic atrophy and partial loss of DICER promotes RPE degeneration; thus the present inventors could speculate that loss of heterozygosity in DICER1 may underlie the development of geographic atrophy, similar to its function as a haploinsufficient tumor suppressor[34-36].

This also is, to our knowledge, the first example of how Alu could cause a human disease via direct RNA cytotoxicity rather than by inducing chromosomal DNA rearrangements or insertional mutagenesis through retrotransposition, which have been implicated in diseases such as α-thalassemia[37], colon cancer[38], hypercholesterolemia[39,40], and neurofibromatosis[41]. Future studies can be employed to determine the precise chromosomal locus of the Alu RNA elements that accumulate in geographic atrophy and the nature of transcriptional and post-transcriptional machinery that enable their biogenesis.

In addition to processing miRNAs[3], DICER1 has been implicated in heterochromatin assembly[42,43]. Since Alu repeat elements are abundant within heterochromatin[44], it would be interesting to investigate whether perturbations in centromeric silencing also underlie the pathogenesis of geographic atrophy. Indeed, the finding that chromatin remodelling at Alu repeats can regulate miRNA expression[45] raises the intriguing possibility of other types of regulatory intersections between DICER1 and Alu. It also remains to be investigated whether centromeric satellite repeats that have been described to accumulate in Dicer1-null mouse embryonic stem cells[46,47] might be involved in the pathogenesis of geographic atrophy.

In the mouse germline, Dicer1 has been implicated in the generation of endogenous small interfering RNAs (endo-siRNAs) from repeat elements[48,49]. If this process is conserved in mammalian somatic tissues, it would be interesting to learn whether endo-siRNAs serve a homeostatic function in preventing the development of geographic atrophy. A recent study in nematodes demonstrated that caspases can cleave Dicer1 and convert it into a DNase that promotes apoptosis[50]. The finding that Alu RNA can induce caspase activation therefore introduces the possibility of bidirectional regulation between DICER1 and Alu that could trigger feed-forward loops that further amplify the disease state.

Figure 30:
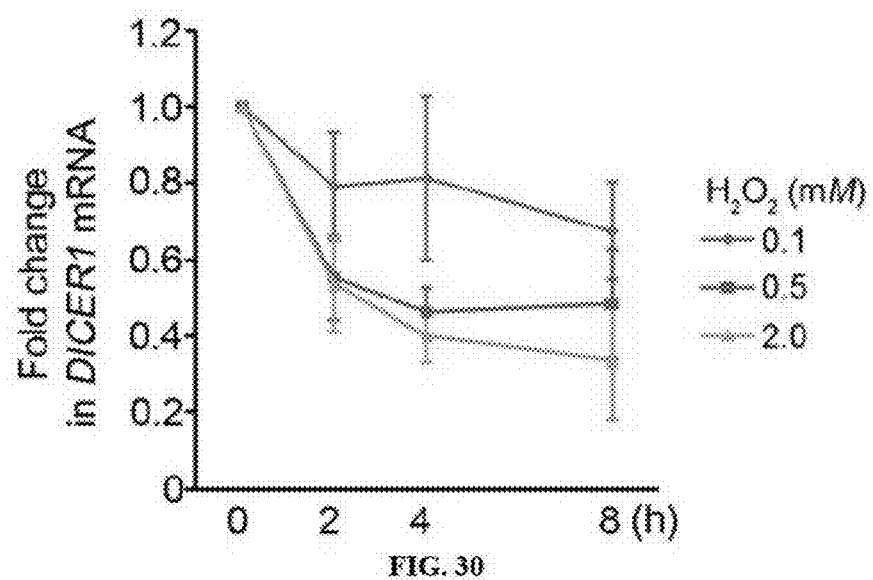
FIG. 30 Oxidative stress downregulates DICER1 in human RPE cells. Human retinal pigmented epithelium (RPE) cells exposed to varying concentrations of hydrogen peroxide ($H_2O_2$) display a dose- and time-dependent reduction in DICER1 mRNA abundance, as monitored by real-time RT-PCR and normalized to 18S rRNA levels. n=3.

The inciting events that trigger an RPE-specific reduction of DICER1 in patients with geographic atrophy remain to be determined. Potential culprit could include oxidative stress, which is postulated to underlie AMD pathogenesis[2], as the present inventors found that exposure to hydrogen peroxide downregulates DICER1 in human RPE cells (FIG. 30). While the upstream triggers of DICER1 dysregulation and the possible role of other DICER-dependent, DROSHA/DGCR8-independent small RNAs in geographic atrophy await clarification, the ability of Alu RNA antisense oligonucleotides to inhibit RPE cell death induced by DICER1 depletion provides a rationale to investigate Alu RNA inhibition or DICER1 augmentation as potential therapies for geographic atrophy.

Additional Notes

Dicer1 mRNA levels are not modulated in multiple mouse models of retinal degeneration including light damage[53,54], hyperoxia, [55]retinal detachment[53,56], Crx$^{-/-}$ mice[57], Rslh$^{-/-}$ mice[58], rd1 mice[59,60], cpfl1 mice[61], or Mitf mice[62]. Dicer1 abundance also is not reduced in mouse models of cellular stress in the retina including exposure to advanced glycation endproducts[63] or retinal detachment[64]. Therefore, Dicer1 downregulation is not a generic late-stage stress response in the retina.

Materials and Methods

Animals

All animal experiments were approved by institutional review committees and the Association for Research in Vision and Ophthalmology. C57Bl/6J and Dicer1$^{f/f}$ mice were purchased from The Jackson Laboratory. Transgenic mice that express Cre recombinase in the retinal pigmented epithelium under the control of the human bestrophin-1 promoter (BEST1 Cre mice), DGCR8$^{f/f}$, Drosha$^{f/f}$, Tarbp2$^{-/-}$, Ccl2$^{-/-}$ Ccr2$^{-/-}$, and Cp$^{-/-}$ Heph$^{-/-}$ mice have been previously described[65-71]. Ago2$^{f/f}$ mice[72] and mice deficient in Ago1, Ago3, or Ago4 (ref. 73) were generously provided by A. Tarakhovsky. For all procedures, anaesthesia was achieved by intraperitoneal injection of 50 mg/kg ketamine hydrochloride (Ft. Dodge Animal Health) and 10 mg/kg xylazine (Phoenix Scientific), and pupils were dilated with topical 1% tropicamide (Alcon Laboratories).

Fundus Photography.

Retinal photographs of dilated mouse eyes were taken with a TRC-50 IX camera (Topcon) linked to a digital imaging system (Sony).

Human Tissue.

Donor eyes or ocular tissues from patients with geographic atrophy due to AMD or patients without AMD were obtained from various eye banks in Australia and the United States of America. These diagnoses were confirmed by dilated ophthalmic examination prior to acquisition of the tissues or eyes or upon examination of the eye globes post mortem. The study followed the guidelines of the Declaration of Helsinki Institutional review boards granted approval for allocation and histological analysis of specimens.

Immunolabeling.

Human eyes fixed in 2-4% paraformaldehyde were prepared as eyecups, cryoprotected in 30% sucrose, embedded in optimal cutting temperature compound (Tissue-Tek OCT; Sakura Finetek), and cryosectioned into 10 μm sections. Depigmentation was achieved using 0.25% potassium permanganate and 0.5% oxalic acid. Immunohistochemical staining was performed with the mouse antibody against dsRNA (1:1,000, clone J2, English & Scientific Consulting) or rabbit antibody against human DICER1 (1:100, Santa Cruz Biotechnology). Isotype IgG was substituted for the primary antibody to assess the specificity of the staining Bound antibody was detected with biotin-conjugated secondary antibodies (Vector Laboratories). Slides were further incubated in alkaline phosphatase-streptavidin solution (Invitrogen) and the enzyme complex was visualized by Vector Blue (Vector Laboratories). Levamisole (Vector Laboratories) was used to block endogenous alkaline phosphatase activity. Slides were washed in PBS, rinsed with deionized water, air-dried, and then mounted in Clear Mount (EMS). Mouse RPE/choroid flat mounts were fixed with 4% paraformaldehyde or 100% methanol and stained with rabbit antibodies against human zonula occludens-1 (1:100, Invitrogen), Cre recombinase (1:1000, EMD4Biosciences), or human cleaved caspase-3 (1:200, Cell Signaling) and visualized with Alexa594- or Cy5-conjugated secondary antibodies. Both antibodies are cross-reactive against the mouse homologues. Primary human RPE cells were grown to 70-80% confluency in chamber slides (Lab-Tek). After 24 h of transfection with pAlu or pUC19, cells were fixed in acetone for 10 min at −20° C. Cells were blocked with PBS-3% BSA and incubated with mouse antibody against dsRNA (1:500, clone J2) overnight at 4° C. and visualized with Alexa Fluor 488-conjugated secondary antibodies. For DICER1 staining, cells were fixed in methanol/acetone (7:3) for 30 min on ice, blocked with PBS-3% BSA-5% FBS, incubated with rabbit antibody against human DICER1 (1:100, Santa Cruz Biotechnology) overnight at 4° C., and visualized with goat-anti-rabbit Alexa Fluor 594-conjugated secondary antibodies. After DAPI counterstaining, slides were cover slipped in Vectashield (Vector Laboratories). Images were obtained using the Leica SP-5 or Zeiss Axio Observer Z1 microscopes.

Histology.

Mouse eyes were fixed with 4% paraformaldehyde and 3.5% glutaraldehyde, postfixed in 2% osmium tetroxide, and dehydrated in ethanol and embedded. Semi-thin (1 μm) sections were cut and stained with toluidine blue. Bright field images were obtained using the Zeiss Axio Observer Z1 microscope.

Subretinal Injection.

Subretinal injections (1 μL) in mice were performed using a Pico-Injector (PLI-100, Harvard Apparatus). In vivo transfection of plasmids coding for DICER1 (ref. 74), Alu Ya5 (ref. 75), Alu Yb9 (ref. 76), 7SL RNA (ref. 77), pri-miR29b1 (Addgene), or pri-miR26a2 (Addgene) and bovine tRNA (Sigma-Aldrich) (0.5 mg/mL) was achieved using 10% Neuroporter (Genlantis). AAV1-BEST1-Cre[78] or AAV1-BEST1-GFP were injected at $1.0 \times 10^{11}$ pfu/mL and recombinant Alu RNAs (1: a single RNA strand of 281 nucleotides whose sequence is that of the cDNA clone TS 103 (ref 51) and folds into a defined secondary structure identical to a Pol III derived transcript; 2: a single RNA strand of 302 nucleotides whose sequence is identical to that of a clone isolated from the RPE of a human eye with geographic atrophy that folds into a defined secondary structure identical to a Pol III derived transcript; or 3: a fully complementary dsRNA version of this 302 nucleotide long sequence that mimics a Pol II derived transcript) was injected at 0.3 mg/mL. Cell-permeating cholesterol conjugated-B1/B2 antisense oligonucleotides (as) (5'-TCAGATCTCGTTACGGATGGTT-GTGA-3') or cholesterol conjugated-control as (5'-TTGGTACGCATACGTGTTGACTGTGA-3') (both from Integrated DNA Technologies) were injected (2 μg in 1 μL) 10 days after AAV1-BEST1-Cre was injected in Dicer1$^{f/f}$ mice.

Isolation of dsRNA.

Human eyes were stored in RNAlater (Ambion). Tissue extracts were prepared by lysis in buffer containing 50 mM Tris-HCl, pH 8, 150 mM NaCl, 1% Nonidet P-40, protease and phosphatase inhibitors (complete mini EDTA-free, protease inhibitor and phosphatase inhibitor cocktail tablets, Roche), and RNase inhibitor (SUPERase-In, Ambion). After homogenization using bullet blender (Nextadvance) and centrifugation, immunoprecipitations were performed by adding 40 μg of mouse antibody against dsRNA (clone J2) for 16 h at 4° C. Immunocomplexes were collected on protein A/G agarose (Thermoscientific) and dsRNA species were separated and isolated using Trizol (Invitrogen) according to the manufacturer's instructions.

Ligation of dsRNA and Anchor Primer.

An anchor primer (PC3-T7 loop, 5'-p-GGATC-CCGGGAATTCGGTAATACGACTCACTATATTTT-TATAGTGAGTCGTATTA-OH-3', 200-400 ng, IDT)[79,80] was ligated to dsRNA (200-400 ng) in 50 mM HEPES/NaOH, pH 8 (vWR), 18 mM MgCl$_2$ (Invitrogen), 0.01% BSA (Fisher Scientific), 1 mM ATP (Roche), 3 mM DTT (Fluka), 10% DMSO (Finnzymes), 20% PEG 6000 (Alfa Aesar), and 30U T4 RNA ligase (Ambion). Ligation was performed at 37° C. for 16 h, and ligated dsRNA was purified by MinElute Gel extraction columns (Qiagen).

Sequence-Independent cDNA Synthesis.

After denaturation, ligated dsRNA was reverse transcribed in a RT reaction containing 50 mM Tris-HCl, pH 8.3, 10 mM MgCl$_2$, 70 mM KCl, 30 mM β-mercaptoethanol, 1 mM dNTPs and 15U cloned AMV reverse transcriptase (Invitrogen). The mixture was incubated in a thermal cycler (Eppendorf) at 42° C. for 45 min followed by 55° C. for 15 min.

Polymerase Chain Reaction (PCR) Amplification.

Amplification of cDNA was performed using primer PC2 (5'-p-CCGAATTCCCGGGATCC-3', IDT) in a reaction buffer containing 5 µL cDNA and 40 µL Platinum PCR SuperMix (Invitrogen). The PCR cycling parameters consisted of one step of 72° C. for 1 min to fill incomplete cDNA ends and produce intact DNA, followed by one step of initial denaturation (94° C., 2 min), 39 cycles of 94° C. for 30 s, 53° C. for 30 s, and 72° C. for 1 min, and a final extension step of 72° C. for 10 min. In vitro transcribed dsRNAs of varying lengths (325 bp, 1 and 2 kb) were used as positive controls.

Cloning and Sequencing.

The amplified cDNA products were incubated with 1U calf intestinal alkaline phosphatase (Invitrogen) at 37° C. for 5 min to remove the 5'-phosphate group, separated on a low-melting point agarose gel (1%) and purified using Qiaquick gel extraction kit (Qiagen). The purified dephosphorylated cDNA fragments were cloned in PCRII TOPO vector (Invitrogen) and sequenced using M13 forward (−20) and M13 reverse primers at the University of Kentucky Advanced Genetic Technologies Center using multi-colour fluorescence based DNA sequencer (ABI 3730x1). Sequences were assembled using ContigExpress from vector NTI Advance. The homology of the isolated cDNA sequences to known Alu consensus sequences was determined using the CENSOR server[81] (a WU-BLAST-powered database of repetitive elements (http://www.girinst.org/censor). For each cDNA sequence, the homologous region of the query was aligned to the consensus Alu sequence using BLASTn[82] (http://www.ncbi.nlm.nih.gov/BLAST). Multiple sequence alignment was performed using ClustalW2 (http://www.ebi.ac.uk/Tools/clustalw2). The consensus sequences have been deposited in GenBank under the accession numbers HN176584 and HN176585.

Alu RNA Synthesis.

The present inventors synthesized two Alu RNAs: a 281 nt Alu sequence originating from the cDNA clone TS 103 which is known to be expressed in human cells[51] and a 302 nt Alu sequence isolated from the RPE of a human eye with geographic atrophy. Both of these Alu RNAs were synthesized using a RNA polymerase T7 promoter and runoff transcription followed by gel purification as previously described[83]. This yields single stranded RNAs that fold into a defined secondary structure identical to Pol III derived transcripts. The present inventors also synthesized a fully complementary dsRNA form (resembling a Pol II derived transcript) of the 302 nt human geographic atrophy Alu using linearized PCRII TOPO plasmid templates using T7 or SP6 RNA polymerases (MegaScript, Ambion) according to the manufacturer's recommendations. After purification, equal molar amount of each transcript were combined and heated at 95° C. for 1 min, cooled and then annealed at room temperature for 24 h. The Alu dsRNA was precipitated, suspended in water and analyzed on 1.4% non-denaturing agarose gel using the single-stranded complementary strands as controls.

Real-Time PCR.

Total RNA was extracted from tissues or cells using Trizol reagent (Invitrogen) according to manufacturer's recommendations and were treated with RNase free DNase (Ambion). Total RNA (1 µg) was reverse transcribed as previously described[70] using qScript cDNA SuperMix (Quanta Biosciences). The RT products (cDNA) were amplified by real-time quantitative PCR (Applied Biosystems 7900 HT Fast Real-Time PCR system) with Power SYBR green Master Mix. Oligonucleotide primers specific for DICER1 (forward 5'-CCCGGCTGAGAGAACTTACG-3' and reverse 5'-CTGTAACTTCGACCAACACCTTTAAA-3'), DROSHA (forward 5'-GAACAGTTCAACCCCGATGTG-3' and reverse 5'-CTCAACTGTGCAGGGCGTATC-3'), DGCR8 (forward 5'-TCTGCTCCTTAGCCCTGTCAGT-3' and reverse 5'-CCAACACTCCCGCCAAAG-3'), EIF2C2 (forward 5'-GCACGGAAGTCCATCTGAAGTC-3' and reverse 5'-CCGGCGTCTCTCGAGATCT-3'), human 18S rRNA (forward 5'-CGCAGCTAGGAATAATGGAATAGG-3' and reverse 5'-GCCTCAGTTCCGAAAACCAA-3'), Alu (forward 5'-CAACATAGTGAAACCCCGTCTCT-3' and reverse 5'-GCCTCAGCCTCCCGAGTAG-3'), LINE L1.3 (ORF2) (forward 5'-CGGTGATTTCTGCATTTCCA-3' and reverse 5'-TGTCTGGCACTCCCTAGTGAGA-3'), HERV-WE1 (forward 5'-GCCGCTGTATGACCAGTAGCT-3' and reverse 5'-GGGACGCTGCATTCTCCAT-3'), human Ro-associated Y3 (hY3) (forward 5'-CCGAGTGCAGTGGT-GTTTACA-3' and reverse 5'-GGAGTGGA-GAAGGAACAAAGAAATC-3'), 7SL (forward 5'-CGGCATCAATATGGTGACCT-3' and reverse 5'-CT-GATCAGCACGGGAGTTTT-3'), B1 (forward 5'-TGC-CTTTAATCCCAGCACTT-3' and reverse 5'-GCTGCTCA-CACAAGGTTGAA-3'), B2 (forward 5'-GAGTTCAAATCCCAGCAACCA-3' and reverse 5'-AAGAGGGTCTCAGATCTTGTTACAGA-3'), cytoplasmic B2 (forward 5'-GCCCTGTTACAATTGGCTTT-3' and reverse 5'-GTGGTTGCTGGGATTTGAAC-3'), Dicer1 (forward 5'-CCCACCGAGGTGCATGTT-3' and reverse 5'-TAGTGGTAGGAGGCGTGTGTAAAA-3'), mouse 18S rRNA (forward 5'-TTCGTATTGCGC-CGCTAGA-3' and reverse 5'-CTTTCGCTCTGGTC-CGTCTT-3') were used. The QPCR cycling conditions were 50° C. for 2 min, 95° C. for 10 min followed by 40 cycles of a two-step amplification program (95° C. for 15 s and 58° C. for 1 min). At the end of the amplification, melting curve analysis was applied using the dissociation protocol from the Sequence Detection system to exclude contamination with unspecific PCR products. The PCR products were also confirmed by agarose gel and showed only one specific band of the predicted size. For negative controls, no RT products were used as templates in the QPCR and verified by the absence of gel-detected bands. Relative expressions of target genes were determined by the $2^{-\Delta\Delta C_t}$ method.

miRNA PCR.

miRNA abundance was quantified using the All-in-One™ miRNA qRT-PCR Detection Kit (GeneCopoeia). Briefly, total RNA was polyadenylated and reverse transcribed using a poly dT-adaptor primer. Quantitative RT-PCR was carried out using a miRNA-specific forward primer and universal reverse primer. PCR products were subjected to dissociation curve and gel electrophoresis analyses to ensure that single, mature miRNA products were amplified. Data were normalized to ACTB levels. The forward primers for the miRNAs were as follows: miR-184 (5'-TGGACGGAGAACTGA-TAAGGGT-3'); miR-221/222 (5'-AGCTACATCTGGC-TACTGGGT-3'); miR-204/211 (5'-TTCCCTTTGTCATC-CTTCGCCT-3'); miR-877 (5'-GTAGAGGAGATGGCGCAGGG-3'); miR-320a (5'-AAAAGCTGGGTTGAGAGGGCGA-3'); miR-484 (5'-TCAGGCTCAGTCCCCTCCCGAT-3'); let-7a (5'-TGAGGTAGTAGGTTGTATAGTT-3'). The reverse primers were proprietary (Genecopoeia). The primers for ACTB were forward (5'-TGGATCAGCAAGCAGGAG-TATG-3') and reverse (5'-GCATTTGCGGTGGACGAT-3').

Dot Blot (Immuno-Dot Binding).

Increasing amounts of Alu RNA were spotted onto hybond-N+ positively charged nylon membrane (Amersham) and UV cross-linked. After blocking, the membranes were incubated with mouse antibody against dsRNA (1:1,000, clone J2) for 1 h at RT. The peroxidase-conjugated goat anti-mouse secondary antibody (1:5,000, Sigma) was used for 1 h at RT. After several washes, the signals were visualized by enhanced chemiluminescence (ECL plus, Amersham). In vitro transcribed dsRNAs of different length were used as positive controls. Transfer and ribosomal RNAs were used as negative controls.

Northern Blot.

Total RNA from normal and diseased macular RPE was extracted as described above using Trizol. RNA integrity and quality was assessed using 1% agarose gel electrophoresis and RNA concentrations and purity were determined for each sample by NanoDrop 1000 spectrophotometer V3.7 (Thermo Fisher Scientific). dsRNA (2 µg) was separated on denaturing 15% PAGE-urea ready gel (Bio-Rad), and total RNA (10 µg) was separated by size on 1% agarose, 0.7M formaldehyde gels and visualized on an ultraviolet transilluminator to ensure consistent loading between groups and to record the distance of migration of the 18S and 28S rRNA bands. dsRNA ladder (21-500 bp, New England BioLabs) and RNA ladder (0.1-2 kb, Invitrogen) were used as markers. Gels were then transferred to a positively charged Nylon membrane (Hybond-N+, GE Healthcare Bio-Sciences) by vacuum blotting apparatus (VacuGene XL Vacuum Blotting System, GE Healthcare Bio-Sciences). The RNAs were crosslinked to the membranes by ultraviolet irradiation and baked at 80° C. for 20-30 min. Membranes were hybridized with ($\alpha$-$^{32}$P)-dCTP-labeled DNA Alu probe at 42° C. overnight. On the following day, the membranes were rinsed twice with 1×SSC, 0.1% SDS at 55° C. Each wash was for 20 min, and then membranes were subjected to storage in a phosphor autoradiography cassette. Hybridization signals were determined by using Typhoon phosphorimager (GE Healthcare Bio-Sciences). The 7SL probe was synthesized by PCR amplification of a 7SL RNA plasmid[77, 84] with the following primers (forward 5'-ATCGGGTGTC-CGCACTAAG-3' and reverse 5'-ATCAG-CACGGGAGTTTTGAC-3') designed to amplify a 128-bp fragment within the S-region that is not contained in Alu. For visualization of U6, membranes were stripped and blotted again using the High Sensitive MiRNA Northern Blot Assay Kit (Signosis) according to the manufacturer's instructions.

Western Blot.

Tissues were homogenized in lysis buffer (10 mM Tris base, pH 7.4, 150 mM NaCl, 1 mM EDTA, 1 mM EGTA, 1% Triton X-100, 0.5% NP-40, protease and phosphatase inhibitor cocktail (Roche)). Protein concentrations were determined using a Bradford assay kit (Bio-Rad) with bovine serum albumin as a standard. Proteins (40-100 µg) were run on 4-12% Novex Bis-Tris gels (Invitrogen). The transferred membranes were blocked for 1 h at RT and incubated with antibodies against DICER1 (1:1,000, ref. 85; or 1:200, Santa Cruz Biotechnology) at 4° C. overnight. Protein loading was assessed by immunoblotting using an anti-Tubulin antibody (1:1,000; Sigma-Aldrich). The secondary antibodies were used (1:5,000) for 1 h at RT. The signal was visualized by enhanced chemiluminescence (ECL Plus) and captured by VisionWorksLS Image Acquisition and Analysis software (Version 6.7.2, UVP, LLC). Densitometry analysis was performed using ImageJ (NIH). The value of 1 was arbitrarily assigned for normal eye samples.

DICER1 Cleavage.

The ability of DICER1 to cleave Alu RNA was tested using Recombinant Human Dicer Enzyme Kit (Genlantis) according to the manufacturer's instructions. The products of the digestion were purified for the in vivo injection using RNA Purification Column (Genlantis).

Cell Culture.

All cell lines were cultured at 37° C. and 5% $CO_2$. Primary mouse RPE cells were isolated as previously described[86] and grown in Dulbecco Modified Eagle Medium (DMEM) supplemented with 10% FBS and standard antibiotics concentrations. Primary human RPE cells were isolated as previously described[87] and maintained in DMEM supplemented with 20% FBS and antibiotics. Parental HCT116 and isogenic Dicer$^{ex5}$ cells[25] were cultured in McCoy's 5A medium supplemented with 10% FBS.

Transient Transfection.

Human and mouse RPE cells were transfected with pUC19, pAlu, pCDNA3.1/Dicer1-FLAG, pCDNA3.1, DICER1 antisense oligonucleotide (as) (5'-GCUGAC-CTTTTTGCTUCUCA-3'), B1/B2 as (5'-TCAGATCTCGT-TACGGATGGTTGTGA-3'), control (for DICER1 and B1/B2) as (5'-TTGGTACGCATACGTGTTGACTGTGA-3'), Alu as (5'-CCCGGGTTCACGCCATTCTCCTGC-CTCAGCCTCACGAGTAGCTGGGACTACAGGCGC CCGACACCACTCCCGGCTAATTTTTTGTATTTTT-3'), control (for Alu) as (5'-GCATGGCCAGTCCATTGATCT-TGCACGCTTGCCTAGTACGCTCCTCAACCTATC-CTCC TAGCCCGTTACTTGGTGCCACCGGCG-3') using Lipofectamine 2000 (Invitrogen) or Oligofectamine (Invitrogen) according to the manufacturer's instructions.

Adenoviral Infection.

Cells were plated at density of 15×10$^3$/cm$^2$ and after 16 h, at approximately 50% confluence, were infected with AdCre or AdNull (Vector Laboratories) with a multiplicity of infection of 1,000.

RNA Polymerase Inhibition.

Human RPE cells were transfected with DICER1 or control antisense oligonucleotides using Lipofectamine 2000. After a change of medium at 6 h, the cells were incubated with 45 µM tagetitoxin (Epicentre Technologies, Tagetin) or 10 µg/ml a-amanitin (Sigma-Aldrich) and the total RNA was collected after 24 h.

Cell Viability.

MTS assays were performed using the CellTiter 96 A Queous One Solution Cell Proliferation Assay (Promega) in according to the manufacturer's instructions.

Caspase-3 Activity.

Sub-confluent human RPE cells were treated with PBS or Alu RNA at different concentrations in 2% FBS medium for 8 h. The caspase-3 activity was measured using Caspase-3 Fluorimetric Assay (R&D Systems) according to the manufacturer's instructions.

Oxidative Stress.

Confluent human RPE cells were exposed to hydrogen peroxide (0-2 mM, Fisher Scientific).

Statistics.

Results are expressed as mean±SEM, with P<0.05 considered statistically significant. Differences between groups were compared by using Mann-Whitney U test or Student t test, as appropriate, and 2-tailed P values are reported.

Throughout this document, various references are mentioned. All such references are incorporated herein by reference, including the references set forth in the following list:

REFERENCES

1. Ferrara, N. Vascular endothelial growth factor and age-related macular degeneration: from basic science to therapy. *Nat Med* 16, 1107-1111 (2010).
2. Ambati, J., Ambati, B. K., Yoo, S. H., Ianchulev, S. & Adamis, A. P. Age-related macular degeneration: etiology, pathogenesis, and therapeutic strategies. *Surv Ophthalmol* 48, 257-293 (2003).
3. Bernstein, E., Caudy, A. A., Hammond, S. M. & Hannon, G. J. Role for a bidentate ribonuclease in the initiation step of RNA interference. *Nature* 409, 363-366 (2001).
4. Batzer, M. A. & Deininger, P. L. Alu repeats and human genomic diversity. *Nat Rev Genet* 3, 370-379 (2002).
5. Gregory, R. I. et al. The Microprocessor complex mediates the genesis of microRNAs. *Nature* 432, 235-240 (2004).
6. Liu, J. et al. Argonaute2 is the catalytic engine of mammalian RNAi. *Science* 305, 1437-1441 (2004).
7. Meister, G. et al. Human Argonaute2 mediates RNA cleavage targeted by miRNAs and siRNAs. *Mol Cell* 15, 185-197 (2004).
8. Wiesen, J. L. & Tomasi, T. B. Dicer is regulated by cellular stresses and interferons. *Mol Immunol* 46, 1222-1228 (2009).
9. Ambati, J. et al. An animal model of age-related macular degeneration in senescent Ccl-2- or Ccr-2-deficient mice. *Nat Med* 9, 1390-1397 (2003).
10. Takeda, A. et al. CCR3 is a target for age-related macular degeneration diagnosis and therapy. *Nature* 460, 225-230 (2009).
11. Hahn, P. et al. Disruption of ceruloplasmin and hephaestin in mice causes retinal iron overload and retinal degeneration with features of age-related macular degeneration. *Proc Natl Acad Sci USA* 101, 13850-13855 (2004).
12. Harfe, B. D., McManus, M. T., Mansfield, J. H., Hornstein, E. & Tabin, C. J. The RNaseIII enzyme Dicer is required for morphogenesis but not patterning of the vertebrate limb. *Proc Natl Acad Sci USA* 102, 10898-10903 (2005).
13. Iacovelli, J. et al. Generation of cre transgenic mice with postnatal RPE-specific ocular expression. *Invest Ophthalmol Vis Sci*, In press (2010).
14. Alexander, J. J. & Hauswirth, W. W. Adeno-associated viral vectors and the retina. *Adv Exp Med Biol* 613, 121-128 (2008).
15. Chong, M. M., Rasmussen, J. P., Rudensky, A. Y. & Littman, D. R. The RNaseIII enzyme Drosha is critical in T cells for preventing lethal inflammatory disease. *J Exp Med* 205, 2005-2017 (2008).
16. Yi, R. et al. DGCR8-dependent microRNA biogenesis is essential for skin development. *Proc Natl Acad Sci USA* 106, 498-502 (2009).
17. O'Carroll, D. et al. A Slicer-independent role for Argonaute 2 in hematopoiesis and the microRNA pathway. *Genes Dev* 21, 1999-2004 (2007).
18. Chong, M. M. et al. Canonical and alternate functions of the microRNA biogenesis machinery. *Genes Dev* 24, 1951-1960 (2010).
19. Babiarz, J. E., Ruby, J. G., Wang, Y., Bartel, D. P. & Blelloch, R. Mouse ES cells express endogenous shRNAs, siRNAs, and other Microprocessor-independent, Dicer-dependent small RNAs. *Genes Dev* 22, 2773-2785 (2008).
20. Schaefer, A. et al. Argonaute 2 in dopamine 2 receptor-expressing neurons regulates cocaine addiction. *J Exp Med* 207, 1843-1851 (2010).
21. Diederichs, S. & Haber, D. A. Dual role for argonautes in microRNA processing and posttranscriptional regulation of microRNA expression. *Cell* 131, 1097-1108 (2007).
22. Kaneda, M., Tang, F., O'Carroll, D., Lao, K. & Surani, M. A. Essential role for Argonaute2 protein in mouse oogenesis. *Epigenetics Chromatin* 2, 9 (2009).
23. Su, H., Trombly, M. I., Chen, J. & Wang, X. Essential and overlapping functions for mammalian Argonautes in microRNA silencing. *Genes Dev* 23, 304-317 (2009).
24. Chendrimada, T. P. et al. TRBP recruits the Dicer complex to Ago2 for microRNA processing and gene silencing. *Nature* 436, 740-744 (2005).
25. Cummins, J. M. et al. The colorectal microRNAome. *Proc Natl Acad Sci USA* 103, 3687-3692 (2006).
26. Schonborn, J. et al. Monoclonal antibodies to double-stranded RNA as probes of RNA structure in crude nucleic acid extracts. *Nucleic Acids Res* 19, 2993-3000 (1991).
27. Kato, H. et al. Length-dependent recognition of double-stranded ribonucleic acids by retinoic acid-inducible gene-I and melanoma differentiation-associated gene 5. *J Exp Med* 205, 1601-1610 (2008).
28. Saleh, M. C. et al. The endocytic pathway mediates cell entry of dsRNA to induce RNAi silencing. *Nat Cell Biol* 8, 793-802 (2006).
29. Yang, Z. et al. Toll-like receptor 3 and geographic atrophy in age-related macular degeneration. *N Engl J Med* 359, 1456-1463 (2008).
30. Dunaief, J. L., Dentchev, T., Ying, G. S. & Milam, A. H. The role of apoptosis in age-related macular degeneration. *Arch Ophthalmol* 120, 1435-1442 (2002).
31. Davis, T. H. et al. Conditional loss of Dicer disrupts cellular and tissue morphogenesis in the cortex and hippocampus. *J Neurosci* 28, 4322-4330 (2008).
32. Damiani, D. et al. Dicer inactivation leads to progressive functional and structural degeneration of the mouse retina. *J Neurosci* 28, 4878-4887 (2008).
33. Chen, J. F. et al. Targeted deletion of Dicer in the heart leads to dilated cardiomyopathy and heart failure. *Proc Natl Acad Sci USA* 105, 2111-2116 (2008).
34. Merritt, W. M. et al. Dicer, Drosha, and outcomes in patients with ovarian cancer. *N Engl J Med* 359, 2641-2650 (2008).
35. Kumar, M. S. et al. Dicer1 functions as a haploinsufficient tumor suppressor. *Genes Dev* 23, 2700-2704 (2009).
36. Hill, D. A. et al. DICER1 mutations in familial pleuropulmonary blastoma. *Science* 325, 965 (2009).

37. Nicholls, R. D., Fischel-Ghodsian, N. & Higgs, D. R. Recombination at the human alpha-globin gene cluster: sequence features and topological constraints. *Cell* 49, 369-378 (1987).
38. Nystrom-Lahti, M. et al. Founding mutations and Alu-mediated recombination in hereditary colon cancer. *Nat Med* 1, 1203-1206 (1995).
39. Lehrman, M. A. et al. Mutation in LDL receptor: Alu-Alu recombination deletes exons encoding transmembrane and cytoplasmic domains. *Science* 227, 140-146 (1985).
40. Lehrman, M. A., Goldstein, J. L., Russell, D. W. & Brown, M. S. Duplication of seven exons in LDL receptor gene caused by Alu-Alu recombination in a subject with familial hypercholesterolemia. *Cell* 48, 827-835 (1987).
41. Wallace, M. R. et al. A de novo Alu insertion results in neurofibromatosis type 1. *Nature* 353, 864-866 (1991).
42. Volpe, T. A. et al. Regulation of heterochromatic silencing and histone H3 lysine-9 methylation by RNAi. *Science* 297, 1833-1837 (2002).
43. Hall, I. M. et al. Establishment and maintenance of a heterochromatin domain. *Science* 297, 2232-2237 (2002).
44. Prades, C., Laurent, A. M., Puechberty, J., Yurov, Y. & Roizes, G. SINE and LINE within human centromeres. *J Mol Evol* 42, 37-43 (1996).
45. Saito, Y. et al. Chromatin remodeling at Alu repeats by epigenetic treatment activates silenced microRNA-512-5p with downregulation of Mc1-1 in human gastric cancer cells. *Oncogene* 28, 2738-2744 (2009).
46. Murchison, E. P., Partridge, J. F., Tam, O. H., Cheloufi, S. & Hannon, G. J. Characterization of Dicer-deficient murine embryonic stem cells. *Proc Natl Acad Sci USA* 102, 12135-12140 (2005).
47. Kanellopoulou, C. et al. Dicer-deficient mouse embryonic stem cells are defective in differentiation and centromeric silencing. *Genes Dev* 19, 489-501 (2005).
48. Tam, O. H. et al. Pseudogene-derived small interfering RNAs regulate gene expression in mouse oocytes. *Nature* 453, 534-538 (2008).
49. Watanabe, T. et al. Endogenous siRNAs from naturally formed dsRNAs regulate transcripts in mouse oocytes. *Nature* 453, 539-543 (2008).
50. Nakagawa, A., Shi, Y., Kage-Nakadai, E., Mitani, S. & Xue, D. Caspase-dependent conversion of Dicer ribonuclease into a death-promoting deoxyribonuclease. *Science* 328, 327-334 (2010).
51. Shaikh, T. H., Roy, A. M., Kim, J., Batzer, M. A. & Deininger, P. L. cDNAs derived from primary and small cytoplasmic Alu (scAlu) transcripts. *J Mol Biol* 271, 222-234 (1997).
52. Sinnett, D., Richer, C., Deragon, J. M. & Labuda, D. Alu RNA transcripts in human embryonal carcinoma cells. Model of post-transcriptional selection of master sequences. *J Mol Biol* 226, 689-706 (1992).
53. Rattner, A., Toulabi, L., Williams, J., Yu, H. & Nathans, J. The genomic response of the retinal pigment epithelium to light damage and retinal detachment. *J Neurosci* 28, 9880-9889 (2008).
54. Huang, H. et al. Identification of mouse retinal genes differentially regulated by dim and bright cyclic light rearing. *Exp Eye Res* 80, 727-739 (2005).
55. Natoli, R., Provis, J., Valter, K. & Stone, J. Gene regulation induced in the C57BL/6J mouse retina by hyperoxia: a temporal microarray study. *Mol Vis* 14, 1983-1994 (2008).
56. Farjo, R., Peterson, W. M. & Naash, M. I. Expression profiling after retinal detachment and reattachment: a possible role for aquaporin-0. *Invest Ophthalmol Vis Sci* 49, 511-521 (2008).
57. Livesey, F. J., Furukawa, T., Steffen, M. A., Church, G. M. & Cepko, C. L. Microarray analysis of the transcriptional network controlled by the photoreceptor homeobox gene Crx. *Curr Biol* 10, 301-310 (2000).
58. Gehrig, A. et al. Genome-wide expression profiling of the retinoschisin-deficient retina in early postnatal mouse development. *Invest Ophthalmol Vis Sci* 48, 891-900 (2007).
59. Hackam, A. S. et al. Identification of gene expression changes associated with the progression of retinal degeneration in the rd1 mouse. *Invest Ophthalmol Vis Sci* 45, 2929-2942 (2004).
60. Punzo, C. & Cepko, C. Cellular responses to photoreceptor death in the rd1 mouse model of retinal degeneration. *Invest Ophthalmol Vis Sci* 48, 849-857 (2007).
61. Schaeferhoff, K. et al. Induction of STAT3-related genes in fast degenerating cone photoreceptors of cpfl1 mice. *Cell Mol Life Sci* 67, 3173-3186 (2010).
62. Gelineau-van Waes, J. et al. Altered expression of the iron transporter Nramp1 (Slc11a1) during fetal development of the retinal pigment epithelium in microphthalmia-associated transcription factor Mitf (mi) and Mitf (vitiligo) mouse mutants. *Exp Eye Res* 86, 419-433 (2008).
63. Tian, J. et al. Advanced glycation endproduct-induced aging of the retinal pigment epithelium and choroid: a comprehensive transcriptional response. *Proc Natl Acad Sci USA* 102, 11846-11851 (2005).
64. Zacks, D. N., Han, Y., Zeng, Y. & Swaroop, A. Activation of signaling pathways and stress-response genes in an experimental model of retinal detachment. *Invest Ophthalmol Vis Sci* 47, 1691-1695 (2006).
65. Chong, M. M., Rasmussen, J. P., Rudensky, A. Y. & Littman, D. R. The RNAseIII enzyme Drosha is critical in T cells for preventing lethal inflammatory disease. *J Exp Med* 205, 2005-2017 (2008).
66. Iacovelli, J. et al. Generation of cre transgenic mice with postnatal RPE-specific ocular expression. *Invest Ophthalmol Vis Sci*, In press (2010).
67. Yi, R. et al. DGCR8-dependent microRNA biogenesis is essential for skin development. *Proc Natl Acad Sci USA* 106, 498-502 (2009).
68. Zhong, J., Peters, A. H., Lee, K. & Braun, R. E. A double-stranded RNA binding protein required for activation of repressed messages in mammalian germ cells. *Nat Genet* 22, 171-174 (1999).
69. Ambati, J. et al. An animal model of age-related macular degeneration in senescent Ccl-2- or Ccr-2-deficient mice. *Nat Med* 9, 1390-1397 (2003).
70. Takeda, A. et al. CCR3 is a target for age-related macular degeneration diagnosis and therapy. *Nature* 460, 225-230 (2009).
71. Hahn, P. et al. Disruption of ceruloplasmin and hephaestin in mice causes retinal iron overload and retinal degeneration with features of age-related macular degeneration. *Proc Natl Acad Sci USA* 101, 13850-13855 (2004).
72. O'Carroll, D. et al. A Slicer-independent role for Argonaute 2 in hematopoiesis and the microRNA pathway. *Genes Dev* 21, 1999-2004 (2007).
73. Schaefer, A. et al. Argonaute 2 in dopamine 2 receptor-expressing neurons regulates cocaine addiction. *J Exp Med* 207, 1843-1851 (2010).
74. Provost, P. et al. Ribonuclease activity and RNA binding of recombinant human Dicer. *EMBO J* 21, 5864-5874 (2002).
75. Bennett, E. A. et al. Active Alu retrotransposons in the human genome. *Genome Res* 18, 1875-1883 (2008).
76. Hagan, C. R., Sheffield, R. F. & Rudin, C. M. Human Alu element retrotransposition induced by genotoxic stress. *Nat Genet* 35, 219-220 (2003).

77. Misra, S., Tripathi, M. K. & Chaudhuri, G. Down-regulation of 7SL RNA expression and impairment of vesicular protein transport pathways by Leishmania infection of macrophages. *J Biol Chem* 280, 29364-29373 (2005).
78. Alexander, J. J. & Hauswirth, W. W. Adeno-associated viral vectors and the retina. *Adv Exp Med Biol* 613, 121-128 (2008).
79. Maan, S. et al. Rapid cDNA synthesis and sequencing techniques for the genetic study of bluetongue and other dsRNA viruses. *J Virol Methods* 143, 132-139 (2007).
80. Potgieter, A. C. et al. Improved strategies for sequence-independent amplification and sequencing of viral double-stranded RNA genomes. *J Gen Virol* 90, 1423-1432 (2009).
81. Kohany, O., Gentles, A. J., Hankus, L. & Jurka, J Annotation, submission and screening of repetitive elements in Repbase: RepbaseSubmitter and Censor. *BMC Bioinformatics* 7, 474 (2006).
82. Altschul, S. F., Gish, W., Miller, W., Myers, E. W. & Lipman, D. J. Basic local alignment search tool. *J Mol Biol* 215, 403-410 (1990).
83. Allen, T. A., Von Kaenel, S., Goodrich, J. A. & Kugel, J. F. The SINE-encoded mouse B2 RNA represses mRNA transcription in response to heat shock. *Nat Struct Mol Biol* 11, 816-821 (2004).
84. Tripathi, M. K. & Chaudhuri, G. Down-regulation of UCRP and UBE2L6 in BRCA2 knocked-down human breast cells. *Biochem Biophys Res Commun* 328, 43-48 (2005).
85. Kanellopoulou, C. et al. Dicer-deficient mouse embryonic stem cells are defective in differentiation and centromeric silencing. *Genes Dev* 19, 489-501 (2005).
86. Yang, P., Tyrrell, J., Han, I. & Jaffe, G. J. Expression and modulation of RPE cell membrane complement regulatory proteins. *Invest Ophthalmol Vis Sci* 50, 3473-3481 (2009).
87. Yang, Z. et al. Toll-like receptor 3 and geographic atrophy in age-related macular degeneration. *N Engl J Med* 359, 1456-1463 (2008).
88. U.S. Patent Application Publication No. 2007/0031417 for Dicer Interaction Proteins and Uses Therefor.
89. U.S. Patent Application Publication No. 2006/0228361 for Dicer Interacting Proteins and Uses Therefor.
90. International Patent Application Publication No. WO 2005/047477 for Interspersed Repetitive Element RNAs as Substrates, Inhibitors, and Delivery Vehicles for RNAi.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. An isolated nucleotide molecule selected from:
a double-stranded RNA molecule that inhibits expression of Alu RNA, wherein a first strand of the double-stranded RNA comprises a sequence selected from SEQ ID NO: 1, 2, 3, 4, 5, and 6 and including about 19 to 25 nucleotides; and
a vector comprising an oligonucleotide that inhibits the expression of Alu RNA, comprising a sequence selected from SEQ ID NO: 22, 23, 24, and 25 and including about 29 to 100 nucleotides; and a vector comprising an oligonucleotide that inhibits the expression of Alu RNA, consisting of the sequence of SEQ ID NO: 26.

2. A method of protecting an RPE cell, comprising administering a nucleotide molecule of claim 1.

* * * * *

SEQUENCE LISTING

```
<160> NUMBER OF SEQ ID NOS: 29

<210> SEQ ID NO 1
<211> LENGTH: 19
<212> TYPE: DNA
<213> ORGANISM: Artificial Sequence
<220> FEATURE:
<223> OTHER INFORMATION: siRNA

<400> SEQUENCE: 1
ctcagcctca cgagtagct                                                      19

<210> SEQ ID NO 2
<211> LENGTH: 19
<212> TYPE: DNA
<213> ORGANISM: Artificial Sequence
<220> FEATURE:
<223> OTHER INFORMATION: siRNA

<400> SEQUENCE: 2
tgggactaca ggcgcccga                                                      19

<210> SEQ ID NO 3
<211> LENGTH: 21
<212> TYPE: DNA
<213> ORGANISM: Artificial Sequence
<220> FEATURE:
<223> OTHER INFORMATION: siRNA

<400> SEQUENCE: 3
gcctcagcct cacgagtagc t                                                   21

<210> SEQ ID NO 4
<211> LENGTH: 21
<212> TYPE: DNA
<213> ORGANISM: Artificial Sequence
<220> FEATURE:
<223> OTHER INFORMATION: siRNA
```

```
<400> SEQUENCE: 4
gctgggacta caggcgcccg a                                              21

<210> SEQ ID NO 5
<211> LENGTH: 21
<212> TYPE: DNA
<213> ORGANISM: Artificial Sequence
<220> FEATURE:
<223> OTHER INFORMATION: siRNA

<400> SEQUENCE: 5
gggactacag gcgcccgaca c                                              21

<210> SEQ ID NO 6
<211> LENGTH: 21
<212> TYPE: DNA
<213> ORGANISM: Artificial Sequence
<220> FEATURE:
<223> OTHER INFORMATION: siRNA

<400> SEQUENCE: 6
acaggcgccc gacaccactc c                                              21

<210> SEQ ID NO 7
<211> LENGTH: 10323
<212> TYPE: DNA
<213> ORGANISM: Homo sapiens

<400> SEQUENCE: 7
cggaggcgcg gcgcaggctg ctgcaggccc aggtgaatgg agtaacctga cagcggggac     60
gaggcgacgg cgagcgcgag gaaatggcgg cggggggcggc ggcgccgggc ggctccggga   120
ggcctgggct gtgacgcgcg cgccggagcg gggtccgatg gttctcgaag gcccgcggcg   180
ccccgtgctg cagtaagctg tgctagaaca aaaatgcaat gaaagaaaca ctggatgaat   240
gaaaagccct gctttgcaac ccctcagcat ggcaggcctg cagctcatga cccctgcttc   300
ctcaccaatg ggtcctttct ttggactgcc atggcaacaa gaagcaattc atgataacat   360
ttatacgcca agaaaatatc aggttgaact gcttgaagca gctctggatc ataataccat   420
cgtctgttta aacactggct cagggaagac atttattgca gtactactca ctaaagagct   480
gtcctatcag atcaggggag acttcagcag aaatggaaaa aggacggtgt tcttggtcaa   540
ctctgcaaac caggttgctc aacaagtgtc agctgtcaga actcattcag atctcaaggt   600 tgggaatac tcaaacctag aagtaaatgc atccttgaca aaagagagat ggaaccaaga   660
gtttactaag caccaggttc tcattatgac ttgctatgtc gccttgaatg ttttgaaaaa   720
tggttactta tcactgtcag acattaacct tttggtgttt gatgagtgtc atcttgcaat   780
cctagaccac ccctatcgag aaattatgaa gctctgtgaa aattgtccat catgtcctcg   840
cattttggga ctaactgctt ccattttaaa tgggaaatgt gatccagagg aattggaaga   900
aaagattcag aaactagaga aaattcttaa gagtaatgct gaaactgcaa ctgacctggt   960
ggtcttagac aggtatactt ctcagccatg tgagattgtg gtggattgtg gaccatttac  1020
tgacagaagt gggctttatg aaagactgct gatggaatta aagaagcac ttaatttat   1080 caatgattgt aatatatctg tacattcaaa agaaagagat tctactttaa tttcgaaaca  1140
gatactatca gactgtcgtg ccgtattggt agttctggga ccctggtgtg cagataaagt  1200
agctggaatg atggtaagag aactacagaa atacatcaaa catgagcaag aggagctgca  1260
caggaaattt ttattgttta cagacacttt cctaaggaaa atacatgcac tatgtgaaga  1320
```

```
gcacttctca cctgcctcac ttgacctgaa atttgtaact cctaaagtaa tcaaactgct   1380
cgaaatctta cgcaaatata aaccatatga gcgacagcag tttgaaagcg ttgagtggta   1440
taataataga aatcaggata attatgtgtc atggagtgat tctgaggatg atgatgagga   1500
tgaagaaatt gaagaaaaag agaagccaga gacaaatttt ccttctcctt ttaccaacat   1560
tttgtgcgga attattttg tggaaagaag atacacagca gttgtcttaa acagattgat   1620
aaaggaagct ggcaaacaag atccagagct ggcttatatc agtagcaatt tcataactgg   1680
acatggcatt gggaagaatc agcctcgcaa caaacagatg gaagcagaat cagaaaaca    1740
ggaagaggta cttaggaaat tcgagcaca tgagaccaac ctgcttattg caacaagtat    1800
tgtagaagag ggtgttgata taccaaaatg caacttggtg gttcgttttg atttgcccac   1860
agaatatcga tcctatgttc aatctaaagg aagagcaagg gcacccatct ctaattatat   1920
aatgttagcg gatacagaca aaataaaaag ttttgaagaa gaccttaaaa cctacaaagc   1980
tattgaaaag atcttgagaa acaagtgttc caagtcggtt gatactggtg agactgacat   2040
tgatcctgtc atggatgatg atgacgtttt cccaccatat gtgttgaggc ctgacgatgg   2100
tggtccacga gtcacaatca acacggccat tggacacatc aatagatact gtgctagatt   2160
accaagtgat ccgtttactc atctagctcc taaatgcaga acccgagagt tgcctgatgg   2220
tacattttat tcaactcttt atctgccaat taactcacct cttcgagcct ccattgttgg   2280
tccaccaatg agctgtgtac gattggctga agagttgta gctctcattt gctgtgagaa    2340
actgcacaaa attggcgaac tggatgacca tttgatgcca gttgggaaag agactgttaa   2400
atatgaagag gagcttgatt tgcatgatga agaagagacc agtgttccag aagaccagg    2460
ttccacgaaa cgaaggcagt gctacccaaa agcaattcca gagtgtttga gggatagtta   2520
tcccagacct gatcagccct gttacctgta tgtgatagga atggttttaa ctacaccttt   2580
acctgatgaa ctcaacttta gaaggcggaa gctctatcct cctgaagata ccacaagatg   2640
ctttggaata ctgacggcca aacccatacc tcagattcca cactttcctg tgtacacacg   2700
ctctggagag gttaccatat ccattgagtt gaagaagtct ggtttcatgt tgtctctaca   2760
aatgcttgag ttgattacaa gacttcacca gtatatattc tcacatattc ttcggcttga   2820
aaaacctgca ctagaattta aacctacaga cgctgattca gcatactgtg ttctacctct   2880
taatgttgtt aatgactcca gcactttgga tattgacttt aaattcatgg aagatattga   2940
gaagtctgaa gctcgcatag gcattcccag tacaaagtat acaaaagaaa caccctttgt   3000
ttttaaatta gaagattacc aagatgccgt tatcattcca agatatcgca attttgatca   3060
gcctcatcga ttttatgtag ctgatgtgta cactgatctt accccactca gtaaatttcc   3120
ttcccctgag tatgaaactt ttgcagaata ttataaaaca aagtacaacc ttgacctaac   3180
caatctcaac cagccactgc tggatgtgga ccacacatct tcaagactta atcttttgac   3240
acctcgacat ttgaatcaga aggggaaagc gcttcctta agcagtgctg agaagaggaa    3300
agccaaatgg gaaagtctgc agaataaaca gatactggtt ccagaactct gtgctataca   3360
tccaattcca gcatcactgt ggagaaaagc tgtttgtctc cccagcatac tttatcgcct   3420
tcactgcctt ttgactgcag aggagctaag agcccagact gccagcgatg ctggcgtggg   3480
agtcagatca cttcctgcgg attttagata ccctaactta gacttcgggt ggaaaaaatc   3540
tattgacagc aaatctttca tctcaatttc taactcctct tcagctgaaa atgataatta   3600
ctgtaagcac agcacaattg tccctgaaaa tgctgcacat caaggtgcta atagaacctc   3660
```

-continued

```
ctctctagaa aatcatgacc aaatgtctgt gaactgcaga acgttgctca gcgagtcccc    3720
tggtaagctc cacgttgaag tttcagcaga tcttacagca attaatggtc tttcttacaa    3780
tcaaaatctc gccaatggca gttatgattt agctaacaga gacttttgcc aaggaaatca    3840
gctaaattac tacaagcagg aaatacccgt gcaaccaact acctcatatt ccattcagaa    3900
tttatacagt tacgagaacc agccccagcc cagcgatgaa tgtactctcc tgagtaataa    3960
ataccttgat ggaaatgcta acaaatctac ctcagatgga agtcctgtga tggccgtaat    4020
gcctggtacg acagacacta ttcaagtgct caagggcagg atggattctg agcagagccc    4080
ttctattggg tactcctcaa ggactcttgg ccccaatcct ggacttattc ttcaggcttt    4140
gactctgtca aacgctagtg atggatttaa cctggagcgg cttgaaatgc ttggcgactc    4200
ctttttaaag catgccatca ccacatatct attttgcact tacctgatg cgcatgaggg     4260
ccgcctttca tatgagaa gcaaaaggt cagcaactgt aatctgtatc gccttggaaa       4320
aaagaaggga ctacccagcc gcatggtggt gtcaatattt gatcccctg tgaattggct     4380
tcctcctggt tatgtagtaa atcaagacaa aagcaacaca gataaatggg aaaaagatga    4440
aatgacaaaa gactgcatgc tggcgaatgg caaactggat gaggattacg aggaggagga    4500
tgaggaggag gagagcctga tgtggagggc tccgaaggaa gaggctgact atgaagatga    4560
tttcctggag tatgatcagg aacatatcag atttatagat aatatgttaa tggggtcagg    4620
agcttttgta aagaaaatct ctctttctcc tttttcaacc actgattctg catatgaatg    4680
gaaaatgccc aaaaaatcct ccttaggtag tatgccattt tcatcagatt ttgaggattt    4740
tgactacagc tcttgggatg caatgtgcta tctggatcct agcaaagctg ttgaagaaga    4800
tgactttgtg gtggggttct ggaatccatc agaagaaaac tgtggtgttg acacgggaaa    4860
gcagtccatt tcttacgact gcacactga gcagtgtatt gctgacaaaa gcatagcgga    4920
ctgtgtggaa gccctgctgg gctgctattt aaccagctgt ggggagaggg ctgctcagct    4980
tttcctctgt tcactggggc tgaaggtgct cccggtaatt aaaaggactg atcgggaaaa    5040
ggccctgtgc cctactcggg agaatttcaa cagccaacaa agaacccttt cagtgagctg    5100
tgctgctgct tctgtggcca gttcacgctc ttctgtattg aaagactcgg aatatggttg    5160
tttgaagatt ccaccaagat gtatgtttga tcatccagat gcagataaaa cactgaatca    5220
ccttatatcg gggtttgaaa attttgaaaa gaaaatcaac tacagattca gaataaggc     5280
ttaccttctc caggctttta cacatgcctc ctaccactac aatactatca ctgattgtta    5340
ccagcgctta gaattcctgg gagatgcgat tttggactac ctcataacca agcaccttta    5400
tgaagacccg cggcagcact ccccggggt cctgacagac ctgcggtctg ccctggtcaa     5460
caacaccatc tttgcatcgc tggctgtaaa gtacgactac cacaagtact caaagctgt     5520
ctctcctgag ctcttccatg tcattgatga ctttgtgcag tttcagcttg agaagaatga    5580
aatgcaagga atggattctg agcttaggag atctgaggag gatgaagaga agaagaggga    5640
tattgaagtt ccaaaggcca tgggggatat ttttgagtcg cttgctggtg ccatttacat    5700
ggatagtggg atgtcactgg agacagtctg gcaggtgtac tatcccatga tgcggccact    5760
aatagaaaag ttttctgcaa atgtacccg ttccctgtg cgagaattgc ttgaaatgga     5820
accagaaact gccaaattta gcccggctga gagaacttac gacgggaagg tcagagtcac    5880
tgtggaagta gtaggaaagg ggaaatttaa aggtgttggt cgaagttaca ggattgccaa    5940
atctgcagca gcaagaagag ccctccgaag cctcaaagct aatcaacctc aggttcccaa    6000
tagctgaaac cgcttttaa aattcaaaac aagaaacaaa acaaaaaaaa ttaaggggaa      6060
```

-continued

```
aattatttaa atcggaaagg aagacttaaa gttgttagtg agtggaatga attgaaggca    6120
gaatttaaag tttggttgat aacaggatag ataacagaat aaaacattta acatatgtat    6180
aaaattttgg aactaattgt agttttagtt ttttgcgcaa acacaatctt atcttctttc    6240
ctcacttctg ctttgtttaa atcacaagag tgctttaatg atgacattta gcaagtgctc    6300
aaaataattg acaggttttg tttttttttt tttgagttta tgtcagcttt gcttagtgtt    6360
agaaggccat ggagcttaaa cctccagcag tccctaggat gatgtagatt cttctccatc    6420
tctccgtgtg tgcagtagtg ccagtcctgc agtagttgat aagctgaata gaaagataag    6480
gttttcgaga ggagaagtgc gccaatgttg tcttttcttt ccacgttata ctgtgtaagg    6540
tgatgttccc ggtcgctgtt gcacctgata gtaagggaca gattttttaat gaacattggc    6600 tggcatgttg gtgaatcaca ttttagtttt ctgatgccac atagtcttgc ataaaaaagg    6660
gttcttgcct taaaagtgaa accttcatgg atagtcttta atctctgatc ttttttggaac    6720 aaactgtttt acattccttt cattttatta tgcattagac gttgagacag cgtgatactt    6780
acaactcact agtatagttg taacttatta caggatcata ctaaaatttc tgtcatatgt    6840
atactgaaga catttttaaaa accagaatat gtagtctacg atattttttt atcataaaaa    6900
tgatctttgg ctaaacaccc catttttacta aagtcctcct gccaggtagt tcccactgat    6960
ggaaatgttt atggcaaata attttgcctt ctaggctgtt gctctaacaa aataaacctt    7020
agacatatca cacctaaaat atgctgcaga ttttataatt gattggttac ttatttaaga    7080
agcaaaacac agcacccttta cccttagtct cctcacataa atttcttact atacttttca    7140
taatgttgca tgcatatttc acctaccaaa gctgtgctgt taatgccgtg aaagtttaac    7200
gtttgcgata aactgccgta attttgatac atctgtgatt taggtcatta atttagataa    7260
actagctcat tatttccatc tttggaaaag gaaaaaaaaa aaaacttctt taggcatttg    7320
cctaagtttc tttaattaga cttgtaggca ctcttcactt aaatacctca gttcttcttt    7380
tcttttgcat gcattttttcc cctgtttggt gctatgttta tgtattatgc ttgaaatttt    7440
aatttttttt tttttgcact gtaactataa tacctcttaa tttacctttt taaaagctgt    7500
gggtcagtct tgcactccca tcaacatacc agtagaggtt tgctgcaatt tgccccgtta    7560
attatgcttg aagtttaaga aagctgagca gaggtgtctc atatttccca gcacatgatt    7620
ctgaacttga tgcttcgtgg aatgctgcat ttatatgtaa gtgacatttg aatactgtcc    7680
ttcctgcttt atctgcatca tccacccaca gagaaatgcc tctgtgcgag tgcaccgaca    7740
gaaaactgtc agctctgctt tctaaggaac cctgagtgag gggggtatta agcttctcca    7800
gtgttttttg ttgtctccaa tcttaaactt aaattgagat ctaaattatt aaacgagttt    7860
ttgagcaaat taggtgactt gttttaaaaa tatttaattc cgatttggaa ccttagatgt    7920
ctatttgatt ttttaaaaaa ccttaatgta agatatgacc agttaaaaca aagcaattct    7980
tgaattatat aactgtaaaa gtgtgcagtt aacaaggctg gatgtgaatt ttattctgag    8040
ggtgatttgt gatcaagttt aatcacaaat ctcttaatat ttataaacta cctgatgcca    8100
ggagcttagg gctttgcatt gtgtctaata cattgatccc agtgttacgg gattctcttg    8160
attcctggca ccaaaatcag attgttttca cagtyatgat tcccagtggg agaaaaatgc    8220
ctcaatatat ttgtaacctt aagaagagta ttttttttgtt aatactaaga tgttcaaact    8280
tagacatgat taggtcatac attctcaggg gttcaaattt ccttctacca ttcaaatgtt    8340
ttatcaacag caaacttcag ccgtttcact ttttgttgga gaaaaatagt agattttaat    8400
```

```
ttgactcaca gtttgaagca ttctgtgatc ccctggttac tgagttaaaa aataaaaaag      8460
tacgagttag acatatgaaa tggttatgaa cgcttttgtg ctgctgattt ttaatgctgt      8520
aaagttttcc tgtgtttagc ttgttgaaat gttttgcatc tgtcaattaa ggaaaaaaaa      8580
aatcactcta tgttgcccca ctttagagcc ctgtgtgcca ccctgtgttc ctgtgattgc      8640
aatgtgagac cgaatgtaat atggaaaacc taccagtggg gtgtggttgt gccctgagca      8700
cgtgtgtaaa ggactgggga ggcgtgtctt gaaaaagcaa ctgcagaaat tccttatgat      8760
gattgtgtgc aagttagtta acatgaacct tcatttgtaa attttttaaa atttctttta      8820
taatatgctt tccgcagtcc taactatgct gcgttttata atagctttt cccttctgtt      8880
ctgttcatgt agcacagata agcattgcac ttggtaccat gctttacctc atttcaagaa      8940
aatatgctta acagagagga aaaaaatgtg gtttggcctt gctgctgttt tgatttatgg      9000
aatttgaaaa agataattat aatgcctgca atgtgtcata tactcgcaca acttaaatag      9060
gtcattttg tctgtggcat ttttactgtt tgtgaaagta tgaaacagat ttgttaactg       9120
aactcttaat tatgttttta aaatgtttgt tatatttctt ttctttttc ttttatatta      9180
cgtgaagtga tgaaatttag aatgacctct aacactcctg taattgtctt ttaaaaatact     9240
gatatttta tttgttaata atactttgcc ctcagaaaga ttctgatacc ctgccttgac       9300
aacatgaaac ttgaggctgc tttggttcat gaatccaggt gttcccccgg cagtcggctt      9360
cttcagtcgc tccctggagg caggtgggca ctgcagagga tcactggaat ccagatcgag      9420
cgcagttcat gcacaaggcc ccgttgattt aaaatattgg atcttgctct gttagggtgt      9480
ctaatccctt tacacaagat tgaagccacc aaactgagac cttgatacct tttttttaact    9540
gcatctgaaa ttatgttaag agtctttaac ccatttgcat tatctgcaga agagaaactc     9600
atgtcatgtt tattacctat atggttgttt taattacatt tgaataatta tattttttcca    9660
accactgatt acttttcagg aatttaatta tttccagata aatttcttta ttttatattg     9720
tacatgaaaa gttttaaaga tatgtttaag accaagacta ttaaaatgat ttttaaagtt     9780
gttggagacg ccaatagcaa tatctaggaa atttgcattg agaccattgt attttccact    9840
agcagtgaaa atgattttc acaactaact tgtaaatata ttttaatcat tacttctttt     9900
tttctagtcc attttttatt ggacatcaac cacagacaat ttaaatttta tagatgcact    9960
aagaattcac tgcagcagca ggttacatag caaaaaatgca aaggtgaaca ggaagtaaat    10020
ttctggcttt tctgctgtaa atagtgaagg aaaattacta aaatcaagta aaactaatgc    10080
atattatttg attgacaata aaatatttac catcacatgc tgcagctgtt ttttaaggaa     10140
catgatgtca ttcattcata cagtaatcat gctgcagaaa tttgcagtct gcaccttatg    10200
gatcacaatt acctttagtt gttttttttg taataattgt agccaagtaa atctccaata    10260
aagttatcgt ctgttcaaaa aaaaaaaaaa aaaaaaaaaa aaaaaaaaaa aaaaaaaaaa    10320
aaa                                                                    10323

<210> SEQ ID NO 8
<211> LENGTH: 10220
<212> TYPE: DNA
<213> ORGANISM: Homo sapiens

<400> SEQUENCE: 8
ggaaactctg aaagaactta gaatcagcat tttgagagca gaagcttggg catgctgtga        60
ttttccaata aactgctatc acaatgtcaa aatgcagttc agacaagagc aacacagaga      120
tctcaaacat taaaacgtaa gctgtgctag aacaaaaatg caatgaaaga aacactggat       180
```

```
gaatgaaaag ccctgctttg caacccctca gcatggcagg cctgcagctc atgaccctg      240 cttcctcacc aatgggtcct ttctttggac tgccatggca acaagaagca attcatgata      300
acatttatac gccaagaaaa tatcaggttg aactgcttga agcagctctg gatcataata      360
ccatcgtctg tttaaacact ggctcaggga agacatttat tgcagtacta ctcactaaag      420
agctgtccta tcagatcagg ggagacttca gcagaaatgg aaaaaggacg tgttcttgg       480 tcaactctgc aaaccaggtt gctcaacaag tgtcagctgt cagaactcat tcagatctca      540
aggttgggga atactcaaac ctagaagtaa atgcatcttg acaaaagag agatggaacc       600 aagagtttac taagcaccag gttctcatta tgacttgcta tgtcgccttg aatgttttga      660
aaaatggtta cttatcactg tcagacatta acctttggt gtttgatgag tgtcatcttg       720
caatcctaga ccaccctat cgagaaatta tgaagctctg tgaaaattgt ccatcatgtc       780
ctcgcatttt gggactaact gcttccattt taaatgggaa atgtgatcca gaggaattgg      840
aagaaaagat tcagaaacta gagaaaattc ttaagagtaa tgctgaaact gcaactgacc      900
tggtggtctt agacaggtat acttctcagc catgtgagat tgtggtggat tgtggaccat      960
ttactgacag aagtgggctt tatgaaagac tgctgatgga attagaagaa gcacttaatt      1020
ttatcaatga ttgtaatata tctgtacatt caaaagaaag agattctact ttaatttcga      1080
aacagatact atcagactgt cgtgccgtat tggtagttct gggaccctgg tgtgcagata      1140
aagtagctgg aatgatggta agagaactac agaaatacat caaacatgag caagaggagc      1200
tgcacaggaa attttttattg tttacagaca ctttcctaag gaaaatacat gcactatgtg      1260
aagagcactt ctcacctgcc tcacttgacc tgaaatttgt aactcctaaa gtaatcaaac      1320
tgctcgaaat cttacgcaaa tataaaccat atgagcgaca gcagtttgaa agcgttgagt      1380
ggtataataa tagaaatcag gataattatg tgtcatggag tgattctgag gatgatgatg      1440
aggatgaaga aattgaagaa aagagaagc cagagacaaa ttttccttct ccttttacca      1500 acatttgtg cggaattatt tttgtggaaa gaagatacac agcagttgtc ttaaacagat      1560
tgataaagga agctggcaaa caagatccag agctggctta tatcagtagc aatttcataa      1620
ctggacatgg cattgggaag aatcagcctc gcaacaaaca gatggaagca gaattcagaa      1680
aacaggaaga ggtacttagg aaatttcgag cacatgagac caacctgctt attgcaacaa      1740
gtattgtaga agagggtgtt gatataccaa atgcaacttg gtggttcgt tttgatttgc       1800 ccacagaata tcgatcctat gttcaatcta aaggaagagc aagggcaccc atctctaatt      1860
atataatgtt agcggataca gacaaaataa aaagttttga agaagacctt aaaacctaca      1920
aagctattga aaagatcttg agaaacaagt gttccaagtc ggttgatact ggtgagactg      1980
acattgatcc tgtcatggat gatgatgacg ttttcccacc atatgtgttg aggcctgacg      2040
atggtggtcc acgagtcaca atcaacacgg ccattggaca catcaataga tactgtgcta      2100
gattaccaag tgatccgttt actcatctag ctcctaaatg cagaacccga gagttgcctg      2160
atggtacatt ttattcaact ctttatctgc caattaactc acctcttcga gcctccattg      2220
ttggtccacc aatgagctgt gtacgattgg ctgaaagagt tgtagctctc atttgctgtg      2280
agaaactgca caaattggc gaactggatg accatttgat gccagttggg aaagagactg       2340
ttaaatatga agaggagctt gatttgcatg atgaagaaga gaccagtgtt ccaggaagac      2400
caggttccac gaaacgaagg cagtgctacc caaaagcaat tccagagtgt ttgagggata      2460
gttatcccag acctgatcag ccctgttacc tgtatgtgat aggaatggtt ttaactacac      2520
```

```
ctttacctga tgaactcaac tttagaaggc ggaagctcta tcctcctgaa gataccacaa    2580
gatgctttgg aatactgacg gccaaaccca tacctcagat tccacacttt cctgtgtaca    2640
cacgctctgg agaggttacc atatccattg agttgaagaa gtctggtttc atgttgtctc    2700
tacaaatgct tgagttgatt acaagacttc accagtatat attctcacat attcttcggc    2760
ttgaaaaacc tgcactagaa tttaaaccta cagacgctga ttcagcatac tgtgttctac    2820
ctcttaatgt tgttaatgac tccagcactt tggatattga cttttaaattc atggaagata    2880 ttgagaagtc tgaagctcgc ataggcattc ccagtacaaa gtatacaaaa gaaacaccct    2940 ttgttttttaa attagaagat taccaagatg ccgttatcat tccaagatat cgcaattttg    3000
atcagcctca tcgattttat gtagctgatg tgtacactga tcttaccccca ctcagtaaat    3060 ttccttcccc tgagtatgaa acttttgcag aatattataa aacaaagtac aaccttgacc    3120
taaccaatct caaccagcca ctgctggatg tggaccacac atcttcaaga cttaatctttt    3180 tgacacctcg acatttgaat cagaagggga agcgcttcc tttaagcagt gctgagaaga    3240
ggaaagccaa atgggaaagt ctgcagaata acagatact ggttccagaa ctctgtgcta    3300
tacatccaat tccagcatca ctgtggagaa aagctgtttg tctccccagc atactttatc    3360
gccttcactg cctttttgact gcagaggagc taagagccca gactgccagc gatgctggcg    3420
tgggagtcag atcacttcct gcggatttta gatacccctaa cttagacttc gggtggaaaa    3480
aatctattga cagcaaatct ttcatctcaa tttctaactc ctcttcagct gaaaatgata    3540
attactgtaa gcacagcaca attgtccctg aaaatgctgc acatcaaggt gctaatagaa    3600
cctcctctct agaaaatcat gaccaaatgt ctgtgaactg cagaacgttg ctcagcgagt    3660
cccctggtaa gctccacgtt gaagtttcag cagatcttac agcaattaat ggtctttctt    3720
acaatcaaaa tctcgccaat ggcagttatg atttagctaa cagagacttt tgccaaggaa    3780
atcagctaaa ttactacaag caggaaatac ccgtgcaacc aactacctca tattccattc    3840
agaatttata cagttacgag aaccagcccc agcccagcga tgaatgtact ctcctgagta    3900
ataaatacct tgatggaaat gctaacaaat ctacctcaga tggaagtcct gtgatggccg    3960
taatgcctgg tacgacagac actattcaag tgctcaaggg caggatggat tctgagcaga    4020
gcccttctat tgggtactcc tcaaggactc ttggcccccaa tcctggactt attcttcagg    4080
ctttgactct gtcaaacgct agtgatggat ttaacctgga gcggcttgaa atgcttggcg    4140 actcctttt aaaagcatgcc atcaccacat atctattttg cacttaccct gatgcgcatg    4200
agggccgcct ttcatatatg agaagcaaaa aggtcagcaa ctgtaatctg tatcgccttg    4260 gaaaaagaa gggactaccc agccgcatgg tggtgtcaat atttgatccc cctgtgaatt    4320
ggcttcctcc tggttatgta gtaaatcaag acaaaagcaa cacagataaa tgggaaaaag    4380
atgaaatgac aaaagactgc atgctggcga atggcaaact ggatgaggat tacgaggagg    4440
aggatgagga ggaggagagc ctgatgtgga gggctccgaa ggaagaggct gactatgaag    4500
atgatttcct ggagtatgat caggaacata tcagatttat agataatatg ttaatggggt    4560
caggagcttt tgtaaagaaa atctctcttt ctccttttc aaccactgat tctgcatatg    4620
aatggaaaat gccaaaaaaa tcctccttag gtagtatgcc atttttcatca gattttgagg    4680 attttgacta cagctcttgg gatgcaatgt gctatctgga tccctagcaaa gctgttgaag    4740 aagatgactt tgtggtgggg ttctggaatc catcagaaga aaactgtggt gttgacacgg    4800
gaaagcagtc catttcttac gacttgcaca ctgagcagtg tattgctgac aaaagcatag    4860
cggactgtgt ggaagccctg ctgggctgct atttaaccag ctgtgggggag agggctgctc    4920
```

```
agcttttcct ctgttcactg gggctgaagg tgctcccggt aattaaaagg actgatcggg    4980
aaaaggccct gtgccctact cgggagaatt tcaacagcca acaaaagaac ctttcagtga    5040
gctgtgctgc tgcttctgtg gccagttcac gctcttctgt attgaaagac tcggaatatg    5100
gttgtttgaa gattccacca agatgtatgt ttgatcatcc agatgcagat aaaacactga    5160
atcaccttat atcggggttt gaaaattttg aaagaaaat caactacaga ttcaagaata     5220
aggcttacct tctccaggct tttacacatg cctcctacca ctacaatact atcactgatt    5280
gttaccagcg cttagaattc ctgggagatg cgattttgga ctacctcata accaagcacc    5340
tttatgaaga cccgcggcag cactcccgg gggtcctgac agacctgcgg tctgccctgg      5400
tcaacaacac catctttgca tcgctggctg taaagtacga ctaccacaag tacttcaaag    5460
ctgtctctcc tgagctcttc catgtcattg atgactttgt gcagtttcag cttgagaaga    5520
atgaaatgca aggaatggat tctgagctta ggagatctga ggaggatgaa gagaaagaag    5580
aggatattga agttccaaag gccatggggg atattttga gtcgcttgct ggtgccattt      5640
acatggatag tgggatgtca ctggagacag tctggcaggt gtactatccc atgatgcggc    5700
cactaataga aaagttttct gcaaatgtac cccgttcccc tgtgcgagaa ttgcttgaaa    5760
tggaaccaga aactgccaaa tttagcccgg ctgagagaac ttacgacggg aaggtcagag    5820
tcactgtgga agtagtagga aaggggaaat ttaaaggtgt tggtcgaagt tacaggattg    5880
ccaaatctgc agcagcaaga agagccctcc gaagcctcaa agctaatcaa cctcaggttc    5940
ccaatagctg aaaccgcttt ttaaaattca aacaagaaa caaaacaaaa aaaattaagg      6000
ggaaaattat ttaaatcgga aaggaagact taaagttgtt agtgagtgga atgaattgaa    6060
ggcagaattt aaagtttggt tgataacagg atagataaca gaataaaaca tttaacatat    6120
gtataaaatt ttggaactaa ttgtagtttt agtttttgc gcaaacacaa tcttatcttc      6180
tttcctcact tctgctttgt ttaaatcaca agagtgcttt aatgatgaca tttagcaagt    6240
gctcaaaata attgacaggt tttgtttttt tttttttgag tttatgtcag cttggcttag     6300
tgttagaagg ccatggagct taaacctcca gcagtcccta ggatgatgta gattcttctc    6360
catctctccg tgtgtgcagt agtgccagtc ctgcagtagt tgataagctg aatagaaaga    6420
taaggttttc gagaggagaa gtgcgccaat gttgtctttt cttttccacgt tatactgtgt    6480 aaggtgatgt tcccggtcgc tgttgcacct gatagtaagg gacagatttt taatgaacat    6540
tggctggcat gttggtgaat cacattttag ttttctgatg ccacatagtc ttgcataaaa    6600
aagggttctt gccttaaaag tgaaaccttc atggatagtc tttaatctct gatctttttg    6660
gaacaaactg ttttacattc ctttcatttt attatgcatt agacgttgag acagcgtgat    6720
acttacaact cactagtata gttgtaactt attacaggat catactaaaa tttctgtcat    6780
atgtatactg aagacatttt aaaaaccaga atatgtagtc tacggatatt ttttatcata    6840
aaaatgatct ttggctaaac accccatttt actaaagtcc tcctgccagg tagttcccac    6900
tgatggaaat gtttatggca aataattttg ccttctaggc tgttgctcta acaaaataaa    6960
ccttagacat atcacaccta aaatatgctg cagattttat aattgattgg ttacttattt     7020
aagaagcaaa acacagcacc tttaccctta gtctcctcac ataaatttct tactatactt    7080
ttcataatgt tgcatgcata tttcacctac caaagctgtg ctgttaatgc cgtgaaagtt    7140
taacgtttgc gataaactgc cgtaattttg atacatctgt gatttaggtc attaatttag    7200
ataaactagc tcattatttc catctttgga aaaggaaaaa aaaaaaaact tctttaggca    7260
```

```
tttgcctaag tttctttaat tagacttgta ggcactcttc acttaaatac ctcagttctt    7320
cttttctttt gcatgcattt ttcccctgtt tggtgctatg tttatgtatt atgcttgaaa    7380
ttttaatttt tttttttttg cactgtaact ataatacctc ttaatttacc tttttaaaag    7440
ctgtgggtca gtcttgcact cccatcaaca taccagtaga ggtttgctgc aatttgcccc    7500
gttaattatg cttgaagttt aagaaagctg agcagaggtg tctcatattt cccagcacat    7560
gattctgaac ttgatgcttc gtggaatgct gcatttatat gtaagtgaca tttgaatact    7620
gtccttcctg ctttatctgc atcatccacc cacagagaaa tgcctctgtg cgagtgcacc    7680
gacagaaaac tgtcagctct gctttctaag gaaccctgag tgaggggggt attaagcttc    7740
tccagtgttt tttgttgtct ccaatcttaa acttaaattg agatctaaat tattaaacga    7800 gttttttgagc aaattaggtg acttgtttta aaaatattta attccgattt ggaaccttag    7860
atgtctattt gatttttttaa aaaaccttaa tgtaagatat gaccagttaa aacaaagcaa    7920
ttcttgaatt atataactgt aaaagtgtgc agttaacaag gctggatgtg aattttattc    7980
tgagggtgat ttgtgatcaa gtttaatcac aaatctctta atatttataa actacctgat    8040
gccaggagct tagggctttg cattgtgtct aatacattga tcccagtgtt acgggattct    8100
cttgattcct ggcaccaaaa tcagattgtt ttcacagtta tgattcccag tgggagaaaa    8160
atgcctcaat atatttgtaa ccttaagaag agtatttttt tgttaatact aagatgttca    8220
aacttagaca tgattaggtc atacattctc aggggttcaa atttccttct accattcaaa    8280
tgttttatca acagcaaact tcagccgttt cactttttgt tggagaaaaa tagtagattt    8340
taatttgact cacagtttga agcattctgt gatcccctgg ttactgagtt aaaaaataaa    8400
aaagtacgag ttagacatat gaaatggtta tgaacgcttt tgtgctgctg attttttaatg    8460 ctgtaaagtt ttcctgtgtt tagcttgttg aaatgttttg catctgtcaa ttaaggaaaa    8520
aaaaaatcac tctatgttgc cccactttag agccctgtgt gccaccctgt gttcctgtga    8580
ttgcaatgtg agaccgaatg taatatggaa aacctaccag tggggtgtgg ttgtgccctg    8640
agcacgtgtg taaaggactg gggaggcgtg tcttgaaaaa gcaactgcag aaattcctta    8700
tgatgattgt gtgcaagtta gttaacatga accttcattt gtaaattttt taaaattttct    8760 tttataatat gctttccgca gtcctaacta tgctgcgttt tataatagct ttttcccttc    8820
tgttctgttc atgtagcaca gataagcatt gcacttggta ccatgcttta cctcatttca    8880
agaaaatatg cttaacagag aggaaaaaaa tgtggtttgg ccttgctgct gttttgattt    8940
atggaatttg aaaagataa ttataatgcc tgcaatgtgt catatactcg cacaacttaa    9000
ataggtcatt tttgtctgtg gcattttttac tgtttgtgaa agtatgaaac agatttgtta    9060
actgaactct taattatgtt tttaaaatgt ttgttatatt tcttttctttt tttcttttat    9120 attacgtgaa gtgatgaaat ttagaatgac ctctaacact cctgtaattg tcttttaaaa    9180
tactgatatt tttatttgtt aataatactt tgccctcaga aagattctga taccctgcct    9240
tgacaacatg aaacttgagg ctgctttggt tcatgaatcc aggtgttccc ccggcagtcg    9300
gcttcttcag tcgctccctg gaggcaggtg ggcactgcag aggatcactg gaatccagat    9360
cgagcgcagt tcatgcacaa ggccccgttg atttaaaata ttggatcttg ctctgttagg    9420
gtgtctaatc cctttacaca agattgaagc caccaaactg agaccttgat acctttttt    9480 aactgcatct gaaattatgt taagagtctt taacccattt gcattatctg cagaagagaa    9540
actcatgtca tgtttattac ctatatggtt gtttaattaa catttgaata attatatttt    9600
tccaaccact gattactttt caggaattta attatttcca gataaatttc tttatttat    9660
```

-continued

```
attgtacatg aaaagtttta aagatatgtt taagaccaag actattaaaa tgatttttaa    9720
agttgttgga gacgccaata gcaatatcta ggaaatttgc attgagacca ttgtattttc    9780
cactagcagt gaaatgatt tttcacaact aacttgtaaa tatattttaa tcattacttc    9840
tttttttcta gtccattttt atttggacat caaccacaga caatttaaat tttatagatg    9900
cactaagaat tcactgcagc agcaggttac atagcaaaaa tgcaaggtg aacaggaagt    9960 aaatttctgg cttttctgct gtaaatagtg aaggaaaatt actaaaatca agtaaaacta    10020
atgcatatta tttgattgac aataaaatat ttaccatcac atgctgcagc tgttttttaa    10080
ggaacatgat gtcattcatt catacagtaa tcatgctgca gaaatttgca gtctgcacct    10140
tatggatcac aattaccttt agttgttttt tttgtaataa ttgtagccaa gtaaatctcc    10200
aataaagtta tcgtctgttc                                                10220
```

<210> SEQ ID NO 9
<211> LENGTH: 1922
<212> TYPE: PRT
<213> ORGANISM: Homo sapiens

<400> SEQUENCE: 9

```
Met Lys Ser Pro Ala Leu Gln Pro Leu Ser Met Ala Gly Leu Gln Leu
1               5                   10                  15

Met Thr Pro Ala Ser Ser Pro Met Gly Pro Phe Phe Gly Leu Pro Trp
            20                  25                  30

Gln Gln Glu Ala Ile His Asp Asn Ile Tyr Thr Pro Arg Lys Tyr Gln
        35                  40                  45

Val Glu Leu Leu Glu Ala Ala Leu Asp His Asn Thr Ile Val Cys Leu
    50                  55                  60

Asn Thr Gly Ser Gly Lys Thr Phe Ile Ala Val Leu Leu Thr Lys Glu
65                  70                  75                  80

Leu Ser Tyr Gln Ile Arg Gly Asp Phe Ser Arg Asn Gly Lys Arg Thr
                85                  90                  95

Val Phe Leu Val Asn Ser Ala Asn Gln Val Ala Gln Gln Val Ser Ala
            100                 105                 110

Val Arg Thr His Ser Asp Leu Lys Val Gly Glu Tyr Ser Asn Leu Glu
        115                 120                 125

Val Asn Ala Ser Trp Thr Lys Glu Arg Trp Asn Gln Glu Phe Thr Lys
    130                 135                 140

His Gln Val Leu Ile Met Thr Cys Tyr Val Ala Leu Asn Val Leu Lys
145                 150                 155                 160

Asn Gly Tyr Leu Ser Leu Ser Asp Ile Asn Leu Leu Val Phe Asp Glu
                165                 170                 175

Cys His Leu Ala Ile Leu Asp His Pro Tyr Arg Glu Ile Met Lys Leu
            180                 185                 190

Cys Glu Asn Cys Pro Ser Cys Pro Arg Ile Leu Gly Leu Thr Ala Ser
        195                 200                 205

Ile Leu Asn Gly Lys Cys Asp Pro Glu Glu Leu Glu Glu Lys Ile Gln
    210                 215                 220

Lys Leu Glu Lys Ile Leu Lys Ser Asn Ala Glu Thr Ala Thr Asp Leu
225                 230                 235                 240

Val Val Leu Asp Arg Tyr Thr Ser Gln Pro Cys Glu Ile Val Val Asp
                245                 250                 255

Cys Gly Pro Phe Thr Asp Arg Ser Gly Leu Tyr Glu Arg Leu Leu Met
            260                 265                 270
```

```
Glu Leu Glu Ala Leu Asn Phe Ile Asn Asp Cys Asn Ile Ser Val
        275                 280                 285

His Ser Lys Glu Arg Asp Ser Thr Leu Ile Ser Lys Gln Ile Leu Ser
    290                 295                 300

Asp Cys Arg Ala Val Leu Val Val Leu Gly Pro Trp Cys Ala Asp Lys
305                 310                 315                 320

Val Ala Gly Met Met Val Arg Glu Leu Gln Lys Tyr Ile Lys His Glu
                325                 330                 335

Gln Glu Glu Leu His Arg Lys Phe Leu Leu Phe Thr Asp Thr Phe Leu
            340                 345                 350

Arg Lys Ile His Ala Leu Cys Glu Glu His Phe Ser Pro Ala Ser Leu
        355                 360                 365

Asp Leu Lys Phe Val Thr Pro Lys Val Ile Lys Leu Leu Glu Ile Leu
    370                 375                 380

Arg Lys Tyr Lys Pro Tyr Glu Arg Gln Gln Phe Glu Ser Val Glu Trp
385                 390                 395                 400

Tyr Asn Asn Arg Asn Gln Asp Asn Tyr Val Ser Trp Ser Asp Ser Glu
                405                 410                 415

Asp Asp Asp Glu Asp Glu Glu Ile Glu Glu Lys Glu Lys Pro Glu Thr
            420                 425                 430

Asn Phe Pro Ser Pro Phe Thr Asn Ile Leu Cys Gly Ile Ile Phe Val
        435                 440                 445

Glu Arg Arg Tyr Thr Ala Val Val Leu Asn Arg Leu Ile Lys Glu Ala
    450                 455                 460

Gly Lys Gln Asp Pro Glu Leu Ala Tyr Ile Ser Ser Asn Phe Ile Thr
465                 470                 475                 480

Gly His Gly Ile Gly Lys Asn Gln Pro Arg Asn Lys Gln Met Glu Ala
                485                 490                 495

Glu Phe Arg Lys Gln Glu Glu Val Leu Arg Lys Phe Arg Ala His Glu
            500                 505                 510

Thr Asn Leu Leu Ile Ala Thr Ser Ile Val Glu Glu Gly Val Asp Ile
        515                 520                 525

Pro Lys Cys Asn Leu Val Val Arg Phe Asp Leu Pro Thr Glu Tyr Arg
    530                 535                 540

Ser Tyr Val Gln Ser Lys Gly Arg Ala Arg Ala Pro Ile Ser Asn Tyr
545                 550                 555                 560

Ile Met Leu Ala Asp Thr Asp Lys Ile Lys Ser Phe Glu Glu Asp Leu
                565                 570                 575

Lys Thr Tyr Lys Ala Ile Glu Lys Ile Leu Arg Asn Lys Cys Ser Lys
            580                 585                 590

Ser Val Asp Thr Gly Glu Thr Asp Ile Asp Pro Val Met Asp Asp Asp
        595                 600                 605

Asp Val Phe Pro Pro Tyr Val Leu Arg Pro Asp Asp Gly Gly Pro Arg
    610                 615                 620

Val Thr Ile Asn Thr Ala Ile Gly His Ile Asn Arg Tyr Cys Ala Arg
625                 630                 635                 640

Leu Pro Ser Asp Pro Phe Thr His Leu Ala Pro Lys Cys Arg Thr Arg
                645                 650                 655

Glu Leu Pro Asp Gly Thr Phe Tyr Ser Thr Leu Tyr Leu Pro Ile Asn
            660                 665                 670

Ser Pro Leu Arg Ala Ser Ile Val Gly Pro Pro Met Ser Cys Val Arg
        675                 680                 685
```

-continued

Leu Ala Glu Arg Val Ala Leu Ile Cys Cys Glu Lys Leu His Lys
690                 695                 700

Ile Gly Glu Leu Asp Asp His Leu Met Pro Val Gly Lys Glu Thr Val
705                 710                 715                 720

Lys Tyr Glu Glu Glu Leu Asp Leu His Asp Glu Glu Thr Ser Val
                    725                 730                 735

Pro Gly Arg Pro Gly Ser Thr Lys Arg Arg Gln Cys Tyr Pro Lys Ala
                740                 745                 750

Ile Pro Glu Cys Leu Arg Asp Ser Tyr Pro Arg Pro Asp Gln Pro Cys
            755                 760                 765

Tyr Leu Tyr Val Ile Gly Met Val Leu Thr Thr Pro Leu Pro Asp Glu
770                 775                 780

Leu Asn Phe Arg Arg Lys Leu Tyr Pro Pro Glu Asp Thr Thr Arg
785                 790                 795                 800

Cys Phe Gly Ile Leu Thr Ala Lys Pro Ile Pro Gln Ile Pro His Phe
                    805                 810                 815

Pro Val Tyr Thr Arg Ser Gly Glu Val Thr Ile Ser Ile Glu Leu Lys
                820                 825                 830

Lys Ser Gly Phe Met Leu Ser Leu Gln Met Leu Glu Leu Ile Thr Arg
    835                 840                 845

Leu His Gln Tyr Ile Phe Ser His Ile Leu Arg Leu Glu Lys Pro Ala
850                 855                 860

Leu Glu Phe Lys Pro Thr Asp Ala Asp Ser Ala Tyr Cys Val Leu Pro
865                 870                 875                 880

Leu Asn Val Val Asn Asp Ser Ser Thr Leu Asp Ile Asp Phe Lys Phe
                885                 890                 895

Met Glu Asp Ile Glu Lys Ser Glu Ala Arg Ile Gly Ile Pro Ser Thr
                900                 905                 910

Lys Tyr Thr Lys Glu Thr Pro Phe Val Phe Lys Leu Glu Asp Tyr Gln
    915                 920                 925

Asp Ala Val Ile Ile Pro Arg Tyr Arg Asn Phe Asp Gln Pro His Arg
930                 935                 940

Phe Tyr Val Ala Asp Val Tyr Thr Asp Leu Thr Pro Leu Ser Lys Phe
945                 950                 955                 960

Pro Ser Pro Glu Tyr Glu Thr Phe Ala Glu Tyr Tyr Lys Thr Lys Tyr
                965                 970                 975

Asn Leu Asp Leu Thr Asn Leu Asn Gln Pro Leu Leu Asp Val Asp His
            980                 985                 990

Thr Ser Ser Arg Leu Asn Leu Leu Thr Pro Arg His Leu Asn Gln Lys
        995                 1000                1005

Gly Lys Ala Leu Pro Leu Ser Ser Ala Glu Lys Arg Lys Ala Lys
    1010                1015                1020

Trp Glu Ser Leu Gln Asn Lys Gln Ile Leu Val Pro Glu Leu Cys
    1025                1030                1035

Ala Ile His Pro Ile Pro Ala Ser Leu Trp Arg Lys Ala Val Cys
    1040                1045                1050

Leu Pro Ser Ile Leu Tyr Arg Leu His Cys Leu Leu Thr Ala Glu
    1055                1060                1065

Glu Leu Arg Ala Gln Thr Ala Ser Asp Ala Gly Val Gly Val Arg
    1070                1075                1080

Ser Leu Pro Ala Asp Phe Arg Tyr Pro Asn Leu Asp Phe Gly Trp
    1085                1090                1095

Lys Lys Ser Ile Asp Ser Lys Ser Phe Ile Ser Ile Ser Asn Ser

|      |      |      | 1100 |      |      |      | 1105 |      |      |      | 1110 |      |      |      |
|------|------|------|------|------|------|------|------|------|------|------|------|------|------|------|

Ser Ser Ala Glu Asn Asp Asn Tyr Cys Lys His Ser Thr Ile Val
　　1115　　　　　　　　1120　　　　　　　　1125

Pro Glu Asn Ala Ala His Gln Gly Ala Asn Arg Thr Ser Ser Leu
　　1130　　　　　　　　1135　　　　　　　　1140

Glu Asn His Asp Gln Met Ser Val Asn Cys Arg Thr Leu Leu Ser
　　1145　　　　　　　　1150　　　　　　　　1155

Glu Ser Pro Gly Lys Leu His Val Glu Val Ser Ala Asp Leu Thr
　　1160　　　　　　　　1165　　　　　　　　1170

Ala Ile Asn Gly Leu Ser Tyr Asn Gln Asn Leu Ala Asn Gly Ser
　　1175　　　　　　　　1180　　　　　　　　1185

Tyr Asp Leu Ala Asn Arg Asp Phe Cys Gln Gly Asn Gln Leu Asn
　　1190　　　　　　　　1195　　　　　　　　1200

Tyr Tyr Lys Gln Glu Ile Pro Val Gln Pro Thr Thr Ser Tyr Ser
　　1205　　　　　　　　1210　　　　　　　　1215

Ile Gln Asn Leu Tyr Ser Tyr Glu Asn Gln Pro Gln Pro Ser Asp
　　1220　　　　　　　　1225　　　　　　　　1230

Glu Cys Thr Leu Leu Ser Asn Lys Tyr Leu Asp Gly Asn Ala Asn
　　1235　　　　　　　　1240　　　　　　　　1245

Lys Ser Thr Ser Asp Gly Ser Pro Val Met Ala Val Met Pro Gly
　　1250　　　　　　　　1255　　　　　　　　1260

Thr Thr Asp Thr Ile Gln Val Leu Lys Gly Arg Met Asp Ser Glu
　　1265　　　　　　　　1270　　　　　　　　1275

Gln Ser Pro Ser Ile Gly Tyr Ser Ser Arg Thr Leu Gly Pro Asn
　　1280　　　　　　　　1285　　　　　　　　1290

Pro Gly Leu Ile Leu Gln Ala Leu Thr Leu Ser Asn Ala Ser Asp
　　1295　　　　　　　　1300　　　　　　　　1305

Gly Phe Asn Leu Glu Arg Leu Glu Met Leu Gly Asp Ser Phe Leu
　　1310　　　　　　　　1315　　　　　　　　1320

Lys His Ala Ile Thr Thr Tyr Leu Phe Cys Thr Tyr Pro Asp Ala
　　1325　　　　　　　　1330　　　　　　　　1335

His Glu Gly Arg Leu Ser Tyr Met Arg Ser Lys Lys Val Ser Asn
　　1340　　　　　　　　1345　　　　　　　　1350

Cys Asn Leu Tyr Arg Leu Gly Lys Lys Lys Gly Leu Pro Ser Arg
　　1355　　　　　　　　1360　　　　　　　　1365

Met Val Val Ser Ile Phe Asp Pro Pro Val Asn Trp Leu Pro Pro
　　1370　　　　　　　　1375　　　　　　　　1380

Gly Tyr Val Val Asn Gln Asp Lys Ser Asn Thr Asp Lys Trp Glu
　　1385　　　　　　　　1390　　　　　　　　1395

Lys Asp Glu Met Thr Lys Asp Cys Met Leu Ala Asn Gly Lys Leu
　　1400　　　　　　　　1405　　　　　　　　1410

Asp Glu Asp Tyr Glu Glu Glu Asp Glu Glu Glu Ser Leu Met
　　1415　　　　　　　　1420　　　　　　　　1425

Trp Arg Ala Pro Lys Glu Glu Ala Asp Tyr Glu Asp Asp Phe Leu
　　1430　　　　　　　　1435　　　　　　　　1440

Glu Tyr Asp Gln Glu His Ile Arg Phe Ile Asp Asn Met Leu Met
　　1445　　　　　　　　1450　　　　　　　　1455

Gly Ser Gly Ala Phe Val Lys Lys Ile Ser Leu Ser Pro Phe Ser
　　1460　　　　　　　　1465　　　　　　　　1470

Thr Thr Asp Ser Ala Tyr Glu Trp Lys Met Pro Lys Lys Ser Ser
　　1475　　　　　　　　1480　　　　　　　　1485

Leu Gly Ser Met Pro Phe Ser Ser Asp Phe Glu Asp Phe Asp Tyr
　　1490　　　　　　　　1495　　　　　　　　1500

```
Ser Ser Trp Asp Ala Met Cys Tyr Leu Asp Pro Ser Lys Ala Val
1505                1510                1515

Glu Glu Asp Asp Phe Val Val Gly Phe Trp Asn Pro Ser Glu Glu
1520                1525                1530

Asn Cys Gly Val Asp Thr Gly Lys Gln Ser Ile Ser Tyr Asp Leu
1535                1540                1545

His Thr Glu Gln Cys Ile Ala Asp Lys Ser Ile Ala Asp Cys Val
1550                1555                1560

Glu Ala Leu Leu Gly Cys Tyr Leu Thr Ser Cys Gly Glu Arg Ala
1565                1570                1575

Ala Gln Leu Phe Leu Cys Ser Leu Gly Leu Lys Val Leu Pro Val
1580                1585                1590

Ile Lys Arg Thr Asp Arg Glu Lys Ala Leu Cys Pro Thr Arg Glu
1595                1600                1605

Asn Phe Asn Ser Gln Gln Lys Asn Leu Ser Val Ser Cys Ala Ala
1610                1615                1620

Ala Ser Val Ala Ser Ser Arg Ser Ser Val Leu Lys Asp Ser Glu
1625                1630                1635

Tyr Gly Cys Leu Lys Ile Pro Pro Arg Cys Met Phe Asp His Pro
1640                1645                1650

Asp Ala Asp Lys Thr Leu Asn His Leu Ile Ser Gly Phe Glu Asn
1655                1660                1665

Phe Glu Lys Lys Ile Asn Tyr Arg Phe Lys Asn Lys Ala Tyr Leu
1670                1675                1680

Leu Gln Ala Phe Thr His Ala Ser Tyr His Tyr Asn Thr Ile Thr
1685                1690                1695

Asp Cys Tyr Gln Arg Leu Glu Phe Leu Gly Asp Ala Ile Leu Asp
1700                1705                1710

Tyr Leu Ile Thr Lys His Leu Tyr Glu Asp Pro Arg Gln His Ser
1715                1720                1725

Pro Gly Val Leu Thr Asp Leu Arg Ser Ala Leu Val Asn Asn Thr
1730                1735                1740

Ile Phe Ala Ser Leu Ala Val Lys Tyr Asp Tyr His Lys Tyr Phe
1745                1750                1755

Lys Ala Val Ser Pro Glu Leu Phe His Val Ile Asp Asp Phe Val
1760                1765                1770

Gln Phe Gln Leu Glu Lys Asn Glu Met Gln Gly Met Asp Ser Glu
1775                1780                1785

Leu Arg Arg Ser Glu Glu Asp Glu Glu Lys Glu Glu Asp Ile Glu
1790                1795                1800

Val Pro Lys Ala Met Gly Asp Ile Phe Glu Ser Leu Ala Gly Ala
1805                1810                1815

Ile Tyr Met Asp Ser Gly Met Ser Leu Glu Thr Val Trp Gln Val
1820                1825                1830

Tyr Tyr Pro Met Met Arg Pro Leu Ile Glu Lys Phe Ser Ala Asn
1835                1840                1845

Val Pro Arg Ser Pro Val Arg Glu Leu Leu Glu Met Glu Pro Glu
1850                1855                1860

Thr Ala Lys Phe Ser Pro Ala Glu Arg Thr Tyr Asp Gly Lys Val
1865                1870                1875

Arg Val Thr Val Glu Val Val Gly Lys Gly Lys Phe Lys Gly Val
1880                1885                1890
```

Gly Arg Ser Tyr Arg Ile Ala Lys Ser Ala Ala Ala Arg Arg Ala
1895                1900                1905

Leu Arg Ser Leu Lys Ala Asn Gln Pro Gln Val Pro Asn Ser
1910                1915                1920

<210> SEQ ID NO 10
<211> LENGTH: 647
<212> TYPE: PRT
<213> ORGANISM: Homo sapiens

<400> SEQUENCE: 10

Asp Ser Glu Gln Ser Pro Ser Ile Gly Tyr Ser Arg Thr Leu Gly
1               5                   10                  15

Pro Asn Pro Gly Leu Ile Leu Gln Ala Leu Thr Leu Ser Asn Ala Ser
                20                  25                  30

Asp Gly Phe Asn Leu Glu Arg Leu Glu Met Leu Gly Asp Ser Phe Leu
            35                  40                  45

Lys His Ala Ile Thr Thr Tyr Leu Phe Cys Thr Tyr Pro Asp Ala His
        50                  55                  60

Glu Gly Arg Leu Ser Tyr Met Arg Ser Lys Lys Val Ser Asn Cys Asn
65                  70                  75                  80

Leu Tyr Arg Leu Gly Lys Lys Lys Gly Leu Pro Ser Arg Met Val Val
                    85                  90                  95

Ser Ile Phe Asp Pro Pro Val Asn Trp Leu Pro Pro Gly Tyr Val Val
                100                 105                 110

Asn Gln Asp Lys Ser Asn Thr Asp Lys Trp Glu Lys Asp Glu Met Thr
                115                 120                 125

Lys Asp Cys Met Leu Ala Asn Gly Lys Leu Asp Glu Asp Tyr Glu Glu
            130                 135                 140

Glu Asp Glu Glu Glu Ser Leu Met Trp Arg Ala Pro Lys Glu Glu
145                 150                 155                 160

Ala Asp Tyr Glu Asp Asp Phe Leu Glu Tyr Asp Gln Glu His Ile Arg
                    165                 170                 175

Phe Ile Asp Asn Met Leu Met Gly Ser Gly Ala Phe Val Lys Lys Ile
                180                 185                 190

Ser Leu Ser Pro Phe Ser Thr Thr Asp Ser Ala Tyr Glu Trp Lys Met
            195                 200                 205

Pro Lys Lys Ser Ser Leu Gly Ser Met Pro Phe Ser Ser Asp Phe Glu
        210                 215                 220

Asp Phe Asp Tyr Ser Ser Trp Asp Ala Met Cys Tyr Leu Asp Pro Ser
225                 230                 235                 240

Lys Ala Val Glu Glu Asp Asp Phe Val Val Gly Phe Trp Asn Pro Ser
                    245                 250                 255

Glu Glu Asn Cys Gly Val Asp Thr Gly Lys Gln Ser Ile Ser Tyr Asp
                260                 265                 270

Leu His Thr Glu Gln Cys Ile Ala Asp Lys Ser Ile Ala Asp Cys Val
            275                 280                 285

Glu Ala Leu Leu Gly Cys Tyr Leu Thr Ser Cys Gly Glu Arg Ala Ala
        290                 295                 300

Gln Leu Phe Leu Cys Ser Leu Gly Leu Lys Val Leu Pro Val Ile Lys
305                 310                 315                 320

Arg Thr Asp Arg Glu Lys Ala Leu Cys Pro Thr Arg Glu Asn Phe Asn
                    325                 330                 335

Ser Gln Gln Lys Asn Leu Ser Val Ser Cys Ala Ala Ser Val Ala
                340                 345                 350

```
Ser Ser Arg Ser Ser Val Leu Lys Asp Ser Glu Tyr Gly Cys Leu Lys
            355                 360                 365

Ile Pro Pro Arg Cys Met Phe Asp His Pro Asp Ala Asp Lys Thr Leu
370                 375                 380

Asn His Leu Ile Ser Gly Phe Glu Asn Phe Lys Lys Ile Asn Tyr
385                 390                 395                 400

Arg Phe Lys Asn Lys Ala Tyr Leu Leu Gln Ala Phe Thr His Ala Ser
                405                 410                 415

Tyr His Tyr Asn Thr Ile Thr Asp Cys Tyr Gln Arg Leu Glu Phe Leu
            420                 425                 430

Gly Asp Ala Ile Leu Asp Tyr Leu Ile Thr Lys His Leu Tyr Glu Asp
                435                 440                 445

Pro Arg Gln His Ser Pro Gly Val Leu Thr Asp Leu Arg Ser Ala Leu
        450                 455                 460

Val Asn Asn Thr Ile Phe Ala Ser Leu Ala Val Lys Tyr Asp Tyr His
465                 470                 475                 480

Lys Tyr Phe Lys Ala Val Ser Pro Glu Leu Phe His Val Ile Asp Asp
                485                 490                 495

Phe Val Gln Phe Gln Leu Glu Lys Asn Glu Met Gln Gly Met Asp Ser
                500                 505                 510

Glu Leu Arg Arg Ser Glu Glu Asp Glu Glu Lys Glu Glu Asp Ile Glu
            515                 520                 525

Val Pro Lys Ala Met Gly Asp Ile Phe Glu Ser Leu Ala Gly Ala Ile
530                 535                 540

Tyr Met Asp Ser Gly Met Ser Leu Glu Thr Val Trp Gln Val Tyr Tyr
545                 550                 555                 560

Pro Met Met Arg Pro Leu Ile Glu Lys Phe Ser Ala Asn Val Pro Arg
                565                 570                 575

Ser Pro Val Arg Glu Leu Leu Glu Met Glu Pro Glu Thr Ala Lys Phe
            580                 585                 590

Ser Pro Ala Glu Arg Thr Tyr Asp Gly Lys Val Arg Val Thr Val Glu
        595                 600                 605

Val Val Gly Lys Gly Lys Phe Lys Gly Val Gly Arg Ser Tyr Arg Ile
610                 615                 620

Ala Lys Ser Ala Ala Ala Arg Arg Ala Leu Arg Ser Leu Lys Ala Asn
625                 630                 635                 640

Gln Pro Gln Val Pro Asn Ser
                645

<210> SEQ ID NO 11
<211> LENGTH: 1318
<212> TYPE: PRT
<213> ORGANISM: Homo sapiens

<400> SEQUENCE: 11

Met Asp Asp Asp Val Phe Pro Pro Tyr Val Leu Arg Pro Asp Asp
1               5                   10                  15

Gly Gly Pro Arg Val Thr Ile Asn Thr Ala Ile Gly His Ile Asn Arg
            20                  25                  30

Tyr Cys Ala Arg Leu Pro Ser Asp Pro Phe Thr His Leu Ala Pro Lys
        35                  40                  45

Cys Arg Thr Arg Glu Leu Pro Asp Gly Thr Phe Tyr Ser Thr Leu Tyr
    50                  55                  60

Leu Pro Ile Asn Ser Pro Leu Arg Ala Ser Ile Val Gly Pro Pro Met
```

```
            65                  70                  75                  80

Ser Cys Val Arg Leu Ala Glu Arg Val Ala Leu Ile Cys Cys Glu
                    85                  90                  95

Lys Leu His Lys Ile Gly Glu Leu Asp Asp His Leu Met Pro Val Gly
                100                 105                 110

Lys Glu Thr Val Lys Tyr Glu Glu Leu Asp Leu His Asp Glu Glu
                115                 120                 125

Glu Thr Ser Val Pro Gly Arg Pro Gly Ser Thr Lys Arg Arg Gln Cys
130                 135                 140

Tyr Pro Lys Ala Ile Pro Glu Cys Leu Arg Asp Ser Tyr Pro Arg Pro
145                 150                 155                 160

Asp Gln Pro Cys Tyr Leu Tyr Val Ile Gly Met Val Leu Thr Thr Pro
                165                 170                 175

Leu Pro Asp Glu Leu Asn Phe Arg Arg Arg Lys Leu Tyr Pro Pro Glu
                180                 185                 190

Asp Thr Thr Arg Cys Phe Gly Ile Leu Thr Ala Lys Pro Ile Pro Gln
                195                 200                 205

Ile Pro His Phe Pro Val Tyr Thr Arg Ser Gly Glu Val Thr Ile Ser
210                 215                 220

Ile Glu Leu Lys Lys Ser Gly Phe Met Leu Ser Leu Gln Met Leu Glu
225                 230                 235                 240

Leu Ile Thr Arg Leu His Gln Tyr Ile Phe Ser His Ile Leu Arg Leu
                245                 250                 255

Glu Lys Pro Ala Leu Glu Phe Lys Pro Thr Asp Ala Asp Ser Ala Tyr
                260                 265                 270

Cys Val Leu Pro Leu Asn Val Val Asn Asp Ser Ser Thr Leu Asp Ile
                275                 280                 285

Asp Phe Lys Phe Met Glu Asp Ile Glu Lys Ser Glu Ala Arg Ile Gly
                290                 295                 300

Ile Pro Ser Thr Lys Tyr Thr Lys Glu Thr Pro Phe Val Phe Lys Leu
305                 310                 315                 320

Glu Asp Tyr Gln Asp Ala Val Ile Ile Pro Arg Tyr Arg Asn Phe Asp
                325                 330                 335

Gln Pro His Arg Phe Tyr Val Ala Asp Val Tyr Thr Asp Leu Thr Pro
                340                 345                 350

Leu Ser Lys Phe Pro Ser Pro Glu Tyr Glu Thr Phe Ala Glu Tyr Tyr
                355                 360                 365

Lys Thr Lys Tyr Asn Leu Asp Leu Thr Asn Leu Asn Gln Pro Leu Leu
                370                 375                 380

Asp Val Asp His Thr Ser Ser Arg Leu Asn Leu Leu Thr Pro Arg His
385                 390                 395                 400

Leu Asn Gln Lys Gly Lys Ala Leu Pro Leu Ser Ser Ala Glu Lys Arg
                405                 410                 415

Lys Ala Lys Trp Glu Ser Leu Gln Asn Lys Gln Ile Leu Val Pro Glu
                420                 425                 430

Leu Cys Ala Ile His Pro Ile Pro Ala Ser Leu Trp Arg Lys Ala Val
                435                 440                 445

Cys Leu Pro Ser Ile Leu Tyr Arg Leu His Cys Leu Leu Thr Ala Glu
                450                 455                 460

Glu Leu Arg Ala Gln Thr Ala Ser Asp Ala Gly Val Gly Val Arg Ser
465                 470                 475                 480

Leu Pro Ala Asp Phe Arg Tyr Pro Asn Leu Asp Phe Gly Trp Lys Lys
                485                 490                 495
```

```
Ser Ile Asp Ser Lys Ser Phe Ile Ser Ile Ser Asn Ser Ser Ala
            500             505             510

Glu Asn Asp Asn Tyr Cys Lys His Ser Thr Ile Val Pro Glu Asn Ala
            515             520             525

Ala His Gln Gly Ala Asn Arg Thr Ser Ser Leu Glu Asn His Asp Gln
            530             535             540

Met Ser Val Asn Cys Arg Thr Leu Leu Ser Glu Ser Pro Gly Lys Leu
545             550             555             560

His Val Glu Val Ser Ala Asp Leu Thr Ala Ile Asn Gly Leu Ser Tyr
                565             570             575

Asn Gln Asn Leu Ala Asn Gly Ser Tyr Asp Leu Ala Asn Arg Asp Phe
            580             585             590

Cys Gln Gly Asn Gln Leu Asn Tyr Tyr Lys Gln Glu Ile Pro Val Gln
            595             600             605

Pro Thr Thr Ser Tyr Ser Ile Gln Asn Leu Tyr Ser Tyr Glu Asn Gln
            610             615             620

Pro Gln Pro Ser Asp Glu Cys Thr Leu Leu Ser Asn Lys Tyr Leu Asp
625             630             635             640

Gly Asn Ala Asn Lys Ser Thr Ser Asp Gly Ser Pro Val Met Ala Val
                645             650             655

Met Pro Gly Thr Thr Asp Thr Ile Gln Val Leu Lys Gly Arg Met Asp
            660             665             670

Ser Glu Gln Ser Pro Ser Ile Gly Tyr Ser Ser Arg Thr Leu Gly Pro
            675             680             685

Asn Pro Gly Leu Ile Leu Gln Ala Leu Thr Leu Ser Asn Ala Ser Asp
            690             695             700

Gly Phe Asn Leu Glu Arg Leu Glu Met Leu Gly Asp Ser Phe Leu Lys
705             710             715             720

His Ala Ile Thr Thr Tyr Leu Phe Cys Thr Tyr Pro Asp Ala His Glu
                725             730             735

Gly Arg Leu Ser Tyr Met Arg Ser Lys Lys Val Ser Asn Cys Asn Leu
            740             745             750

Tyr Arg Leu Gly Lys Lys Gly Leu Pro Ser Arg Met Val Val Ser
            755             760             765

Ile Phe Asp Pro Pro Val Asn Trp Leu Pro Pro Gly Tyr Val Val Asn
770             775             780

Gln Asp Lys Ser Asn Thr Asp Lys Trp Glu Lys Asp Glu Met Thr Lys
785             790             795             800

Asp Cys Met Leu Ala Asn Gly Lys Leu Asp Glu Asp Tyr Glu Glu Glu
            805             810             815

Asp Glu Glu Glu Ser Leu Met Trp Arg Ala Pro Lys Glu Glu Ala
            820             825             830

Asp Tyr Glu Asp Asp Phe Leu Glu Tyr Asp Gln Glu His Ile Arg Phe
            835             840             845

Ile Asp Asn Met Leu Met Gly Ser Gly Ala Phe Val Lys Lys Ile Ser
            850             855             860

Leu Ser Pro Phe Ser Thr Thr Asp Ser Ala Tyr Glu Trp Lys Met Pro
865             870             875             880

Lys Lys Ser Ser Leu Gly Ser Met Pro Phe Ser Ser Asp Phe Glu Asp
                885             890             895

Phe Asp Tyr Ser Ser Trp Asp Ala Met Cys Tyr Leu Asp Pro Ser Lys
            900             905             910
```

-continued

```
Ala Val Glu Glu Asp Asp Phe Val Val Gly Phe Trp Asn Pro Ser Glu
            915                 920                 925
Glu Asn Cys Gly Val Asp Thr Gly Lys Gln Ser Ile Ser Tyr Asp Leu
    930                 935                 940
His Thr Glu Gln Cys Ile Ala Asp Lys Ser Ile Ala Asp Cys Val Glu
945                 950                 955                 960
Ala Leu Leu Gly Cys Tyr Leu Thr Ser Cys Gly Glu Arg Ala Ala Gln
                965                 970                 975
Leu Phe Leu Cys Ser Leu Gly Leu Lys Val Leu Pro Val Ile Lys Arg
            980                 985                 990
Thr Asp Arg Glu Lys Ala Leu Cys Pro Thr Arg Glu Asn Phe Asn Ser
        995                 1000                1005
Gln Gln Lys Asn Leu Ser Val Ser Cys Ala Ala Ala Ser Val Ala
    1010                1015                1020
Ser Ser Arg Ser Ser Val Leu Lys Asp Ser Glu Tyr Gly Cys Leu
    1025                1030                1035
Lys Ile Pro Pro Arg Cys Met Phe Asp His Pro Asp Ala Asp Lys
    1040                1045                1050
Thr Leu Asn His Leu Ile Ser Gly Phe Glu Asn Phe Glu Lys Lys
    1055                1060                1065
Ile Asn Tyr Arg Phe Lys Asn Lys Ala Tyr Leu Leu Gln Ala Phe
    1070                1075                1080
Thr His Ala Ser Tyr His Tyr Asn Thr Ile Thr Asp Cys Tyr Gln
    1085                1090                1095
Arg Leu Glu Phe Leu Gly Asp Ala Ile Leu Asp Tyr Leu Ile Thr
    1100                1105                1110
Lys His Leu Tyr Glu Asp Pro Arg Gln His Ser Pro Gly Val Leu
    1115                1120                1125
Thr Asp Leu Arg Ser Ala Leu Val Asn Asn Thr Ile Phe Ala Ser
    1130                1135                1140
Leu Ala Val Lys Tyr Asp Tyr His Lys Tyr Phe Lys Ala Val Ser
    1145                1150                1155
Pro Glu Leu Phe His Val Ile Asp Asp Phe Val Gln Phe Gln Leu
    1160                1165                1170
Glu Lys Asn Glu Met Gln Gly Met Asp Ser Glu Leu Arg Arg Ser
    1175                1180                1185
Glu Glu Asp Glu Glu Lys Glu Glu Asp Ile Glu Val Pro Lys Ala
    1190                1195                1200
Met Gly Asp Ile Phe Glu Ser Leu Ala Gly Ala Ile Tyr Met Asp
    1205                1210                1215
Ser Gly Met Ser Leu Glu Thr Val Trp Gln Val Tyr Tyr Pro Met
    1220                1225                1230
Met Arg Pro Leu Ile Glu Lys Phe Ser Ala Asn Val Pro Arg Ser
    1235                1240                1245
Pro Val Arg Glu Leu Leu Glu Met Glu Pro Glu Thr Ala Lys Phe
    1250                1255                1260
Ser Pro Ala Glu Arg Thr Tyr Asp Gly Lys Val Arg Val Thr Val
    1265                1270                1275
Glu Val Val Gly Lys Gly Lys Phe Lys Gly Val Gly Arg Ser Tyr
    1280                1285                1290
Arg Ile Ala Lys Ser Ala Ala Ala Arg Arg Ala Leu Arg Ser Leu
    1295                1300                1305
Lys Ala Asn Gln Pro Gln Val Pro Asn Ser
```

<210> SEQ ID NO 12
<211> LENGTH: 257
<212> TYPE: PRT
<213> ORGANISM: Homo sapiens

<400> SEQUENCE: 12

Phe Glu Asn Phe Glu Lys Lys Ile Asn Tyr Arg Phe Lys Asn Lys Ala
1               5                   10                  15

Tyr Leu Leu Gln Ala Phe Thr His Ala Ser Tyr His Tyr Asn Thr Ile
            20                  25                  30

Thr Asp Cys Tyr Gln Arg Leu Glu Phe Leu Gly Asp Ala Ile Leu Asp
        35                  40                  45

Tyr Leu Ile Thr Lys His Leu Tyr Glu Asp Pro Arg Gln His Ser Pro
    50                  55                  60

Gly Val Leu Thr Asp Leu Arg Ser Ala Leu Val Asn Asn Thr Ile Phe
65                  70                  75                  80

Ala Ser Leu Ala Val Lys Tyr Asp Tyr His Lys Tyr Phe Lys Ala Val
                85                  90                  95

Ser Pro Glu Leu Phe His Val Ile Asp Asp Phe Val Gln Phe Gln Leu
            100                 105                 110

Glu Lys Asn Glu Met Gln Gly Met Asp Ser Glu Leu Arg Arg Ser Glu
        115                 120                 125

Glu Asp Glu Glu Lys Glu Glu Asp Ile Glu Val Pro Lys Ala Met Gly
    130                 135                 140

Asp Ile Phe Glu Ser Leu Ala Gly Ala Ile Tyr Met Asp Ser Gly Met
145                 150                 155                 160

Ser Leu Glu Thr Val Trp Gln Val Tyr Tyr Pro Met Met Arg Pro Leu
                165                 170                 175

Ile Glu Lys Phe Ser Ala Asn Val Pro Arg Ser Pro Val Arg Glu Leu
            180                 185                 190

Leu Glu Met Glu Pro Glu Thr Ala Lys Phe Ser Pro Ala Glu Arg Thr
        195                 200                 205

Tyr Asp Gly Lys Val Arg Val Thr Val Glu Val Gly Lys Gly Lys
    210                 215                 220

Phe Lys Gly Val Gly Arg Ser Tyr Arg Ile Ala Lys Ser Ala Ala Ala
225                 230                 235                 240

Arg Arg Ala Leu Arg Ser Leu Lys Ala Asn Gln Pro Gln Val Pro Asn
                245                 250                 255

Ser

<210> SEQ ID NO 13
<211> LENGTH: 247
<212> TYPE: PRT
<213> ORGANISM: Homo sapiens

<400> SEQUENCE: 13

Phe Glu Asn Phe Glu Lys Lys Ile Asn Tyr Arg Phe Lys Asn Lys Ala
1               5                   10                  15

Tyr Leu Leu Gln Ala Phe Thr His Ala Ser Tyr His Tyr Asn Thr Ile
            20                  25                  30

Thr Asp Cys Tyr Gln Arg Leu Glu Phe Leu Gly Asp Ala Ile Leu Asp
        35                  40                  45

Tyr Leu Ile Thr Lys His Leu Tyr Glu Asp Pro Arg Gln His Ser Pro
    50                  55                  60

-continued

Gly Val Leu Thr Asp Leu Arg Ser Ala Leu Val Asn Asn Thr Ile Phe
65                  70                  75                  80

Ala Ser Leu Ala Val Lys Tyr Asp Tyr His Lys Tyr Phe Lys Ala Val
                85                  90                  95

Ser Pro Glu Leu Phe His Val Ile Asp Asp Phe Val Gln Phe Gln Leu
            100                 105                 110

Glu Lys Asn Glu Met Gln Gly Met Asp Ser Glu Leu Arg Arg Ser Glu
        115                 120                 125

Glu Asp Glu Glu Lys Glu Glu Asp Ile Glu Val Pro Lys Ala Met Gly
    130                 135                 140

Asp Ile Phe Glu Ser Leu Ala Gly Ala Ile Tyr Met Asp Ser Gly Met
145                 150                 155                 160

Ser Leu Glu Thr Val Trp Gln Val Tyr Tyr Pro Met Met Arg Pro Leu
                165                 170                 175

Ile Glu Lys Phe Ser Ala Asn Val Pro Arg Ser Pro Val Arg Glu Leu
            180                 185                 190

Leu Glu Met Glu Pro Glu Thr Ala Lys Phe Ser Pro Ala Glu Arg Thr
        195                 200                 205

Tyr Asp Gly Lys Val Arg Val Thr Val Glu Val Gly Lys Gly Lys
    210                 215                 220

Phe Lys Gly Val Gly Arg Ser Tyr Arg Ile Ala Lys Ser Ala Ala Ala
225                 230                 235                 240

Arg Arg Ala Leu Arg Ser Leu
                245

<210> SEQ ID NO 14
<211> LENGTH: 234
<212> TYPE: PRT
<213> ORGANISM: Homo sapiens

<400> SEQUENCE: 14

Phe Glu Asn Phe Glu Lys Lys Ile Asn Tyr Arg Phe Lys Asn Lys Ala
1               5                   10                  15

Tyr Leu Leu Gln Ala Phe Thr His Ala Ser Tyr His Tyr Asn Thr Ile
                20                  25                  30

Thr Asp Cys Tyr Gln Arg Leu Glu Phe Leu Gly Asp Ala Ile Leu Asp
            35                  40                  45

Tyr Leu Ile Thr Lys His Leu Tyr Glu Asp Pro Arg Gln His Ser Pro
        50                  55                  60

Gly Val Leu Thr Asp Leu Arg Ser Ala Leu Val Asn Asn Thr Ile Phe
65                  70                  75                  80

Ala Ser Leu Ala Val Lys Tyr Asp Tyr His Lys Tyr Phe Lys Ala Val
                85                  90                  95

Ser Pro Glu Leu Phe His Val Ile Asp Asp Phe Val Gln Phe Gln Leu
            100                 105                 110

Glu Lys Asn Glu Met Gln Gly Met Asp Glu Asp Ile Glu Val Pro Lys
        115                 120                 125

Ala Met Gly Asp Ile Phe Glu Ser Leu Ala Gly Ala Ile Tyr Met Asp
    130                 135                 140

Ser Gly Met Ser Leu Glu Thr Val Trp Gln Val Tyr Tyr Pro Met Met
145                 150                 155                 160

Arg Pro Leu Ile Glu Lys Phe Ser Ala Asn Val Pro Arg Ser Pro Val
                165                 170                 175

Arg Glu Leu Leu Glu Met Glu Pro Glu Thr Ala Lys Phe Ser Pro Ala

```
                180              185              190
Glu Arg Thr Tyr Asp Gly Lys Val Arg Val Thr Val Glu Val Val Gly
            195                  200                 205
Lys Gly Lys Phe Lys Gly Val Gly Arg Ser Tyr Arg Ile Ala Lys Ser
        210                  215                 220
Ala Ala Ala Arg Arg Ala Leu Arg Ser Leu
225                 230

<210> SEQ ID NO 15
<211> LENGTH: 550
<212> TYPE: PRT
<213> ORGANISM: Homo sapiens

<400> SEQUENCE: 15

Met Asp Ser Glu Gln Ser Pro Ser Ile Gly Tyr Ser Ser Arg Thr Leu
1               5                   10                  15
Gly Pro Asn Pro Gly Leu Ile Leu Gln Ala Leu Thr Leu Ser Asn Ala
            20                  25                  30
Ser Asp Gly Phe Asn Leu Glu Arg Leu Glu Met Leu Gly Asp Ser Phe
        35                  40                  45
Leu Lys His Ala Ile Thr Thr Tyr Leu Phe Cys Thr Tyr Pro Asp Ala
    50                  55                  60
His Glu Gly Arg Leu Ser Tyr Met Arg Ser Lys Lys Val Ser Asn Cys
65                  70                  75                  80
Asn Leu Tyr Arg Leu Gly Lys Lys Lys Gly Leu Pro Ser Arg Met Val
                85                  90                  95
Val Ser Ile Phe Asp Pro Pro Val Asn Trp Leu Pro Pro Gly Tyr Val
            100                 105                 110
Val Asn Gln Asp Lys Ser Asn Thr Asp Lys Trp Glu Lys Asp Glu Met
        115                 120                 125
Thr Lys Asp Cys Met Leu Ala Asn Gly Lys Leu Asp Glu Asp Tyr Glu
    130                 135                 140
Glu Glu Asp Glu Glu Glu Glu Ser Leu Met Trp Arg Ala Pro Lys Glu
145                 150                 155                 160
Glu Ala Asp Tyr Glu Asp Asp Phe Leu Glu Tyr Asp Gln Glu His Ile
                165                 170                 175
Arg Phe Ile Asp Asn Met Leu Met Gly Ser Gly Ala Phe Val Lys Lys
            180                 185                 190
Ile Ser Leu Ser Pro Phe Ser Thr Thr Asp Ser Ala Tyr Glu Trp Lys
        195                 200                 205
Met Pro Lys Lys Ser Ser Leu Gly Ser Met Pro Phe Ser Ser Asp Phe
    210                 215                 220
Glu Asp Phe Asp Tyr Ser Ser Trp Asp Ala Met Cys Tyr Leu Asp Pro
225                 230                 235                 240
Ser Lys Ala Val Glu Glu Asp Asp Phe Val Val Gly Phe Trp Asn Pro
                245                 250                 255
Ser Glu Glu Asn Cys Gly Val Asp Thr Gly Lys Gln Ser Ile Ser Tyr
            260                 265                 270
Asp Leu His Thr Glu Gln Cys Ile Ala Asp Lys Ser Ile Ala Asp Cys
        275                 280                 285
Val Glu Ala Leu Leu Gly Cys Tyr Leu Thr Ser Cys Gly Glu Arg Ala
    290                 295                 300
Ala Gln Leu Phe Leu Cys Ser Leu Gly Leu Lys Val Leu Pro Val Ile
305                 310                 315                 320
```

Lys Arg Thr Asp Arg Glu Lys Ala Leu Cys Pro Thr Arg Glu Asn Phe
            325                 330                 335

Asn Ser Gln Gln Lys Asn Leu Ser Val Ser Cys Ala Ala Ala Ser Val
        340                 345                 350

Ala Ser Ser Arg Ser Ser Val Leu Lys Asp Ser Glu Tyr Gly Cys Leu
            355                 360                 365

Lys Ile Pro Pro Arg Cys Met Phe Asp His Pro Asp Ala Asp Lys Thr
370                 375                 380

Leu Asn His Leu Ile Ser Gly Phe Glu Asn Phe Glu Lys Lys Ile Asn
385                 390                 395                 400

Tyr Arg Phe Lys Asn Lys Ala Tyr Leu Leu Gln Ala Phe Thr His Ala
            405                 410                 415

Ser Tyr His Tyr Asn Thr Ile Thr Asp Cys Tyr Gln Arg Leu Glu Phe
            420                 425                 430

Leu Gly Asp Ala Ile Leu Asp Tyr Leu Ile Thr Lys His Leu Tyr Glu
            435                 440                 445

Asp Pro Arg Gln His Ser Pro Gly Val Leu Thr Asp Leu Arg Ser Ala
        450                 455                 460

Leu Val Asn Asn Thr Ile Phe Ala Ser Leu Ala Val Lys Tyr Asp Tyr
465                 470                 475                 480

His Lys Tyr Phe Lys Ala Val Ser Pro Glu Leu Phe His Val Ile Asp
            485                 490                 495

Asp Phe Val Gln Phe Gln Leu Glu Lys Asn Glu Met Gln Gly Met Asp
                500                 505                 510

Ser Glu Leu Arg Arg Ser Glu Glu Asp Glu Lys Glu Glu Asp Ile
            515                 520                 525

Glu Val Pro Lys Ala Met Gly Asp Ile Phe Glu Ser Leu Ala Gly Ala
        530                 535                 540

Ile Tyr Met Asp Ser Gly
545                 550

<210> SEQ ID NO 16
<211> LENGTH: 549
<212> TYPE: PRT
<213> ORGANISM: Homo sapiens

<400> SEQUENCE: 16

Asp Ser Glu Gln Ser Pro Ser Ile Gly Tyr Ser Ser Arg Thr Leu Gly
1               5                   10                  15

Pro Asn Pro Gly Leu Ile Leu Gln Ala Leu Thr Leu Ser Asn Ala Ser
            20                  25                  30

Asp Gly Phe Asn Leu Glu Arg Leu Glu Met Leu Gly Asp Ser Phe Leu
        35                  40                  45

Lys His Ala Ile Thr Thr Tyr Leu Phe Cys Thr Tyr Pro Asp Ala His
50                  55                  60

Glu Gly Arg Leu Ser Tyr Met Arg Ser Lys Lys Val Ser Asn Cys Asn
65                  70                  75                  80

Leu Tyr Arg Leu Gly Lys Lys Lys Gly Leu Pro Ser Arg Met Val Val
            85                  90                  95

Ser Ile Phe Asp Pro Pro Val Asn Trp Leu Pro Pro Gly Tyr Val Val
        100                 105                 110

Asn Gln Asp Lys Ser Asn Thr Asp Lys Trp Glu Lys Asp Glu Met Thr
    115                 120                 125

Lys Asp Cys Met Leu Ala Asn Gly Lys Leu Asp Glu Asp Tyr Glu Glu
130                 135                 140

-continued

```
Glu Asp Glu Glu Glu Ser Leu Met Trp Arg Ala Pro Lys Glu Glu
145                 150                 155                 160

Ala Asp Tyr Glu Asp Asp Phe Leu Glu Tyr Asp Gln Glu His Ile Arg
            165                 170                 175

Phe Ile Asp Asn Met Leu Met Gly Ser Gly Ala Phe Val Lys Lys Ile
                180                 185                 190

Ser Leu Ser Pro Phe Ser Thr Thr Asp Ser Ala Tyr Glu Trp Lys Met
            195                 200                 205

Pro Lys Lys Ser Ser Leu Gly Ser Met Pro Phe Ser Ser Asp Phe Glu
        210                 215                 220

Asp Phe Asp Tyr Ser Ser Trp Asp Ala Met Cys Tyr Leu Asp Pro Ser
225                 230                 235                 240

Lys Ala Val Glu Glu Asp Asp Phe Val Val Gly Phe Trp Asn Pro Ser
                245                 250                 255

Glu Glu Asn Cys Gly Val Asp Thr Gly Lys Gln Ser Ile Ser Tyr Asp
                260                 265                 270

Leu His Thr Glu Gln Cys Ile Ala Asp Lys Ser Ile Ala Asp Cys Val
            275                 280                 285

Glu Ala Leu Leu Gly Cys Tyr Leu Thr Ser Cys Gly Glu Arg Ala Ala
290                 295                 300

Gln Leu Phe Leu Cys Ser Leu Gly Leu Lys Val Leu Pro Val Ile Lys
305                 310                 315                 320

Arg Thr Asp Arg Glu Lys Ala Leu Cys Pro Thr Arg Glu Asn Phe Asn
                325                 330                 335

Ser Gln Gln Lys Asn Leu Ser Val Ser Cys Ala Ala Ser Val Ala
            340                 345                 350

Ser Ser Arg Ser Ser Val Leu Lys Asp Ser Glu Tyr Gly Cys Leu Lys
            355                 360                 365

Ile Pro Pro Arg Cys Met Phe Asp His Pro Asp Ala Asp Lys Thr Leu
        370                 375                 380

Asn His Leu Ile Ser Gly Phe Glu Asn Phe Glu Lys Lys Ile Asn Tyr
385                 390                 395                 400

Arg Phe Lys Asn Lys Ala Tyr Leu Leu Gln Ala Phe Thr His Ala Ser
                405                 410                 415

Tyr His Tyr Asn Thr Ile Thr Asp Cys Tyr Gln Arg Leu Glu Phe Leu
                420                 425                 430

Gly Asp Ala Ile Leu Asp Tyr Leu Ile Thr Lys His Leu Tyr Glu Asp
            435                 440                 445

Pro Arg Gln His Ser Pro Gly Val Leu Thr Asp Leu Arg Ser Ala Leu
        450                 455                 460

Val Asn Asn Thr Ile Phe Ala Ser Leu Ala Val Lys Tyr Asp Tyr His
465                 470                 475                 480

Lys Tyr Phe Lys Ala Val Ser Pro Glu Leu Phe His Val Ile Asp Asp
                485                 490                 495

Phe Val Gln Phe Gln Leu Glu Lys Asn Glu Met Gln Gly Met Asp Ser
            500                 505                 510

Glu Leu Arg Arg Ser Glu Glu Asp Glu Glu Lys Glu Glu Asp Ile Glu
            515                 520                 525

Val Pro Lys Ala Met Gly Asp Ile Phe Glu Ser Leu Ala Gly Ala Ile
        530                 535                 540

Tyr Met Asp Ser Gly
545
```

<210> SEQ ID NO 17
<211> LENGTH: 10323
<212> TYPE: DNA
<213> ORGANISM: Homo sapiens

<400> SEQUENCE: 17

| | | | | | |
|---|---|---|---|---|---|
| cggaggcgcg | gcgcaggctg | ctgcaggccc | aggtgaatgg | agtaacctga | cagcggggac | 60 |
| gaggcgacgg | cgagcgcgag | gaaatggcgg | cggggcggc | ggcgccgggc | ggctccggga | 120 |
| ggcctgggct | gtgacgcgcg | cgccggagcg | gggtccgatg | gttctcgaag | gcccgcggcg | 180 |
| ccccgtgctg | cagtaagctg | tgctagaaca | aaaatgcaat | gaaagaaaca | ctggatgaat | 240 |
| gaaaagcccct | gctttgcaac | ccctcagcat | ggcaggcctg | cagctcatga | ccctgcttc | 300 |
| ctcaccaatg | gtcctttct | ttggactgcc | atggcaacaa | gaagcaattc | atgataacat | 360 |
| ttatcgcca | agaaaatatc | aggttgaact | gcttgaagca | gctctggatc | ataataccat | 420 |
| cgtctgttta | aacactggct | cagggaagac | atttattgca | gtactactca | ctaaagagct | 480 |
| gtcctatcag | atcaggggag | acttcagcag | aaatggaaaa | aggacggtgt | tcttggtcaa | 540 |
| ctctgcaaac | caggttgctc | aacaagtgtc | agctgtcaga | actcattcag | atctcaaggt | 600 |
| tggggaatac | tcaaacctag | aagtaaatgc | atccttggaca | aaagagagat | ggaaccaaga | 660 |
| gtttactaag | caccaggttc | tcattatgac | ttgctatgtc | gccttgaatg | ttttgaaaaa | 720 |
| tggttactta | tcactgtcag | acattaacct | tttggtgttt | gatgagtgtc | atcttgcaat | 780 |
| cctagaccac | ccctatcgag | aaattatgaa | gctctgtgaa | aattgtccat | catgtcctcg | 840 |
| catttttggga | ctaactgctt | ccatttttaaa | tgggaaatgt | gatccagagg | aattggaaga | 900 |
| aaagattcag | aaactagaga | aaattcttaa | gagtaatgct | gaaactgcaa | ctgacctggt | 960 |
| ggtcttagac | aggtatactt | ctcagccatg | tgagattgtg | gtggattgtg | gaccatttac | 1020 |
| tgacagaagt | gggctttatg | aaagactgct | gatggaatta | gaagaagcac | ttaattttat | 1080 |
| caatgattgt | aatatatctg | tacattcaaa | agaaagagat | tctactttaa | tttcgaaaca | 1140 |
| gatactatca | gactgtcgtg | ccgtattggt | agttctggga | ccctggtgtg | cagataaagt | 1200 |
| agctggaatg | atggtaagag | aactacagaa | atacatcaaa | catgagcaag | aggagctgca | 1260 |
| caggaaattt | ttattgttta | cagacacttt | cctaaggaaa | atacatgcac | tatgtgaaga | 1320 |
| gcacttctca | cctgcctcac | ttgacctgaa | atttgtaact | cctaaagtaa | tcaaactgct | 1380 |
| cgaaatctta | cgcaaatata | accatatga | gcgacagcag | tttgaaagcg | ttgagtggta | 1440 |
| taataataga | aatcaggata | attatgtgtc | atggagtgat | tctgaggatg | atgatgagga | 1500 |
| tgaagaaatt | gaagaaaaag | agaagccaga | gacaaatttt | ccttctcctt | ttaccaacat | 1560 |
| tttgtgcgga | attattttg | tggaaagaag | atacacagca | gttgtcttaa | acagattgat | 1620 |
| aaaggaagct | ggcaaacaag | atccagagct | ggcttatatc | agtagcaatt | tcataactgg | 1680 |
| acatggcatt | gggaagaatc | agcctcgcaa | caaacagatg | gaagcagaat | tcagaaaaca | 1740 |
| ggaagaggta | cttaggaaat | tcgagcaca | tgagaccaac | ctgcttattg | caacaagtat | 1800 |
| tgtagaagag | ggtgttgata | taccaaaatg | caacttggtg | gttcgttttg | atttgcccac | 1860 |
| agaatatcga | tcctatgttc | aatctaaagg | aagagcaagg | gcacccatct | ctaattatat | 1920 |
| aatgttagcg | gatacagaca | aaataaaaag | ttttgaagaa | gaccttaaaa | cctacaaagc | 1980 |
| tattgaaaag | atcttgagaa | acaagtgttc | caagtcggtt | gatactggtg | agactgacat | 2040 |
| tgatcctgtc | atggatgatg | atgacgtttt | cccaccatat | gtgttgaggc | ctgacgatgg | 2100 |
| tggtccacga | gtcacaatca | acacggccat | tggacacatc | aatagatact | gtgctagatt | 2160 |

```
accaagtgat ccgtttactc atctagctcc taaatgcaga acccgagagt tgcctgatgg    2220
tacattttat tcaactcttt atctgccaat taactcacct cttcgagcct ccattgttgg    2280
tccaccaatg agctgtgtac gattggctga aagagttgta gctctcattt gctgtgagaa    2340
actgcacaaa attggcgaac tggatgacca tttgatgcca gttgggaaag agactgttaa    2400
atatgaagag gagcttgatt tgcatgatga agaagagacc agtgttccag gaagaccagg    2460
ttccacgaaa cgaaggcagt gctacccaaa agcaattcca gagtgtttga gggatagtta    2520
tcccagacct gatcagccct gttacctgta tgtgatagga atggttttaa ctacacccttt    2580 acctgatgaa ctcaacttta gaaggcggaa gctctatcct cctgaagata ccacaagatg    2640
ctttggaata ctgacggcca aacccatacc tcagattcca cactttcctg tgtacacacg    2700
ctctggagag gttaccatat ccattgagtt gaagaagtct ggtttcatgt tgtctctaca    2760
aatgcttgag ttgattacaa gacttcacca gtatatattc tcacatattc ttcggcttga    2820
aaaacctgca ctagaattta aacctacaga cgctgattca gcatactgtg ttctacctct    2880
taatgttgtt aatgactcca gcactttgga tattgacttt aaaattcatg aagatattga    2940
gaagtctgaa gctcgcatag gcattcccag tacaaagtat acaaaagaaa caccctttgt    3000
ttttaaatta gaagattacc aagatgccgt tatcattcca agatatcgca attttgatca    3060
gcctcatcga ttttatgtag ctgatgtgta cactgatctt accccactca gtaaattttcc    3120 ttcccctgag tatgaaactt tgcagaata ttataaaaca aagtacaacc ttgacctaac    3180
caatctcaac cagccactgc tggatgtgga ccacacatct tcaagactta atcttttgac    3240
acctcgacat ttgaatcaga aggggaaagc gcttcctta agcagtgctg agaagaggaa    3300
agccaaatgg gaaagtctgc agaataaaca gatactggtt ccagaactct gtgctataca    3360
tccaattcca gcatcactgt ggagaaaagc tgtttgtctc cccagcatac tttatcgcct    3420
tcactgcctt ttgactgcag aggagctaag agcccagact gccagcgatg ctggcgtggg    3480
agtcagatca cttcctgcgg attttagata ccctaactta gacttcgggt ggaaaaaatc    3540
tattgacagc aaatctttca tctcaatttc taactcctct tcagctgaaa atgataatta    3600
ctgtaagcac agcacaattg tccctgaaaa tgctgcacat caaggtgcta atagaacctc    3660
ctctctagaa aatcatgacc aaatgtctgt gaactgcaga acgttgctca gcgagtcccc    3720
tggtaagctc cacgttgaag tttcagcaga tcttacagca attaatggtc tttcttacaa    3780
tcaaaatctc gccaatggca gttatgattt agctaacaga gacttttgcc aaggaaatca    3840
gctaaattac tacaagcagg aaatacccgt gcaaccaact acctcatatt ccattcagaa    3900
tttatacagt tacgagaacc agccccagcc cagcgatgaa tgtactctcc tgagtaataa    3960
ataccttgat ggaaatgcta acaaatctac ctcagatgga agtcctgtga tggccgtaat    4020
gcctggtacg acagacacta ttcaagtgct caagggcagg atggattctg agcagagccc    4080
ttctattggg tactcctcaa ggactcttgg ccccaatcct ggacttattc ttcaggcttt    4140
gactctgtca aacgctagtg atggatttaa cctggagcgg cttgaaatgc ttggcgactc    4200 cttttttaaag catgccatca ccacatatct attttgcact tacccctgatg cgcatgaggg    4260 ccgccttttca tatatgagaa gcaaaaaggt cagcaactgt aatctgtatc gccttggaaa    4320
aaagaaggga ctacccagcc gcatggtggt gtcaatattt gatccccctg tgaattggct    4380
tcctcctggt tatgtagtaa atcaagacaa aagcaacaca gataaatggg aaaaagatga    4440
aatgacaaaa gactgcatgc tggcgaatgg caaactggat gaggattacg aggagggagga    4500
```

```
tgaggaggag gagagcctga tgtggagggc tccgaaggaa gaggctgact atgaagatga    4560
tttcctggag tatgatcagg aacatatcag atttatagat aatatgttaa tggggtcagg    4620
agcttttgta aagaaaatct ctctttctcc tttttcaacc actgattctg catatgaatg    4680
gaaaatgccc aaaaaatcct ccttaggtag tatgccattt tcatcagatt ttgaggattt    4740
tgactacagc tcttgggatg caatgtgcta tctggatcct agcaaagctg ttgaagaaga    4800
tgactttgtg gtggggttct ggaatccatc agaagaaaac tgtggtgttg acacgggaaa    4860
gcagtccatt tcttacgact tgcacactga gcagtgtatt gctgacaaaa gcatagcgga    4920
ctgtgtggaa gccctgctgg gctgctattt aaccagctgt ggggagaggg ctgctcagct    4980
tttcctctgt tcactggggc tgaaggtgct cccggtaatt aaaaggactg atcgggaaaa    5040
ggccctgtgc cctactcggg agaatttcaa cagccaacaa agaacccttt cagtgagctg    5100
tgctgctgct tctgtggcca gttcacgctc ttctgtattg aaagactcgg aatatggttg    5160
tttgaagatt ccaccaagat gtatgtttga tcatccagat gcagataaaa cactgaatca    5220
ccttatatcg gggtttgaaa attttgaaaa gaaaatcaac tacagattca agaataaggc    5280
ttaccttctc caggctttta cacatgcctc ctaccactac aatactatca ctgattgtta    5340
ccagcgctta gaattcctgg gagatgcgat tttggactac ctcataacca agcacccttta   5400 tgaagacccg cggcagcact ccccggggt cctgacagac ctgcggtctg ccctggtcaa    5460
caacaccatc tttgcatcgc tggctgtaaa gtacgactac cacaagtact caaagctgt    5520 ctctcctgag ctcttccatg tcattgatga ctttgtgcag tttcagcttg agaagaatga    5580
aatgcaagga atggattctg agcttaggag atctgaggag gatgaagaga aagaaggaga    5640
tattgaagtt ccaaaggcca tgggggatat ttttgagtcg cttgctggtg ccatttacat    5700
ggatagtggg atgtcactgg agacagtctg gcaggtgtac tatcccatga tgcggccact    5760
aatagaaaag ttttctgcaa atgtaccccg ttcccctgtg cgagaattgc ttgaaatgga    5820
accagaaact gccaaattta gcccggctga gagaacttac gacgggaagg tcagagtcac    5880
tgtggaagta gtaggaaagg ggaaatttaa aggtgttggt cgaagttaca ggattgccaa    5940
atctgcagca gcaagaagag ccctccgaag cctcaaagct aatcaacctc aggttcccaa    6000
tagctgaaac cgcttttttaa aattcaaaac aagaaacaaa acaaaaaaaa ttaaggggaa    6060
aattatttaa atcggaaagg aagacttaaa gttgttagtg agtggaatga attgaaggca    6120
gaatttaaag tttggttgat aacaggatag ataacagaat aaaacattta acatatgtat    6180
aaaattttgg aactaattgt agttttagtt ttttgcgcaa acacaatctt atcttctttc    6240
ctcacttctg ctttgtttaa atcacaagag tgctttaatg atgacattta gcaagtgctc    6300
aaaataattg acaggttttg ttttttttttt tttgagttta tgtcagcttt gcttagtgtt    6360
agaaggccat ggagcttaaa cctccagcag tccctaggat gatgtagatt cttctccatc    6420
tctccgtgtg tgcagtagtg ccagtcctgc agtagttgat aagctgaata gaaagataag    6480
gttttcgaga ggagaagtgc gccaatgttg tcttttcttt ccacgttata ctgtgtaagg    6540
tgatgttccc ggtcgctgtt gcacctgata gtaagggaca gattttttaat gaacattggc    6600 tggcatgttg gtgaatcaca ttttagtttt ctgatgccac atagtcttgc ataaaaaagg    6660
gttcttgcct taaaagtgaa accttcatgg atagtcttta atctctgatc tttttggaac    6720
aaactgtttt acattccttt cattttatta tgcattagac gttgagacag cgtgatactt    6780
acaactcact agtatagttg taacttatta caggatcata ctaaaatttc tgtcatatgt    6840
atactgaaga cattttaaaa accagaatat gtagtctacg gatatttttt atcataaaaa    6900
```

```
tgatctttgg ctaaacaccc cattttacta aagtcctcct gccaggtagt tcccactgat    6960
ggaaatgttt atggcaaata attttgcctt ctaggctgtt gctctaacaa aataaacctt    7020
agacatatca cacctaaaat atgctgcaga ttttataatt gattggttac ttatttaaga    7080
agcaaaacac agcaccttta cccttagtct cctcacataa atttcttact atacttttca    7140
taatgttgca tgcatatttc acctaccaaa gctgtgctgt taatgccgtg aaagtttaac    7200
gtttgcgata aactgccgta attttgatac atctgtgatt taggtcatta atttagataa    7260
actagctcat tatttccatc tttggaaaag gaaaaaaaaa aaaacttctt taggcatttg    7320
cctaagtttc tttaattaga cttgtaggca ctcttcactt aaatacctca gttcttcttt    7380
tcttttgcat gcattttttcc cctgtttggt gctatgttta tgtattatgc ttgaaatttt    7440 aattttttt tttttgcact gtaactataa tacctcttaa tttacctttt taaaagctgt    7500
gggtcagtct tgcactccca tcaacatacc agtagaggtt tgctgcaatt tgccccgtta    7560
attatgcttg aagtttaaga aagctgagca gaggtgtctc atatttccca gcacatgatt    7620
ctgaacttga tgcttcgtgg aatgctgcat ttatatgtaa gtgacatttg aatactgtcc    7680
ttcctgcttt atctgcatca tccacccaca gagaaatgcc tctgtgcgag tgcaccgaca    7740
gaaaactgtc agctctgctt tctaaggaac cctgagtgag gggggtatta agcttctcca    7800
gtgttttttg ttgtctccaa tcttaaactt aaattgagat ctaaattatt aaacgagttt    7860
ttgagcaaat taggtgactt gttttaaaaa tatttaattc cgatttggaa ccttagatgt    7920
ctatttgatt ttttaaaaaa ccttaatgta agatatgacc agttaaaaca aagcaattct    7980
tgaattatat aactgtaaaa gtgtgcagtt aacaaggctg gatgtgaatt ttattctgag    8040
ggtgatttgt gatcaagttt aatcacaaat ctcttaatat ttataaacta cctgatgcca    8100
ggagcttagg gctttgcatt gtgtctaata cattgatccc agtgttacgg gattctcttg    8160
attcctggca ccaaaatcag attgttttca cagttatgat tcccagtggg agaaaaatgc    8220
ctcaatatat ttgtaacctt aagaagagta tttttttgtt aatactaaga tgttcaaact    8280
tagacatgat taggtcatac attctcaggg gttcaaattt ccttctacca ttcaaatgtt    8340
ttatcaacag caaacttcag ccgtttcact ttttgttgga gaaaaatagt agatttttaat   8400 ttgactcaca gtttgaagca ttctgtgatc ccctggttac tgagttaaaa aataaaaaag   8460
tacgagttag acatatgaaa tggttatgaa cgcttttgtg ctgctgattt ttaatgctgt   8520
aaagttttcc tgtgtttagc ttgttgaaat gttttgcatc tgtcaattaa ggaaaaaaaa   8580
aatcactcta tgttgcccca cttttagagcc ctgtgtgcca ccctgtgttc ctgtgattgc   8640
aatgtgagac cgaatgtaat atggaaaacc taccagtggg gtgtggttgt gccctgagca   8700
cgtgtgtaaa ggactgggga ggcgtgtctt gaaaagcaa ctgcagaaat tccttatgat   8760
gattgtgtgc aagttagtta acatgaacct tcatttgtaa atttttttaaa atttctttta   8820 taatatgctt tccgcagtcc taactatgct gcgttttata atagcttttt cccttctgtt   8880
ctgttcatgt agcacagata agcattgcac ttggtaccat gctttacctc atttcaagaa   8940
aatatgctta acagagagga aaaaaatgtg gtttggcctt gctgctgttt tgatttatgg   9000
aatttgaaaa agataattat aatgcctgca atgtgtcata tactcgcaca acttaaatag   9060 gtcattttttg tctgtggcat ttttactgtt tgtgaaagta tgaaacagat tgttaactg    9120 aactcttaat tatgttttta aaatgttgt tatatttctt ttctttttc ttttatatta    9180 cgtgaagtga tgaaatttag aatgacctct aacactcctg taattgtctt ttaaaatact    9240
```

```
gatatttta tttgttaata atactttgcc ctcagaaaga ttctgatacc ctgccttgac    9300
aacatgaaac ttgaggctgc tttggttcat gaatccaggt gttccccgg cagtcggctt     9360 cttcagtcgc tccctggagg caggtgggca ctgcagagga tcactggaat ccagatcgag    9420
cgcagttcat gcacaaggcc ccgttgattt aaaatattgg atcttgctct gttagggtgt    9480
ctaatccctt tacacaagat tgaagccacc aaactgagac cttgatacct ttttttaact    9540
gcatctgaaa ttatgttaag agtctttaac ccatttgcat tatctgcaga agagaaactc    9600
atgtcatgtt tattacctat atggttgttt taattacatt tgaataatta tattttcca    9660 accactgatt acttttcagg aatttaatta tttccagata aatttcttta ttttatattg    9720
tacatgaaaa gttttaaaga tatgtttaag accaagacta ttaaaatgat ttttaaagtt    9780
gttggagacg ccaatagcaa tatctaggaa atttgcattg agaccattgt attttccact    9840
agcagtgaaa atgattttc acaactaact tgtaaatata ttttaatcat tacttctttt    9900
tttctagtcc attttattt ggacatcaac cacagacaat ttaaattta tagatgcact    9960 aagaattcac tgcagcagca ggttacatag caaaaatgca aaggtgaaca ggaagtaaat    10020
ttctggcttt tctgctgtaa atagtgaagg aaaattacta aaatcaagta aaactaatgc    10080
atattatttg attgacaata aaatatttac catcacatgc tgcagctgtt ttttaaggaa    10140
catgatgtca ttcattcata cagtaatcat gctgcagaaa tttgcagtct gcaccttatg    10200
gatcacaatt acctttagtt gttttttttg taataattgt agccaagtaa atctccaata    10260
aagttatcgt ctgttcaaaa aaaaaaaaaa aaaaaaaaaa aaaaaaaaaa aaaaaaaaaa    10320
aaa                                                                  10323
```

<210> SEQ ID NO 18
<211> LENGTH: 1374
<212> TYPE: PRT
<213> ORGANISM: Schizosaccharomyces pombe

<400> SEQUENCE: 18

```
Met Asp Ile Ser Ser Phe Leu Leu Pro Gln Leu Leu Arg Lys Tyr Gln
1               5                   10                  15

Gln Asp Val Tyr Asn Ile Ala Ser Lys Gln Asn Thr Leu Leu Val Met
            20                  25                  30

Arg Thr Gly Ala Gly Lys Thr Leu Leu Ala Val Lys Leu Ile Lys Gln
        35                  40                  45

Lys Leu Glu Glu Gln Ile Leu Ile Gln Glu Ser Asn Leu Glu His Lys
    50                  55                  60

Lys Ile Ser Val Phe Leu Val Asn Lys Val Pro Leu Val Phe Gln Gln
65                  70                  75                  80

Ala Glu Tyr Ile Arg Ser Gln Leu Pro Ala Lys Val Gly Met Phe Tyr
                85                  90                  95

Gly Glu Leu Ser Ile Glu Met Ser Glu Gln Leu Leu Thr Asn Ile Ile
            100                 105                 110

Leu Lys Tyr Asn Val Ile Val Ile Thr Ala Asp Leu Phe Tyr Leu Phe
        115                 120                 125

Leu Ala Arg Gly Phe Leu Ser Ile Asn Asp Leu Asn Leu Ile Ile Phe
    130                 135                 140

Asp Glu Cys His His Ala Ile Gly Asn Asp Ala Tyr Ala Arg Ile Met
145                 150                 155                 160

Asn Asp Phe Tyr His Arg Ala Lys Ala Val Leu Ser Lys Lys His Phe
                165                 170                 175
```

-continued

Thr Leu Pro Arg Ile Phe Gly Met Thr Ala Ser Pro Phe Thr Gly Lys
            180                 185                 190

Lys Gly Asn Leu Tyr His Arg Leu Tyr Gln Trp Glu Gln Leu Phe Asp
        195                 200                 205

Ser Lys Ala His Val Val Ser Glu Asn Glu Leu Ala Asp Tyr Phe Cys
    210                 215                 220

Leu Pro Glu Glu Ser Tyr Val Met Tyr Ser Asn Lys Leu Val Val Pro
225                 230                 235                 240

Pro Ser Asp Ser Ile Ile Lys Lys Cys Glu Glu Thr Leu Gln Gly Cys
                245                 250                 255

Lys Leu Ile Ser Arg Ala Val Lys Thr Ala Leu Ala Glu Thr Ile Asp
            260                 265                 270

Met Gly Leu Trp Phe Gly Glu Gln Val Trp Leu Tyr Leu Val Asp Phe
        275                 280                 285

Val Glu Thr Lys Arg Leu Lys Lys Ala Leu Gly Lys Gln Leu Ser
    290                 295                 300

Asp Asp Glu Glu Leu Ala Ile Asp Arg Leu Lys Ile Phe Val Glu Asp
305                 310                 315                 320

Trp Lys Asn Asn Lys Tyr Ser Asp Asn Gly Pro Arg Ile Pro Val Phe
                325                 330                 335

Asp Ser Thr Asp Val Thr Asp Lys Val Phe Lys Leu Leu Glu Leu Leu
            340                 345                 350

Lys Ala Thr Tyr Arg Lys Ser Asp Ser Val Arg Thr Val Ile Phe Val
        355                 360                 365

Glu Arg Lys Ala Thr Ala Phe Thr Leu Ser Leu Phe Met Lys Thr Leu
370                 375                 380

Asn Leu Pro Asn Ile Arg Ala His Ser Phe Ile Gly His Gly Pro Ser
385                 390                 395                 400

Asp Gln Gly Glu Phe Ser Met Thr Phe Arg Arg Gln Lys Asp Thr Leu
                405                 410                 415

His Lys Phe Lys Thr Gly Lys Tyr Asn Val Leu Ile Ala Thr Ala Val
            420                 425                 430

Ala Glu Glu Gly Ile Asp Val Pro Ser Cys Asn Leu Val Ile Arg Phe
        435                 440                 445

Asn Ile Cys Arg Thr Val Thr Gln Tyr Val Gln Ser Arg Gly Arg Ala
450                 455                 460

Arg Ala Met Ala Ser Lys Phe Leu Ile Phe Leu Asn Thr Glu Glu Leu
465                 470                 475                 480

Leu Ile His Glu Arg Ile Leu His Glu Glu Lys Asn Leu Lys Phe Ala
                485                 490                 495

Leu Ser Glu Leu Ser Asn Ser Asn Ile Phe Asp Ser Leu Val Cys Glu
            500                 505                 510

Glu Arg Glu Arg Val Thr Asp Asp Ile Val Tyr Glu Val Gly Glu Thr
        515                 520                 525

Gly Ala Leu Leu Thr Gly Leu Tyr Ala Val Ser Leu Leu Tyr Asn Phe
530                 535                 540

Cys Asn Thr Leu Ser Arg Asp Val Tyr Thr Arg Tyr Tyr Pro Thr Phe
545                 550                 555                 560

Thr Ala Gln Pro Cys Leu Ser Gly Trp Tyr Cys Phe Glu Val Glu Leu
                565                 570                 575

Pro Lys Ala Cys Lys Val Pro Ala Ala Gln Gly Ser Pro Ala Lys Ser
            580                 585                 590

Ile Arg Lys Ala Lys Gln Asn Ala Ala Phe Ile Met Cys Leu Asp Leu

```
            595                 600                 605
Ile Arg Met Gly Leu Ile Asp Lys His Leu Lys Pro Leu Asp Phe Arg
    610                 615                 620

Arg Lys Ile Ala Asp Leu Glu Thr Leu Glu Glu Asp Glu Leu Lys Asp
625                 630                 635                 640

Glu Gly Tyr Ile Glu Thr Tyr Glu Arg Tyr Val Pro Lys Ser Trp Met
                    645                 650                 655

Lys Val Pro Glu Asp Ile Thr Arg Cys Phe Val Ser Leu Leu Tyr Thr
                660                 665                 670

Asp Ala Asn Glu Gly Asp Asn His Ile Phe His Pro Leu Val Phe Val
            675                 680                 685

Gln Ala His Ser Phe Pro Lys Ile Asp Ser Phe Ile Leu Asn Ser Thr
        690                 695                 700

Val Gly Pro Arg Val Lys Ile Val Leu Glu Thr Ile Glu Asp Ser Phe
705                 710                 715                 720

Lys Ile Asp Ser His Leu Leu Glu Leu Lys Lys Ser Thr Arg Tyr
                    725                 730                 735

Leu Leu Gln Phe Gly Leu Ser Thr Ser Leu Glu Gln Gln Ile Pro Thr
                740                 745                 750

Pro Tyr Trp Leu Ala Pro Leu Asn Leu Ser Cys Thr Asp Tyr Arg Phe
            755                 760                 765

Leu Glu Asn Leu Ile Asp Val Asp Thr Ile Gln Asn Phe Phe Lys Leu
        770                 775                 780

Pro Glu Pro Val Gln Asn Val Thr Asp Leu Gln Ser Asp Thr Val Leu
785                 790                 795                 800

Leu Val Asn Pro Gln Ser Ile Tyr Glu Gln Tyr Ala Phe Glu Gly Phe
                    805                 810                 815

Val Asn Ser Glu Phe Met Ile Pro Ala Lys Lys Asp Lys Ala Pro
                820                 825                 830

Ser Ala Leu Cys Lys Lys Leu Pro Leu Arg Leu Asn Tyr Ser Leu Trp
            835                 840                 845

Gly Asn Arg Ala Lys Ser Ile Pro Lys Ser Gln Gln Val Arg Ser Phe
        850                 855                 860

Tyr Ile Asn Asp Leu Tyr Ile Leu Pro Val Ser Arg His Leu Lys Asn
865                 870                 875                 880

Ser Ala Leu Leu Ile Pro Ser Ile Leu Tyr His Ile Glu Asn Leu Leu
                    885                 890                 895

Val Ala Ser Ser Phe Ile Glu His Phe Arg Leu Asp Cys Lys Ile Asp
                900                 905                 910

Thr Ala Cys Gln Ala Leu Thr Ser Ala Glu Ser Gln Leu Asn Phe Asp
            915                 920                 925

Tyr Asp Arg Leu Glu Phe Tyr Gly Asp Cys Phe Leu Lys Leu Gly Ala
        930                 935                 940

Ser Ile Thr Val Phe Leu Lys Phe Pro Asp Thr Gln Glu Tyr Gln Leu
945                 950                 955                 960

His Phe Asn Arg Lys Lys Ile Ile Ser Asn Cys Asn Leu Tyr Lys Val
                    965                 970                 975

Ala Ile Asp Cys Glu Leu Pro Lys Tyr Ala Leu Ser Pro Leu Glu
                980                 985                 990

Ile Arg His Trp Cys Pro Tyr Gly  Phe Gln Lys Ser Thr  Ser Asp Lys
            995                  1000                1005

Cys Arg  Tyr Ala Val Leu Gln  Lys Leu Ser Val Lys  Arg Ile Ala
    1010                 1015                1020
```

Asp Met Val Glu Ala Ser Ile Gly Ala Cys Leu Leu Asp Ser Gly
1025                1030                1035

Leu Asp Ser Ala Leu Lys Ile Cys Lys Ser Leu Ser Val Gly Leu
1040                1045                1050

Leu Asp Ile Ser Asn Trp Asp Glu Trp Asn Asn Tyr Phe Asp Leu
1055                1060                1065

Asn Thr Tyr Ala Asp Ser Leu Arg Asn Val Gln Phe Pro Tyr Ser
1070                1075                1080

Ser Tyr Ile Glu Glu Thr Ile Gly Tyr Ser Phe Lys Asn Lys Lys
1085                1090                1095

Leu Leu His Leu Ala Phe Ile His Pro Ser Met Met Ser Gln Gln
1100                1105                1110

Gly Ile Tyr Glu Asn Tyr Gln Gln Leu Glu Phe Leu Gly Asp Ala
1115                1120                1125

Val Leu Asp Tyr Ile Ile Val Gln Tyr Leu Tyr Lys Lys Tyr Pro
1130                1135                1140

Asn Ala Thr Ser Gly Glu Leu Thr Asp Tyr Lys Ser Phe Tyr Val
1145                1150                1155

Cys Asn Lys Ser Leu Ser Tyr Ile Gly Phe Val Leu Asn Leu His
1160                1165                1170

Lys Tyr Ile Gln His Glu Ser Ala Ala Met Cys Asp Ala Ile Phe
1175                1180                1185

Glu Tyr Gln Glu Leu Ile Glu Ala Phe Arg Glu Thr Ala Ser Glu
1190                1195                1200

Asn Pro Trp Phe Trp Phe Glu Ile Asp Ser Pro Lys Phe Ile Ser
1205                1210                1215

Asp Thr Leu Glu Ala Met Ile Cys Ala Ile Phe Leu Asp Ser Gly
1220                1225                1230

Phe Ser Leu Gln Ser Leu Gln Phe Val Leu Pro Leu Phe Leu Asn
1235                1240                1245

Ser Leu Gly Asp Ala Thr His Thr Lys Ala Lys Gly Asp Ile Glu
1250                1255                1260

His Lys Val Tyr Gln Leu Leu Lys Asp Gln Gly Cys Glu Asp Phe
1265                1270                1275

Gly Thr Lys Cys Val Ile Glu Glu Val Lys Ser Ser His Lys Thr
1280                1285                1290

Leu Leu Asn Thr Glu Leu His Leu Thr Lys Tyr Tyr Gly Phe Ser
1295                1300                1305

Phe Phe Arg His Gly Asn Ile Val Ala Tyr Gly Lys Ser Arg Lys
1310                1315                1320

Val Ala Asn Ala Lys Tyr Ile Met Lys Gln Arg Leu Leu Lys Leu
1325                1330                1335

Leu Glu Asp Lys Ser Asn Leu Leu Leu Tyr Ser Cys Asn Cys Lys
1340                1345                1350

Phe Ser Lys Lys Lys Pro Ser Asp Glu Gln Ile Lys Gly Asp Gly
1355                1360                1365

Lys Val Lys Ser Leu Thr
1370

<210> SEQ ID NO 19
<211> LENGTH: 4125
<212> TYPE: DNA
<213> ORGANISM: Schizosaccharomyces pombe

```
<400> SEQUENCE: 19
atggatattt caagtttttct acttcctcaa cttttacgta aatatcaaca agatgtgtat      60
aatatcgcga gcaagcaaaa tactttactt gttatgagaa cgggcgctgg taagacatta     120
cttgctgtga agttgataaa acaaaagctc gaggagcaaa ttttaatcca agaatcaaat     180
cttgaacata aaaaaatatc agttttctc gtcaacaaag tcccttttggt atttcaacaa     240
gcggaataca ttcgatctca actaccggct aaggttggca tgttttatgg cgaattatct     300
atagaaatga gcgagcagtt gttgactaat attatattga agtataatgt gattgttatt     360
actgcagatt tgttctattt gtttcttgca agaggttttc tttcaataaa tgatttgaat     420
ttaattatat tcgacgaatg tcatcatgca attggaaatg atgcgtatgc tcgcatcatg     480
aatgatttt atcacagagc caaagcagta ttgtcaaaaa acatttcac cctaccaaga     540
attttttggta tgactgcttc accattcact ggaaaaaaag gaaacttata ccatcgactg     600
tatcaatggg agcaattatt tgattctaaa gcacacgtgg tttcggaaaa cgagctagcc     660
gattacttct gtcttcccga agaaagctat gtaatgtatt ccaataagtt ggttgtgcca     720
ccctcggatt ctattatcaa gaaatgcgag gaaactcttc aaggatgcaa gttaatttct     780
cgggctgtta agactgcttt agcagaaacc atagatatgg tctttggtt tggggagcaa     840
gtttggttat atttggttga ttttgtggaa acgaaaagat taaaaaaaaa ggctttaggg     900
aagcagttgt cagatgacga ggaactggca attgaccggt taaaaatatt tgttgaagat     960
tggaaaaata caaatattc agacaatggc cctagaatcc ctgttttga ttccactgat    1020
gttactgata agtctttaa actcttagaa ttgttaaagg ctacttaccg caaaagtgat    1080
agcgttcgta cggttattt cgttgaaaga aaagctacgg cgtttacttt aagtttgttt    1140
atgaaaactc ttaatctgcc taacatccgc gctcattctt ttataggaca tggaccgtcc    1200
gatcagggtg aattttctat gacattcagg aggcaaaaag ataccttca taagtttaag    1260
actgaaaat ataatgtttt aattgctact gcagttgcag aagaaggtat cgatgtacca    1320
tcatgtaact tagttatacg cttcaatatt tgtcggactg tcacccagta tgtccaatct    1380
cgaggtagag cgagagcaat ggcttcaaag tttctaattt ttttaaacac agaagagttg    1440
ttaattcatg aacgcattct acacgaagaa aaaaatctta aatttgccct ttcagagctc    1500
agcaattcga atattttga ttcattggta tgtgaggaaa gagaacgtgt gactgatgat    1560
atcgtctatg aagttggcga gactggtgct ttactcacag ggttgtatgc agttagtctg    1620
ctttataact tttgtaacac actttcaaga gacgtataca caagatatta tcccactttt    1680
acagctcaac cctgtctttc aggttggtat tgttttgagg tagaattgcc aaaagcctgc    1740
aaagttccag cggctcaagg atctcccgct aaatcaatta ggaaagccaa acagaatgct    1800
gcgttcatca tgtgtttgga tctgattcgt atgggtctta tagacaaaca tttaaaaccc    1860
ctagattta gaagaaaaat tgccgaccttt gaaactcttg aggaagacga gctaaaagat    1920
gaaggttata tcgagacata tgagcgctat gtaccaaaaa gttggatgaa agttcctgaa    1980
gatattacac gttgcttcgt ctctttactt tatactgatg ctaatgaagg agacaatcat    2040
atattccatc cctagtgtt tgtacaagct cattcattcc ccaaaattga tagctttatt    2100
cttaattcga ctgttggccc ccgagttaaa attgttttag aaacgattga ggatagttttt    2160
aagatcgatt ctcatctgct tgagttgtta aaaaaatcaa ctcgttatct acttcaattc    2220
ggtttatcta cttctcttga gcaacaaata cctactcctt actggcttgc gcctttaaat    2280
ttgtcatgca cggattaccg gttcttagaa aatctgatag atgttgacac tatccaaaat    2340
```

```
ttttttaaat taccggaacc tgttcaaaat gttactgatt tgcaatccga tactgtatta    2400
ttagtaaatc cacagtcaat atatgaacag tatgcttttg agggatttgt caattctgaa    2460
tttatgattc ctgctaaaaa gaaagataag gccccttctg ccttatgtaa gaaacttcct    2520
ttacgattaa attattcact tggggcaata gagctaaat ccattcccaa atcacagcaa     2580
gtgcgcagtt tttatatcaa tgacctctat attctcccag tctctagaca tttgaaaaac    2640
agcgccttgc taatacccatc catactgtac catattgaaa acttattggt cgcctcttct    2700
tttatcgaac actttcgact tgattgtaaa attgacactg cttgtcaggc tttaacatct    2760
gcggaatcac aattgaattt tgattacgat cgtctagagt tttacggaga ctgctttcta    2820
aaattgggtg cttctattac agttttttg aaatttcctg atactcaaga gtaccaactg     2880
cattttaatc gaagaaaat tattagcaac tgtaatttgt ataaagtagc aatagattgt     2940
gagttgccga agtatgctct ctcgactccc ttggaaatcc gtcattggtg tccatatggt    3000
tttcagaaaa gcacatcgga taagtgccgc tacgccgttt tacagaaatt atcggttaag   3060
aggatagcag atatggtcga agctagtatc ggtgcatgtc ttttagacag tggacttgac   3120
tcagcactca agatctgtaa atctttaagc gttggtctgc tggatatcag caattgggat    3180
gagtggaaca attattttga tttaaataca tatgcggatt cactgagaaa tgttcaattc    3240
ccttactcct cgtatataga ggaaactatt ggatattcat ttaaaaacaa gaaactactc    3300
catttggcat ttattcatcc ttccatgatg tctcagcaag gtatttacga aaactatcaa    3360
cagttggagt ttttgggtga tgctgtattg gattacatta tcgtacaata cctttataaa    3420
aagtatccta acgcaacttc tggcgaatta actgattaca aatctttta tgtgtgtaac    3480 aagagtctat catacattgg ctttgttttg aatttgcaca aatatatcca acatgaaagc    3540
gcagcaatgt gtgatgcaat atttgaatat caagaattaa ttgaagcgtt cagggagact    3600
gcttcagaga atccgtggtt ctggtttgaa attgattcac caaagttcat ttcagatact    3660
ttagaagcta tgatatgtgc cattttttg gattctgggt ttagtttaca atctctacaa     3720 ttcgtttac ctcttttttct taattcgtta ggggatgcga cacatactaa ggctaaagga    3780
gatattgaac acaaggtata ccaattactg aaagatcagg gatgtgaaga cttcggaaca    3840
aagtgtgtca tcgaggaggt gaaatccagt cacaaaacat tgttaaatac tgaactccat    3900
ttaacaaagt attatgggtt tcattcttc cgccacggga atattgttgc ttacggcaaa    3960
tcccgtaaag ttgccaatgc aaagtatatt atgaaacaaa gacttctcaa attgttagag   4020
gataagtcta acttactttt gtattcttgt aattgcaaat ttagtaagaa aaagccatca    4080
gatgagcaaa taaaggaga tggaaaagtt aaaagtttga cttga                     4125
```

<210> SEQ ID NO 20
<211> LENGTH: 754
<212> TYPE: PRT
<213> ORGANISM: Giardia lamblia virus

<400> SEQUENCE: 20

Met His Ala Leu Gly His Cys Cys Thr Val Val Thr Thr Arg Gly Pro
1               5                   10                  15

Ser His Trp Leu Leu Leu Leu Asp Thr His Leu Gly Thr Leu Pro Gly
            20                  25                  30

Phe Lys Val Ser Ala Gly Arg Gly Leu Pro Ala Ala Glu Val Tyr Phe
        35                  40                  45

Glu Ala Gly Pro Arg Val Ser Leu Ser Arg Thr Asp Ala Thr Ile Val

-continued

```
            50                  55                  60
Ala Val Tyr Gln Ser Ile Leu Phe Gln Leu Leu Gly Pro Thr Phe Pro
 65                  70                  75                  80

Ala Ser Trp Thr Glu Ile Gly Ala Thr Met Pro His Asn Glu Tyr Thr
                     85                  90                  95

Phe Pro Arg Phe Ile Ser Asn Pro Pro Gln Phe Ala Thr Leu Ala Phe
                100                 105                 110

Leu Pro Leu Leu Ser Pro Thr Ser Pro Leu Asp Leu Arg Ala Leu Met
                115                 120                 125

Val Thr Ala Gln Leu Met Cys Asp Ala Lys Arg Leu Ser Asp Glu Tyr
                130                 135                 140

Thr Asp Tyr Ser Thr Leu Ser Ala Ser Leu His Gly Arg Met Val Ala
145                 150                 155                 160

Thr Pro Glu Ile Ser Trp Ser Leu Tyr Val Leu Gly Ile Asp Ser
                165                 170                 175

Thr Gln Thr Ser Leu Ser Tyr Phe Thr Arg Ala Asn Glu Ser Ile Thr
                180                 185                 190

Tyr Met Arg Tyr Tyr Ala Thr Ala His Asn Ile His Leu Arg Ala Ala
                195                 200                 205

Asp Leu Pro Leu Val Ala Ala Val Arg Leu Asp Asp Leu Lys Asp His
                210                 215                 220

Gln Ile Pro Ala Pro Gly Ser Trp Asp Leu Ala Pro Lys Leu Arg
225                 230                 235                 240

Phe Leu Pro Pro Glu Leu Cys Leu Leu Leu Pro Asp Glu Phe Asp Leu
                245                 250                 255

Ile Arg Val Gln Ala Leu Gln Phe Leu Pro Glu Ile Ala Lys His Ile
                260                 265                 270

Cys Asp Ile Gln Asn Thr Ile Cys Ala Leu Asp Lys Ser Phe Pro Asp
                275                 280                 285

Cys Gly Arg Ile Gly Gly Glu Arg Tyr Phe Ala Ile Thr Ala Gly Leu
                290                 295                 300

Arg Leu Asp Gln Gly Arg Gly Arg Gly Leu Ala Gly Trp Arg Thr Pro
305                 310                 315                 320

Phe Gly Pro Phe Gly Val Ser His Thr Asp Val Phe Gln Arg Leu Glu
                325                 330                 335

Leu Leu Gly Asp Ala Val Leu Gly Phe Ile Val Thr Ala Arg Leu Leu
                340                 345                 350

Cys Leu Phe Pro Asp Ala Ser Val Gly Thr Leu Val Glu Leu Lys Met
                355                 360                 365

Glu Leu Val Arg Asn Glu Ala Leu Asn Tyr Leu Val Gln Thr Leu Gly
370                 375                 380

Leu Pro Gln Leu Ala Glu Phe Ser Asn Asn Leu Val Ala Lys Ser Lys
385                 390                 395                 400

Thr Trp Ala Asp Met Tyr Glu Glu Ile Val Gly Ser Ile Phe Thr Gly
                405                 410                 415

Pro Asn Gly Ile Tyr Gly Cys Glu Glu Phe Leu Ala Lys Thr Leu Met
                420                 425                 430

Ser Pro Glu His Ser Lys Thr Val Gly Ser Ala Cys Pro Asp Ala Val
                435                 440                 445

Thr Lys Ala Ser Lys Arg Val Cys Met Gly Glu Ala Gly Ala His Glu
450                 455                 460

Phe Arg Ser Leu Val Asp Tyr Ala Cys Glu Gln Gly Ile Ser Val Phe
465                 470                 475                 480
```

```
Cys Ser Ser Arg Val Ser Thr Met Phe Leu Glu Arg Leu Arg Asp Ile
                485                 490                 495

Pro Ala Glu Asp Met Leu Asp Trp Tyr Arg Leu Gly Ile Gln Phe Ser
            500                 505                 510

His Arg Ser Gly Leu Ser Gly Pro Gly Gly Val Val Ser Val Ile Asp
        515                 520                 525

Ile Met Thr His Leu Ala Arg Gly Leu Trp Leu Gly Ser Pro Gly Phe
    530                 535                 540

Tyr Val Glu Gln Gln Thr Asp Lys Asn Glu Ser Ala Cys Pro Pro Thr
545                 550                 555                 560

Ile Pro Val Leu Tyr Ile Tyr His Arg Ser Val Gln Cys Pro Val Leu
                565                 570                 575

Tyr Gly Ser Leu Thr Glu Thr Pro Thr Gly Pro Val Ala Ser Lys Val
            580                 585                 590

Leu Ala Leu Tyr Glu Lys Ile Leu Ala Tyr Glu Ser Ser Gly Gly Ser
        595                 600                 605

Lys His Ile Ala Ala Gln Thr Val Ser Arg Ser Leu Ala Val Pro Ile
    610                 615                 620

Pro Ser Gly Thr Ile Pro Phe Leu Ile Arg Leu Leu Gln Ile Ala Leu
625                 630                 635                 640

Thr Pro His Val Tyr Gln Lys Leu Glu Leu Leu Gly Asp Ala Phe Leu
                645                 650                 655

Lys Cys Ser Leu Ala Leu His Leu His Ala Leu His Pro Thr Leu Thr
            660                 665                 670

Glu Gly Ala Leu Thr Arg Met Arg Gln Ser Ala Glu Thr Asn Ser Val
        675                 680                 685

Leu Gly Arg Leu Thr Lys Arg Phe Pro Ser Val Ser Glu Val Ile
    690                 695                 700

Ile Glu Ser His Pro Lys Ile Gln Pro Asp Ser Lys Val Tyr Gly Asp
705                 710                 715                 720

Thr Phe Glu Ala Ile Leu Ala Ala Ile Leu Leu Ala Cys Gly Glu Glu
                725                 730                 735

Ala Ala Gly Ala Phe Val Arg Glu His Val Leu Pro Gln Val Val Ala
            740                 745                 750

Asp Ala
```

<210> SEQ ID NO 21
<211> LENGTH: 2265
<212> TYPE: DNA
<213> ORGANISM: Giardia lamblia virus

<400> SEQUENCE: 21

```
atgcatgctt tgggacactg ttgcacagtt gtgactacta gaggaccatc ccactggttg      60
ctacttctag acactcacct gggcaccttg ccagggttta aggttagtgc aggccgaggg     120
cttcccgccg cagaggtgta ctttgaagcg ggtccgaggg tgtctctctc tcgaactgat     180
gcaactatag tagccgtgta tcagtccatt ctctttcagc tgctgggacc cacatttcct     240
gcttcatgga ctgagattgg agcaacaatg cctcacaatg aatacacttt ccctcgattt     300
atatccaatc caccacaatt cgccaccctg gcattttttac ccttactatc tcctaccagc     360
cctctggact tgcgtgcatt aatggtcact gcacaactca tgtgtgatgc aaagcgcttg     420
tcagatgaat atacagacta ttccactttta tctgcatccc tccatgggcg tatggttgca     480
actcccgaaa taagctggtc tctttatgtc gttcttggga tcgattctac ccaaactagc     540
```

```
ctttcttact ttaccagagc aaatgaatca ataacataca tgagatacta tgcaacagcc    600
cacaatattc acctgcgtgc tgcagatctt ccgcttgtgg cagcagtcag attagacgat    660
ctaaaagacc accagattcc cgcgcctgga tcctgggatg atttggctcc caagcttcgc    720
ttcctgccgc ctgagctctg cctactgctg ccagatgaat tgatctaat cagggtccag    780 gcgcttcaat ttctaccaga gattgctaag cacatatgtg acatacagaa tacaatctgt    840
gccctggata aaagctttcc tgactgtggg cggatcggtg gcgagcgata ctttgcaatc    900
actgccggac ttcggctcga tcaggggcgt ggacgagggc ttgccggttg agaacaccc    960 tttgggcctt ttggtgtaag tcacaccgat gttttccagc gactcgaatt gctaggagat   1020
gctgtgttag gctttatcgt gactgcccgc ctccttttgcc ttttttccaga tgcgtctgtg   1080 ggaacacttg ttgagctaaa gatggagctt gttcgcaatg aggctctaaa ctatcttgta   1140
caaacgcttg gacttcctca gttggcggag ttttccaaca accttgtggc gaagagcaaa   1200
acatgggcag atatgtatga ggagatcgtt ggatcaatct ttacgggacc taatggaatc   1260
tatggctgtg aggaatttct tgcgaagacg cttatgagtc ccgaacactc caagacagta   1320
ggatctgcct gtccagatgc agtcaccaag gcatcaaagc gtgtttgcat gggagaagcg   1380
ggggcgcatg aattcagaag ccttgtggac tatgcttgtg agcaaggcat tagtgtcttc   1440
tgttcttcgc gggtgtcaac tatgtttctc gagcgtctca gagacattcc agcagaggac   1500
atgctagatt ggtaccgact tggtatccag ttttcgcatc gttcaggcct atcaggacct   1560
ggcggcgtcg tatcagttat agacataatg acacatttgg ctcgaggcct atggctgggc   1620
tctccaggct tctatgttga acagcaaact gataagaatg agtcggcttg tccgcccact   1680
atacctgttt tatatatcta tcatcgctct gtgcagtgtc ctgttttata tgggtcgctc   1740
acagaaaccc ctacagggcc cgttgcttct aaggttctcg ctctctatga aagattctg    1800 gcatatgagt catcaggagg tagtaagcat atagcagctc agacagttag cagatctctg   1860
gccgtaccca ttcctagtgg cactatcccc ttcctgattc ggttattgca aatagcacta   1920
actcctcacg tgtaccaaaa acttgagctt cttggagacg cattcctgaa gtgcagcctt   1980
gctctccatc tccacgctct ccaccccacg ctcacagagg cgctcttac acgcatgcgg   2040 caatctgcag aaacaaattc tgtactggga agattgacaa aaaggtttcc ttctgtagtt   2100
tctgaggtta ttatagaatc ccatccgaaa atacagcctg acagcaaggt ttatggcgat   2160
acatttgaag ccattttggc agcaattctt cttgcgtgcg gggaagaggc agcaggtgct   2220
tttgttcgag agcatgttct cccacaagta gtagctgatg cgtag                   2265
```

<210> SEQ ID NO 22
<211> LENGTH: 91
<212> TYPE: DNA
<213> ORGANISM: Artificial Sequence
<220> FEATURE:
<223> OTHER INFORMATION: oligonucleotide

<400> SEQUENCE: 22

```
cccgggttca cgccattctc ctgcctcagc ctcacgagta gctgggacta caggcgcccg    60
acaccactcc cggctaattt tttgtatttt t                                    91
```

<210> SEQ ID NO 23
<211> LENGTH: 29
<212> TYPE: DNA
<213> ORGANISM: Artificial Sequence
<220> FEATURE:

<223> OTHER INFORMATION: Oligonucleotide

<400> SEQUENCE: 23
tgaggtcagg agatcgagac catcccggc                                29

<210> SEQ ID NO 24
<211> LENGTH: 29
<212> TYPE: DNA
<213> ORGANISM: Artificial Sequence
<220> FEATURE:
<223> OTHER INFORMATION: oligonucleotide

<400> SEQUENCE: 24
tgaggtcagg agatcgaaac catcccggc                                29

<210> SEQ ID NO 25
<211> LENGTH: 29
<212> TYPE: DNA
<213> ORGANISM: Artificial Sequence
<220> FEATURE:
<223> OTHER INFORMATION: oligonucleotide

<400> SEQUENCE: 25
tgaggtcagg agttcgaaac catcccggc                                29

<210> SEQ ID NO 26
<211> LENGTH: 29
<212> TYPE: DNA
<213> ORGANISM: Artificial Sequence
<220> FEATURE:
<223> OTHER INFORMATION: oligonucleotide

<400> SEQUENCE: 26
tgaggtcagg agttcgagac catcccggc                                29

<210> SEQ ID NO 27
<211> LENGTH: 291
<212> TYPE: DNA
<213> ORGANISM: Homo sapiens

<400> SEQUENCE: 27
ggccgggcgc ggtggctcac ggctgtaatc ccagcacttt gggaggccga ggcgggtgga      60
tcacctgagg tcaggagttc gagagcagcc tggccaacat ggtgaaaccc cgtctctact     120
aaaaatacaa aaattagccg grcgtggtgg cgggcgcctg taatcccacc tactcgggag    180
gctgaggcag gagaatcgct tgaacccggg aggccgagct tgcagtgagc cgagatcgcg    240
ccactgcact ccagcctggg caacaagagc gaaactccgt ctcaaaaaaa a            291

<210> SEQ ID NO 28
<211> LENGTH: 302
<212> TYPE: DNA
<213> ORGANISM: Homo sapiens

<400> SEQUENCE: 28
ggccgggcgc aatggctcag acctctaatc ccgacacttt gcgaggctga ggcgggcaga      60
tcacctgagg tcaggagttc gaaccatcc tggctgacat ggtgaaaccc cgtctctact     120
aaaaatacaa aaattagcc gggcgtggtg gtgggtgcct gtagtcccag ctactcggca    180
ggagaatggc gtgaaccctg gaggcggagg ttacggtgag ccgaggtcgc gccactgcac    240
tccagcctgg gctacagagc gcgacttggt ctcaaaaaac aaacaggcaa aagagaaaaa   300
aa                                                                  302

```
<210> SEQ ID NO 29
<211> LENGTH: 221
<212> TYPE: DNA
<213> ORGANISM: Homo sapiens

<400> SEQUENCE: 29
atcccagcac tctggcaggc cgaggcgggt ggatcatgag gtcaggagat cgagaccatc      60
ccggccaaca cagcgaaacc ccatctctac taaaaaatac aaaaagaaaa aattagccag     120
gtgtggtggt gggcgcctgt agtctcagct gctcgggagg ctgaggcggg agagttgctt     180
gggcccggga ggcggaggtt gcagtgagcc gggatcacgc c                        221
```